(12) United States Patent
Peer Mohamed et al.

(10) Patent No.: US 10,711,011 B2
(45) Date of Patent: Jul. 14, 2020

(54) SUBSTITUTED OXAZOLIDINES AS ANTI-BACTERIAL AGENTS

(71) Applicant: BUGWORKS RESEARCH, INC., Wilmington, DE (US)

(72) Inventors: Shahul Hameed Peer Mohamed, Bangalore (IN); Nagakumar Bharatham, Bangalore (IN); Nainesh Katagihallimath, Bangalore (IN); Sreevalli Sharma, Bangalore (IN); Radha Nandishaiah, Bangalore (IN)

(73) Assignee: BUGWORKS RESEARCH, INC., Wilmington, DE (US)

( * ) Notice: Subject to any disclaimer, the term of this patent is extended or adjusted under 35 U.S.C. 154(b) by 0 days.

(21) Appl. No.: 16/301,887

(22) PCT Filed: May 19, 2017

(86) PCT No.: PCT/IN2017/050188
§ 371 (c)(1),
(2) Date: Nov. 15, 2018

(87) PCT Pub. No.: WO2017/199265
PCT Pub. Date: Nov. 23, 2017

(65) Prior Publication Data
US 2019/0292199 A1  Sep. 26, 2019

(30) Foreign Application Priority Data
May 20, 2016  (IN) .............................. 201641017526

(51) Int. Cl.
| | |
|---|---|
| A61K 31/421 | (2006.01) |
| C07D 263/04 | (2006.01) |
| C07D 498/04 | (2006.01) |
| A61P 31/04 | (2006.01) |
| A61K 31/4439 | (2006.01) |
| A61K 31/5383 | (2006.01) |
| A61K 45/06 | (2006.01) |
| C07D 413/14 | (2006.01) |

(52) U.S. Cl.
CPC ........ C07D 498/04 (2013.01); A61K 31/4439 (2013.01); A61K 31/5383 (2013.01); A61K 45/06 (2013.01); A61P 31/04 (2018.01); C07D 413/14 (2013.01)

(58) Field of Classification Search
CPC ............................ A61K 31/421; C07D 263/04
USPC .......................................... 514/376; 548/229
See application file for complete search history.

(56) References Cited

FOREIGN PATENT DOCUMENTS

| | | |
|---|---|---|
| WO | 2008/126024 | 10/2008 |
| WO | 2010/041219 | 4/2010 |
| WO | 2014/170821 | 10/2014 |
| WO | WO 17/199265 | 11/2017 |

OTHER PUBLICATIONS

Jordan, V. C. Nature Reviews: Drug Discovery, 2, 2003, 205.
Dörwald, F. Zaragoza. Side Reactions in Organic Synthesis: A Guide to Successful Synthesis Design, Weinheim: WILEY-VCH Verlag GmbH & Co. KGaA, 2005, Preface.
Vippagunta, et al. Advanced Drug Delivery Reviews, 48, 2001, 18.
International Search Report and Written Opinion for PCT/IN2017/050188 dated Aug. 18, 2017.

*Primary Examiner* — Douglas M Willis
(74) *Attorney, Agent, or Firm* — Thomas|Horstemeyer, LLP

(57) ABSTRACT

The present disclosure relates to compounds of Formula I, its stereoisomers, pharmaceutically acceptable salts, complexes, hydrates, solvates, tautomers, polymorphs, racemic mixtures, optically active forms thereof and pharmaceutical compositions containing them as the active ingredient which can be used as medicaments. The aforementioned substances can also be used in the manufacture of medicaments for treatment, prevention or suppression of diseases, and conditions mediated by microbes. The present disclosure also relates to the synthesis and characterization of aforementioned substances.

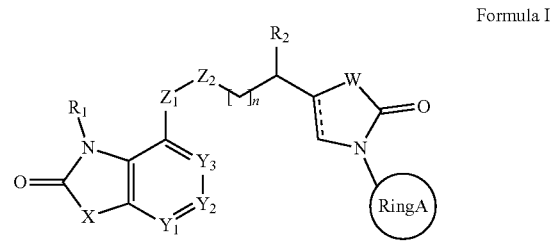

Formula I

12 Claims, 2 Drawing Sheets

SUBSTITUTED OXAZOLIDINES AS ANTI-BACTERIAL AGENTS

CROSS REFERENCE TO RELATED APPLICATIONS

This application is the 35 U.S.C. § 371 national stage application of PCT Application No. PCT/IN2017/050188, filed May 19, 2018, where the PCT claims priority to and the benefit of IN Patent Application No. 201641017526, filed May 20, 2016, all of which are herein incorporated by reference in their entireties.

The present invention relates to the field of medicinal chemistry and more particularly to the development of antimicrobial compounds effective against bacteria, virus, fungi and protozoa including spectrum of Gram-negative and Gram-positive pathogens. The present disclosure relates to compounds of Formula I, its stereoisomers, pharmaceutically acceptable salts, complexes, hydrates, solvates, tautomers, polymorphs, racemic mixtures, optically active forms and pharmaceutically active derivative thereof and pharmaceutical compositions containing them as the active ingredient. The present disclosure further relates to the synthesis and characterization of aforementioned compounds to exhibit high antimicrobial activity.

The compounds of the present disclosure are useful as medicaments and their use in the manufacture of medicaments for treatment, prevention or suppression of diseases, and conditions mediated by microbes. The present invention also provides evidence for treating infection caused by microbes.

BACKGROUND

There is an alarming worldwide concern regarding the rapid evolution of antibiotic resistance, which could result in strains against which there are no effective antibacterial agents. In general, bacterial pathogens may be classified as either Gram-positive or Gram-negative pathogens. Antibiotic compounds with effective activity against both Gram-positive and Gram-negative pathogens are regarded as having a broad spectrum of activity. Current antibacterial drugs used to treat and prevent bacterial infection have been found to have limited effect. Further, there is a continuing need to identify new compounds with potent antibacterial activity with reduced potential for developing resistance, which possess improved efficacy against bacterial infections that resist treatment with currently available antibiotics, or which possess selectivity against target microorganisms.

From the foregoing, it is clear that compounds used in the state of the art to treat and prevent bacterial infection have been found to have limited effect. Further, there is a continuing need to identify new compounds with improved antibacterial activity, which have less potential for developing resistance, which possess improved effectiveness against bacterial infections that resist treatment with currently available antibiotics, or which possess unexpected selectivity against target microorganisms.

SUMMARY

The present disclosure is based on the surprising discovery that compounds of Formula I (see below) exhibits advantageous antimicrobial properties. Thus, the present disclosure provides a compound of Formula I

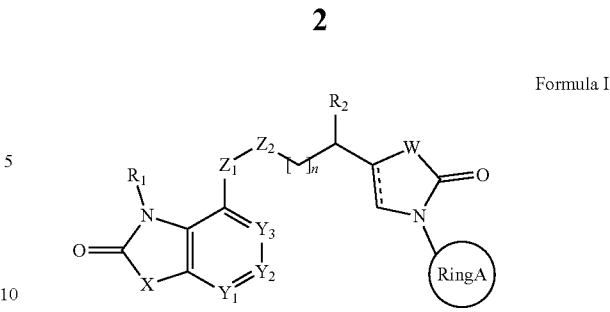

Formula I or its stereoisomers, pharmaceutically acceptable salts, complexes, hydrates, solvates, tautomers, polymorphs, racemic mixtures, optically active forms and pharmaceutically active derivative thereof, wherein $R_1$ is selected from the group consisting of hydrogen, $C_{1-6}$ alkyl, $C_{2-6}$ alkenyl, and $C_{3-6}$ cycloalkyl, each of which is unsubstituted or substituted with 1 to 3 groups independently selected from halogen, hydroxy, amino, oxetane, —$OC_{1-6}$ alkyl, $C_{3-6}$ cycloalkylamino, $C_{1-6}$ alkylamino, or di($C_{1-6}$ alkyl)amino;

$R_2$ is selected from the group consisting of hydrogen, hydroxyl, and amino;

X is —NH, —$NC_{1-6}$ alkyl, O, or $CR_3R_4$;

$R_3$ and $R_4$ are independently selected from the group consisting of hydrogen, halogen, and $C_{1-6}$ alkyl;

$Y_1$ is N or $CR_5$;

$R_5$ is selected from the group consisting of hydrogen, halogen, cyano, —$OC_{1-6}$ alkyl, —$OC_{1-6}$ haloalkyl, and $C_{1-6}$ alkyl;

$Y_2$ is N or CH;

$Y_3$ is N or $CR_6$;

$R_6$ is selected from the group consisting of hydrogen, halogen, cyano, —$OC_{1-6}$ alkyl, and —$OC_{1-6}$ haloalkyl;

$Z_1$ is NH when $Z_2$ is $C_{1-6}$ alkylene; or $Z_1$ is $C_{1-6}$ alkylene when $Z_2$ is NH;

n is 1 or 2;

W is $CH_2$ wherein dotted line ($---$) represents no bond; W is O when dotted line ($---$) represents either a bond or no bond;

Ring A is selected from the group consisting of a 3-10 membered substituted or unsubstituted heteroaryl ring system which is unsaturated or partially unsaturated optionally having up to three heteroatom independently selected from O, N, NH or S.

The present disclosure further relates to a compound of Formula I or its stereoisomers, pharmaceutically acceptable salts, complexes, hydrates, solvates, tautomers, polymorphs, racemic mixtures, optically active forms and pharmaceutically active derivative thereof, for use in killing or inhibiting the growth of a microorganism selected from the group consisting of bacteria, virus, fungi and protozoa.

The present disclosure further relates to use of a compound of Formula I or its stereoisomers, pharmaceutically acceptable salts, complexes, hydrates, solvates, tautomers, polymorphs, racemic mixtures, optically active forms and pharmaceutically active derivative thereof, in killing or inhibiting the growth of a microorganism selected from the group consisting of bacteria, virus, fungi and protozoa.

The present disclosure further relates to a compound of Formula I or its stereoisomers, pharmaceutically acceptable salts, complexes, hydrates, solvates, tautomers, polymorphs, racemic mixtures, optically active forms and pharmaceutically active derivative thereof, for use in treating a disease or condition in a patient wherein said disease or condition is caused by a microorganism selected from the group consisting of bacteria, virus, fungi and protozoa.

The present disclosure further relates to use of a compound of Formula I or its stereoisomers, pharmaceutically acceptable salts, complexes, hydrates, solvates, tautomers, polymorphs, racemic mixtures, optically active forms and pharmaceutically active derivative thereof, in treating disease or condition in a patient, wherein said disease or condition is caused by a microorganism selected from the group consisting of bacteria, virus, fungi and protozoa. The patient is a typically a mammal, preferably a human.

The present disclosure further relates to a method of treating a disease or condition in a patent, said method comprising administering to a patient a compound of Formula I, or its stereoisomers, pharmaceutically acceptable salts, complexes, hydrates, solvates, tautomers, polymorphs, racemic mixtures, optically active forms and pharmaceutically active derivative thereof, wherein said disease or condition is caused by microorganism selected from the group consisting of bacteria, virus, fungi and protozoa.

The present disclosure relates to a composition comprising a compound of Formula I or its stereoisomers, pharmaceutically acceptable salts, complexes, hydrates, solvates, tautomers, polymorphs, racemic mixtures, optically active forms and pharmaceutically active derivative thereof together with a carrier.

The present disclosure relates to a pharmaceutical composition comprising a compound of Formula I or its stereoisomers, pharmaceutically acceptable salts, complexes, hydrates, solvates, tautomers, polymorphs, racemic mixtures, optically active forms and pharmaceutically active derivative thereof, together with a pharmaceutically acceptable carrier, optionally in combination with one or more other pharmaceutical compositions.

The present disclosure relates to a process of preparation of compound of Formula I or its stereoisomers, pharmaceutically acceptable salts, complexes, hydrates, solvates, tautomers, polymorphs, racemic mixtures, optically active forms and pharmaceutically active derivative thereof.

The present disclosure relates to a process of preparation of a composition comprising a compound of Formula I or its stereoisomers, pharmaceutically acceptable salts, complexes, hydrates, solvates, tautomers, polymorphs, racemic mixtures, optically active forms and pharmaceutically active derivative thereof together with a carrier.

The present disclosure relates to a process of preparation of pharmaceutical composition comprising a compound of Formula I or its stereoisomers, pharmaceutically acceptable salts, complexes, hydrates, solvates, tautomers, polymorphs, racemic mixtures, optically active forms and pharmaceutically active derivative thereof, together with a pharmaceutically acceptable carrier, optionally in combination with one or more other pharmaceutical compositions.

These and other features, aspects, and advantages of the present subject matter will become better understood with reference to the following description. This summary is provided to introduce a selection of concepts in a simplified form. This summary is not intended to identify key features or essential features of the disclosure, nor is it intended to be used to limit the scope of the subject matter.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

Figure 1:
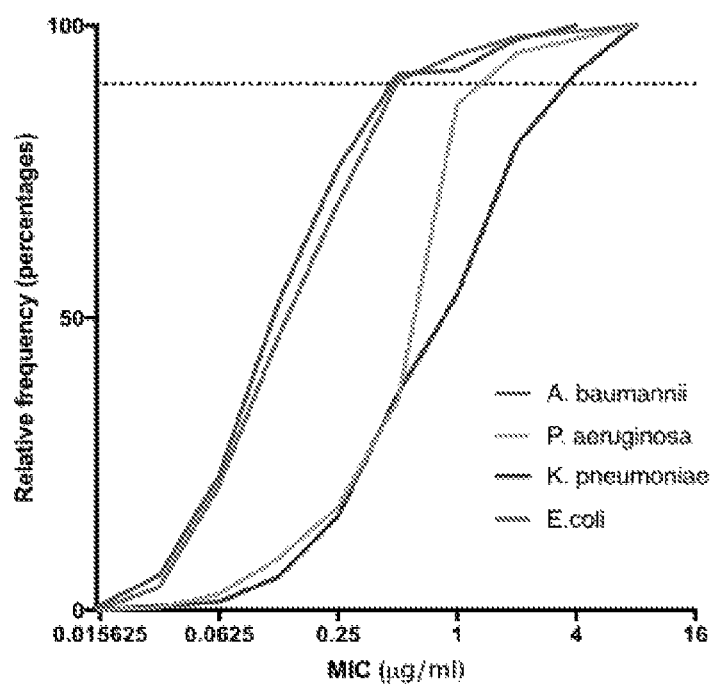
FIG. 1 illustrates the $MIC_{90}$ of Example 14 against clinical strains of four major gram negative bacterial species, in accordance with an embodiment of the present disclosure.

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. Throughout this specification, unless the context requires otherwise the word "comprise", and variations, such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

In the structural formulae given herein and throughout the present disclosure, the following terms have been indicated meaning, unless specifically stated otherwise.

In this specification, the prefix $C_{x-y}$ as used in terms such as $C_{x-y}$alkyl and the like (where x and y are integers) indicates the numerical range of carbon atoms that are present in the group; for example, $C_{1-6}$ alkyl includes $C_1$ alkyl (methyl), $C_2$ alkyl (ethyl), $C_3$ alkyl (propyl and isopropyl) and $C_4$ alkyl (butyl, 1-methylpropyl, 2-methylpropyl, and t-butyl). Unless specifically stated, the bonding atom of a group may be any suitable atom of that group; for example, propyl includes prop-1-yl and prop-2-yl.

The term "alkyl" refers to a monoradical branched or unbranched saturated hydrocarbon chain having from 1 to 10 carbon atoms. This term is exemplified by groups such as n-butyl, iso-butyl, t-butyl, n-hexyl, n-decyl, and the like. The groups may be optionally substituted.

The term "alkylene" refers to a diradical branched or unbranched saturated hydrocarbon chain having from 1 to 6 carbon atoms. This term is exemplified by groups such as methylene, ethylene, propylene, butylene, hexylene, and the like. The groups may be optionally substituted. Representative substituted alkylene groups include hydroxyl substituted alkylenes.

The term "alkenyl" refers to a monoradical of a branched or unbranched unsaturated hydrocarbon group preferably having from 2, 3, 4, 5, or 6 carbon atoms and having 1, 2, or 3, double bond (vinyl), preferably 1 double bond. The groups may be optionally substituted.

The term "cycloalkyl" refers to carbocyclic groups of from 3 to 12 carbon atoms having a single cyclic ring or multiple condensed rings which may be partially unsaturated. Such cycloalkyl groups include, by way of example, single ring structures such as cyclopropyl, cyclobutyl, cyclopentyl, cyclopentenyl, cyclohexyl, cyclohexenyl, and the like, or multiple ring structures or carbocyclic groups to which is fused an aryl group, for example indane, and the like. The groups may be optionally substituted.

The terms "alkoxyl" or "alkoxy" refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O— alkenyl, —O-alkynyl.

"Halo" or "Halogen", alone or in combination with any other term means halogens such as chloro (Cl), fluoro (F), bromo (Br), and iodo (I).

The term "heteroaryl" refers to an heteroaromatic carbocyclic group of 3 to 10 carbon atoms having a single ring (e.g. pyridine) or multiple rings (e.g. isoquinoline), or multiple condensed (fused) rings. Preferred heteroaryls include thiophene, pyrazole, thiazole, pyridine and the like. The groups may be optionally substituted.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms.

The term "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, the route of administration, and like factors within the knowledge and expertise of the attending physician The compounds described herein may contain one or more chiral centers and/or double bonds and therefore, may exist as stereoisomers, such as double-bond isomers (i.e., geometric isomers), regioisomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form and mixtures thereof. Accordingly, the chemical structures depicted herein encompass all possible tautomeric forms of the illustrated or identified compounds.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

The compounds discussed herein in many instances may have been named and/or checked with ACD/Name by ACD/Labs® and/or Electronic Lab Notebook by CambridgeSoft®.

The term "polymorphs" refers to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice.

The term "solvate", as used herein, refers to a crystal form of a substance which contains solvent.

The term "hydrate" refers to a solvate wherein the solvent is water.

The term "drug sensitive bacterium" as used herein is a bacterium which is not able to survive exposure to at least one drug.

The present disclosure relates to a compound of Formula I

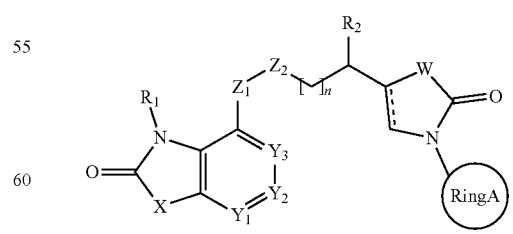

Formula I or its stereoisomers, pharmaceutically acceptable salts, complexes, hydrates, solvates, tautomers, polymorphs, racemic mixtures, optically active forms and pharmaceutically active derivative thereof, wherein
R₁ is selected from the group consisting of hydrogen, $C_{1-6}$ alkyl, $C_{2-6}$ alkenyl, and $C_3$-$C_6$ cycloalkyl, each of which is unsubstituted or substituted with 1 to 3 groups independently selected from halogen, hydroxy, amino, oxetane, —$OC_{1-6}$ alkyl, $C_{3-6}$ cycloalkylamino, $C_{1-6}$ alkylamino, or di($C_{1-6}$ alkyl)amino;

R₂ is selected from the group consisting of hydrogen, hydroxyl, and amino;

X is —NH, —$NC_{1-6}$ alkyl, O, or $CR_3R_4$;

R₃ and R₄ are independently selected from the group consisting of hydrogen, halogen, and $C_{1-6}$ alkyl;

Y₁ is N or $CR_5$;

R₅ is selected from the group consisting of hydrogen, halogen, cyano, —$OC_{1-6}$ alkyl, —$OC_{1-6}$ haloalkyl, and $C_{1-6}$ alkyl;

Y₂ is N or CH;

Y₃ is N or $CR_6$;

R₆ is selected from the group consisting of hydrogen, halogen, cyano, —$OC_{1-6}$ alkyl, $C_{1-6}$ alkyl, and —$OC_{1-6}$ haloalkyl;

Z₁ is NH when Z₂ is $C_{1-6}$ alkylene; or Z₁ is $C_{1-6}$ alkylene when Z₂ is NH;

n is 1 or 2;

W is $CH_2$ wherein dotted line (---) represents no bond; W is O when dotted line (---) represents either a bond or no bond;

Ring A is selected from the group consisting of

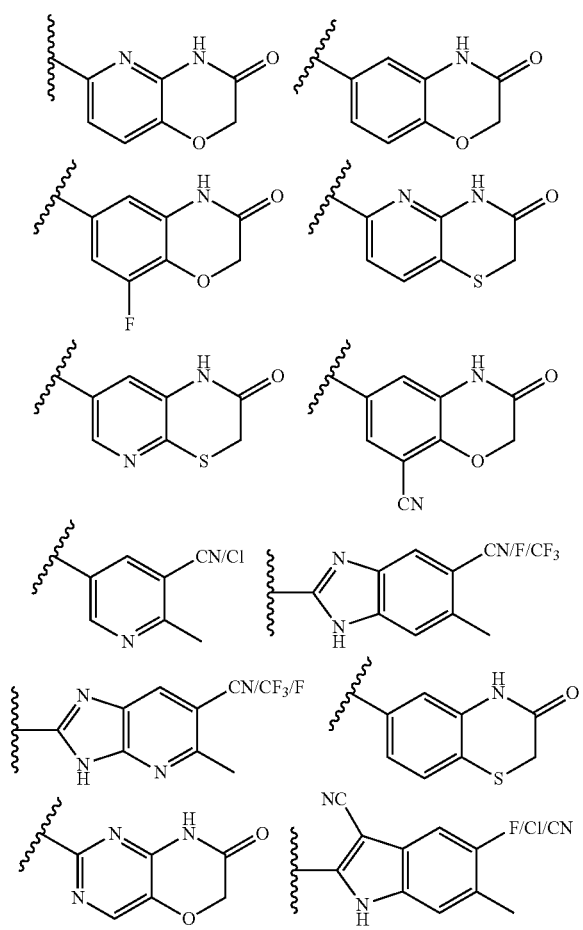

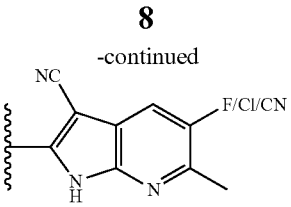

According to an embodiment, the present disclosure relates to a compound of Formula I

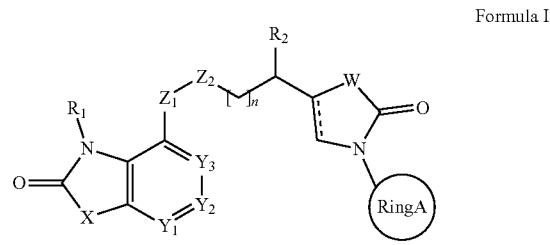

Formula I or its stereoisomers, pharmaceutically acceptable salts, complexes, hydrates, solvates, tautomers, polymorphs, racemic mixtures, optically active forms and pharmaceutically active derivative thereof, wherein
R₁ is selected from the group consisting of hydrogen, $C_{1-6}$ alkyl, $C_{2-6}$ alkenyl, and $C_{3-6}$ cycloalkyl, wherein alkyl is optionally substituted with 1 to 3 groups independently selected from fluorine, hydroxy, amino, oxetane, —$OC_1$ alkyl, $C_{3-6}$ cycloalkylamino, $C_{1-2}$ alkylamino, or di($C_{1-2}$ alkyl)amino;

R₂ is selected from the group consisting of hydrogen, hydroxyl, and amino;

X is —NH, —$NC_{1-6}$ alkyl, O, or $CR_3R_4$;

R₃ and R₄ are independently selected from the group consisting of hydrogen, halogen, and $C_{1-6}$ alkyl;

Y₁ is N or $CR_5$;

R₅ is selected from the group consisting of hydrogen, halogen, cyano, —$OC_{1-6}$ alkyl, —$OC_{1-6}$ haloalkyl, and $C_{1-6}$ alkyl;

Y₂ is N or CH;

Y₃ is N or $CR_6$;

R₆ is selected from the group consisting of hydrogen, fluorine, cyano, —$OC_{1-6}$ alkyl, —$C_{1-6}$ alkyl, and —$OC_{1-6}$ haloalkyl;

Z₁ is NH when Z₂ is $C_{1-6}$ alkylene; or Z₁ is $C_{1-6}$ alkylene when Z₂ is NH;

n is 1 or 2;

W is $CH_2$ wherein dotted line (---) represents no bond; W is O when dotted line (---) represents either a bond or no bond;

Ring A is selected from the group consisting of

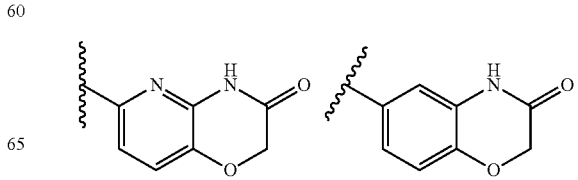

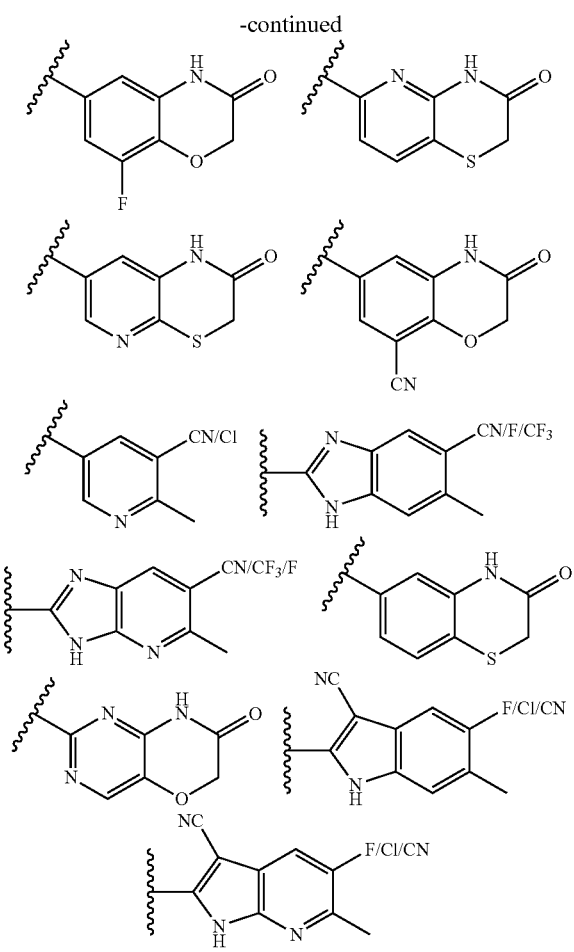

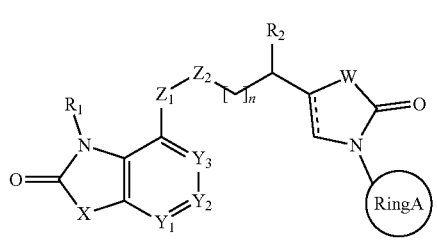

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein $Z_1$ is NH when $Z_2$ is $C_{1-6}$ alkylene; or $Z_1$ is $C_{1-6}$ alkylene or $C_{1-6}$ hydroxy alkylene when $Z_2$ is NH.

According to an embodiment, the present disclosure relates to a compound of Formula I Formula I or its stereoisomers, pharmaceutically acceptable salts, complexes, hydrates, solvates, tautomers, polymorphs, racemic mixtures, optically active forms and pharmaceutically active derivative thereof,
wherein
$R_1$ is selected from the group consisting of hydrogen, $C_{1-6}$ alkyl, $C_{2-6}$ alkenyl, and $C_{3-6}$ cycloalkyl, wherein alkyl is optionally substituted with 1 to 3 groups independently selected from fluorine, hydroxy, amino, oxetane, $-OC_1$ alkyl, $C_{3-6}$ cycloalkylamino, $C_{1-2}$ alkylamino, or di($C_{1-2}$ alkyl)amino;
$R_2$ is selected from the group consisting of hydrogen, hydroxyl, and amino;
X is $-NH$, $-NC_1$ alkyl, O, or $CR_3R_4$;
$R_3$ and $R_4$ are independently selected from the group consisting of hydrogen, fluorine, and $C_1$ alkyl;
$Y_1$ is N or $CR_5$;
$R_5$ is selected from the group consisting of hydrogen, fluorine, chlorine, cyano, $-OCH_3$, $-OCF_3$, $OCHF_2$, and $C_1$ alkyl;
$Y_2$ is N or CH;
$Y_3$ is N or $CR_6$;
$R_6$ is selected from the group consisting of hydrogen, fluorine, cyano, $-OCH_3$, $-OCHF_2$, and $-OCF_3$;
$Z_1$ is NH when $Z_2$ is $CH_2$; or $Z_1$ is $CH_2$, $CH_2CH_2$ or $CH(OH)CH_2$ when $Z_2$ is NH;
n is 1 or 2
W is O when dotted line ($---$) represents either a bond or no bond;
Ring A is selected from the group consisting of

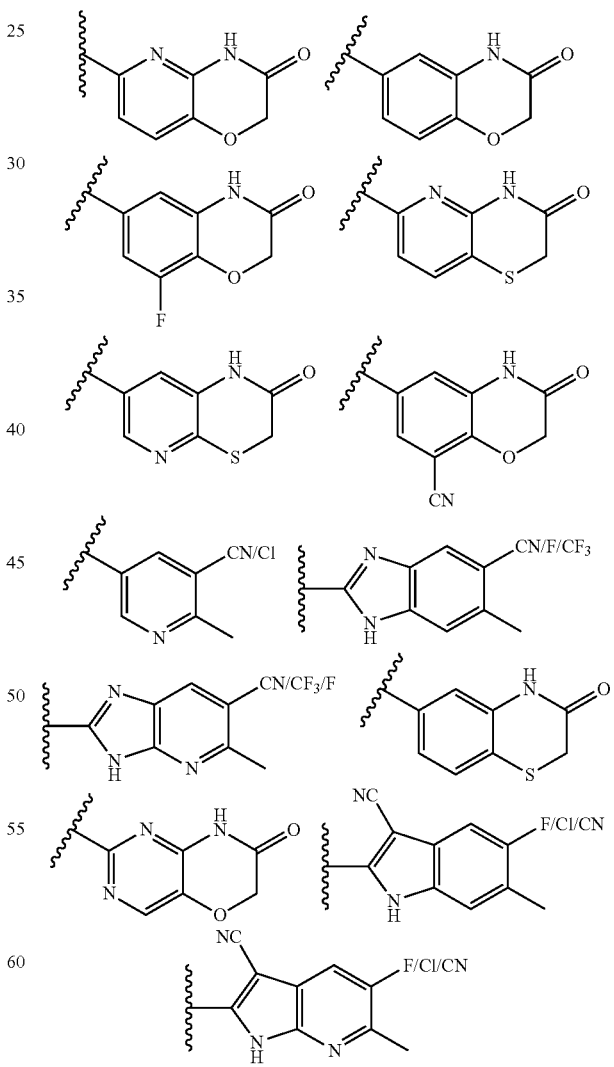

According to an embodiment, the present disclosure relates to a compound of Formula I Formula I

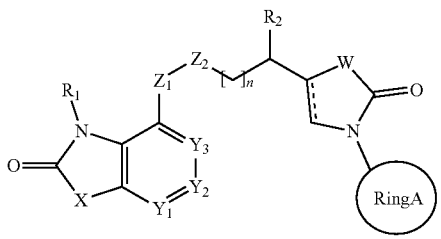

or its stereoisomers, pharmaceutically acceptable salts, complexes, hydrates, solvates, tautomers, polymorphs, racemic mixtures, optically active forms and pharmaceutically active derivative thereof,
wherein
$R_1$ is selected from the group consisting of hydrogen, $C_{1-6}$ alkyl, $C_{2-6}$ alkenyl, and $C_{3-6}$ cycloalkyl, wherein alkyl is optionally substituted with 1 to 3 groups independently selected from halogen, hydroxy, amino, oxetane, $-OC_{1-6}$ alkyl, $C_{3-6}$ cycloalkylamino, $C_{1-6}$ alkylamino, or di($C_{1-6}$ alkyl)amino;
$R_2$ is selected from the group consisting of hydrogen, hydroxyl, and amino;
X is $-NH$, $-NC_{1-6}$ alkyl, O, or $CR_3R_4$;
$R_3$ and $R_4$ are independently selected from the group consisting of hydrogen, halogen, and $C_{1-6}$ alkyl;
$Y_1$ is N or $CR_5$;
$R_5$ is selected from the group consisting of hydrogen, halogen, cyano, $-OC_{1-6}$ alkyl, $-OC_{1-6}$ haloalkyl, and $C_{1-6}$ alkyl;
$Y_2$ is N or CH;
$Y_3$ is N or $CR_6$;
$R_6$ is selected from the group consisting of hydrogen, halogen, cyano, $C_{1-6}$ alkyl, $-OC_{1-6}$ alkyl, and $-OC_{1-6}$ haloalkyl;
$Z_1$ is NH when $Z_2$ is $C_{1-6}$ alkylene; or $Z_1$ is $C_{1-6}$ alkylene when $Z_2$ is NH;
n is 1 or 2;
W is $CH_2$ wherein dotted line (---) represents no bond; W is O when dotted line (---) represents either a bond or no bond;
Ring A is selected from the group consisting of

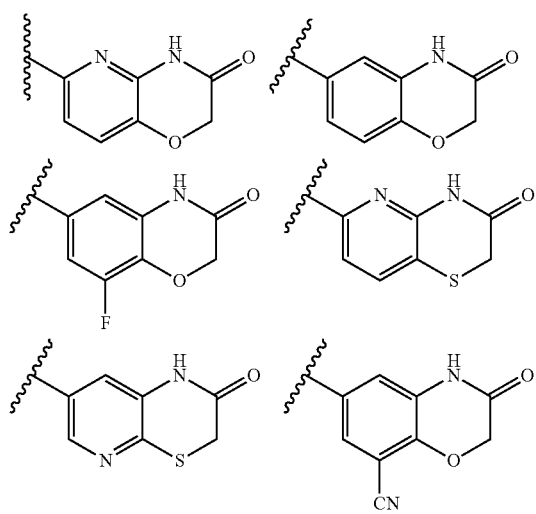

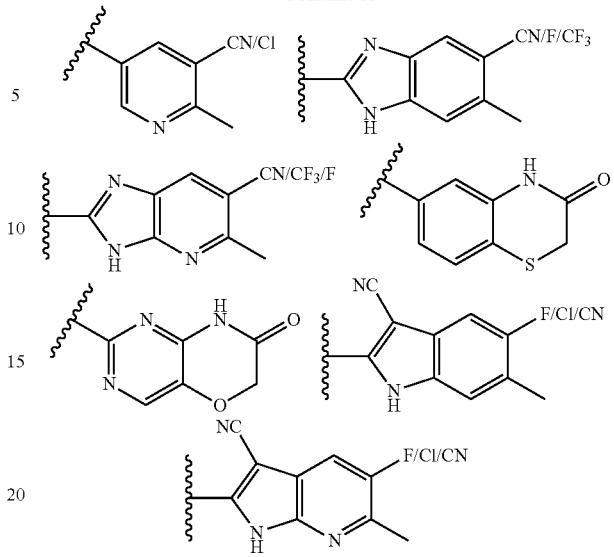

According to an embodiment, the present disclosure relates to a compound of Formula I Formula I

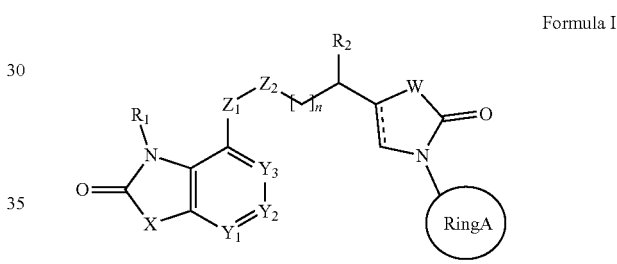

or its stereoisomers, pharmaceutically acceptable salts, complexes, hydrates, solvates, tautomers, polymorphs, racemic mixtures, optically active forms and pharmaceutically active derivative thereof,
wherein
$R_1$ is selected from the group consisting of hydrogen, $C_{1-6}$ alkyl, $C_{2-6}$ alkenyl, and $C_3$-$C_6$ cycloalkyl, wherein alkyl is optionally substituted with 1 to 3 groups independently selected from fluorine, hydroxy, amino, oxetane, $-OC_1$ alkyl, $C_3$-$C_6$ cycloalkylamino, $C_{1-2}$ alkylamino, or di($C_{1-2}$ alkyl)amino;
$R_2$ is selected from the group consisting of hydrogen, hydroxyl, and amino;
X is $-NH$, $-NC_{1-6}$ alkyl, O, or $CR_3R_4$;
$R_3$ and $R_4$ are independently selected from the group consisting of hydrogen, fluorine, and $C_1$ alkyl;
$Y_1$ is N or $CR_5$;
$R_5$ is selected from the group consisting of hydrogen, fluorine, chlorine, cyano, $-OCH_3$, $-OCF_3$, $OCHF_2$, and $C_1$ alkyl;
$Y_2$ is N or CH;
$Y_3$ is N or $CR_6$;
$R_6$ is selected from the group consisting of hydrogen, fluorine, cyano, $-OCH_3$, and $-OCF_3$;
$Z_1$ is NH when $Z_2$ is $CH_2$; or $Z_1$ is $CH_2$, $CH_2CH_2$ or $CH(OH)CH_2$ when $Z_2$ is NH;
n is 1 or 2;
W is $CH_2$ wherein dotted line (---) represents no bond; W is O when dotted line (---) represents either a bond or no bond;

Ring A is selected from the group consisting of

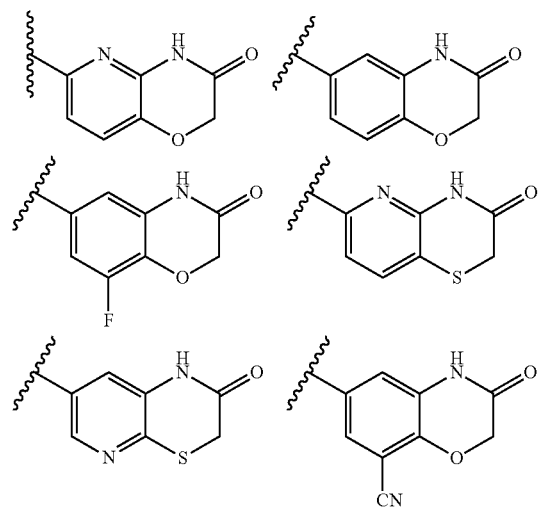

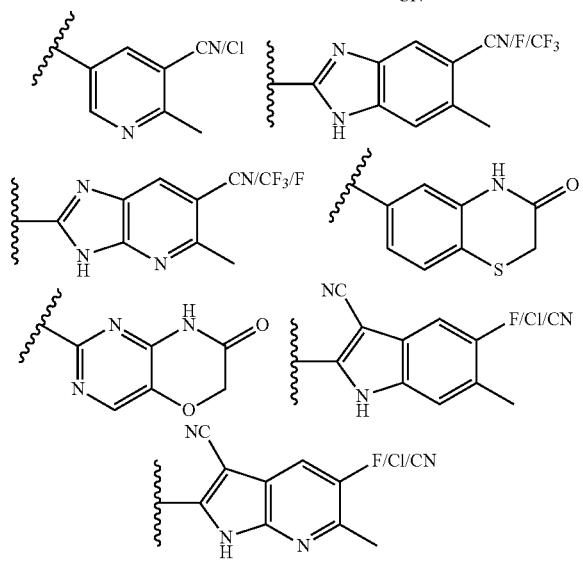

According to an embodiment, the present disclosure relates to a compound of Formula I

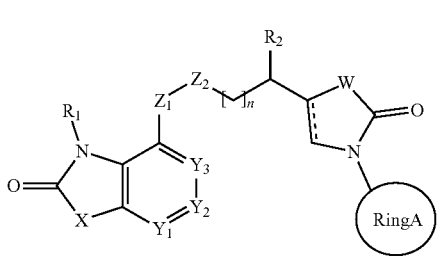

Formula I or its stereoisomers, pharmaceutically acceptable salts, complexes, hydrates, solvates, tautomers, polymorphs, racemic mixtures, optically active forms and pharmaceutically active derivative thereof,
wherein
$R_1$ is selected from the group consisting of hydrogen, $C_{1-4}$ alkyl, wherein alkyl is optionally substituted with 1 to 3 groups independently selected from fluorine, —$OC_1$ alkyl, amino, hydroxy, oxetane, $C_3$-$C_6$ cycloalkylamino, $C_{1-2}$ alkylamino, or di($C_{1-2}$ alkyl)amino;
$R_2$ is selected from the group consisting of hydrogen, amino, and hydroxyl;
X is O, —$NC_1$alkyl, or $CR_3R_4$;
$R_3$ and $R_4$ are independently selected from the group consisting of hydrogen, fluorine, and $C_1$ alkyl;
$Y_1$ is N or $CR_5$;
$R_5$ is selected from the group consisting of hydrogen, fluorine, chlorine, cyano, —$OC_1$ alkyl, —$OCF_3$, $OCHF_2$, and $C_1$ alkyl;
$Y_2$ is N or CH;
$Y_3$ is N or $CR_6$;
$R_6$ is selected from the group consisting of hydrogen, fluorine, cyano, —$OC_1$ alkyl, and —$OCF_3$;
$Z_1$ is NH when $Z_2$ is $CH_2$; or $Z_1$ is $CH_2$, $CH_2CH_2$ or $CH(OH)CH_2$ when $Z_2$ is NH;
n is 1 or 2;
W is $CH_2$ wherein dotted line (---) represents no bond; W is O when dotted line (---) represents either a bond or no bond;
Ring A is selected from the group consisting of:

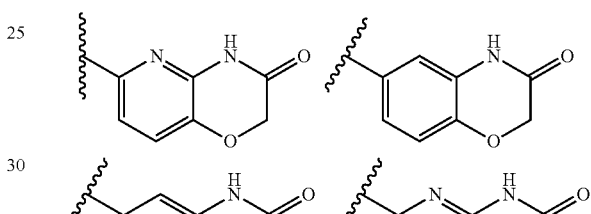

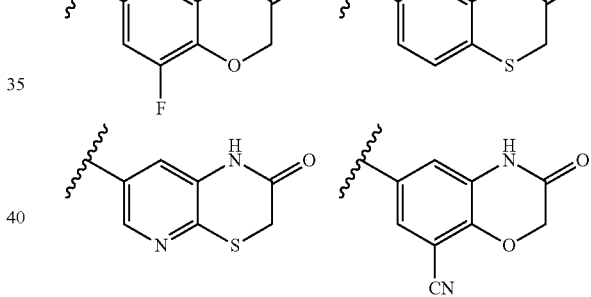

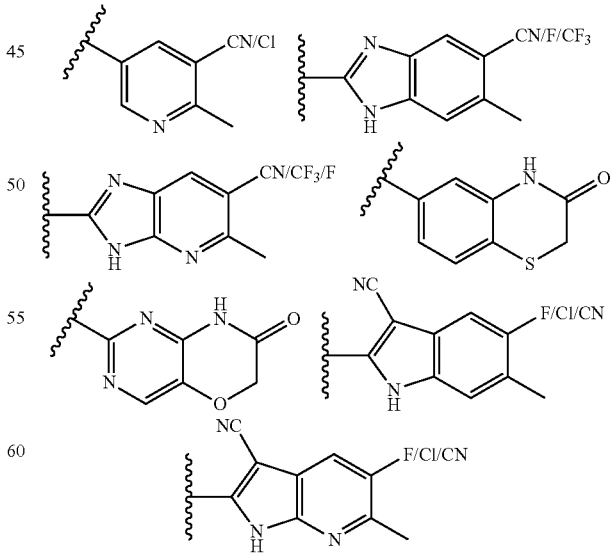

According to an embodiment, the present disclosure relates to a compound of Formula I

Formula I or its stereoisomers, pharmaceutically acceptable salts, complexes, hydrates, solvates, tautomers, polymorphs, racemic mixtures, optically active forms and pharmaceutically active derivative thereof, wherein
$R_1$ is selected from the group consisting of hydrogen, $C_{1-4}$ alkyl, wherein alkyl is optionally substituted with 1 to 3 groups independently selected from fluorine, —$OC_1$ alkyl, hydroxy, amino, oxetane, $C_{3-6}$ cycloalkylamino, $C_{1-2}$ alkylamino, or di($C_{1-2}$ alkyl)amino;
$R_2$ is selected from the group consisting of hydrogen, amino, and hydroxyl;
X is $CR_3R_4$;
$R_3$ and $R_4$ are independently selected from the group consisting of hydrogen, and $C_1$ alkyl;
$Y_1$ is N or $CR_5$;
$R_5$ is selected from the group consisting of hydrogen, fluorine, chlorine, cyano, —$OCH_3$, —$CF_3$, $OCHF_2$, and $C_1$ alkyl;
$Y_2$ is N or CH;
$Y_3$ is N or $CR_6$;
$R_6$ is selected from the group consisting of hydrogen, fluorine, cyano, —$OCH_3$, —$OCHF_2$, and —$OCF_3$;
$Z_1$ is NH when $Z_2$ is $CH_2$; or $Z_1$ is $CH_2$, $CH_2CH_2$ or $CH(OH)CH_2$ when $Z_2$ is NH;
n is 1 or 2;
W is $CH_2$ wherein dotted line (---) represents no bond; W is O when dotted line (---) represents either a bond or no bond;
Ring A is selected from the group consisting of According to an embodiment, the present disclosure relates to a compound of Formula I

Formula I or its stereoisomers, pharmaceutically acceptable salts, complexes, hydrates, solvates, tautomers, polymorphs, racemic mixtures, optically active forms and pharmaceutically active derivative thereof, wherein
$R_1$ is $C_1$ alkyl, wherein alkyl is optionally substituted with 1 to 3 groups independently selected from fluorine, —$OC_1$ alkyl, hydroxy, amino, oxetane, $C_{1-2}$ alkylamino, or di($C_{1-2}$ alkyl)amino;
$R_2$ is hydrogen;
X is $CR_3R_4$;
$R_3$ and $R_4$ are independently selected from the group consisting of hydrogen, and $C_1$ alkyl;
$Y_1$ is N or $CR_5$;
$R_5$ is hydrogen, $C_1$ alkyl, or cyano;
$Y_2$ is CH;
$Y_3$ is N or $CR_6$;
$R_6$ is selected from the group consisting of hydrogen, fluorine, cyano, —$OCH_3$, and —$OCF_3$;
$Z_1$ is NH when $Z_2$ is $CH_2$; or $Z_1$ is $CH_2$, $CH_2CH_2$ or $CH(OH)CH_2$ when $Z_2$ is NH;
n is 1 or 2;
W is $CH_2$ wherein dotted line (---) represents no bond; W is O when dotted line (---) represents either a bond or no bond;
Ring A is selected from the group consisting of -continued

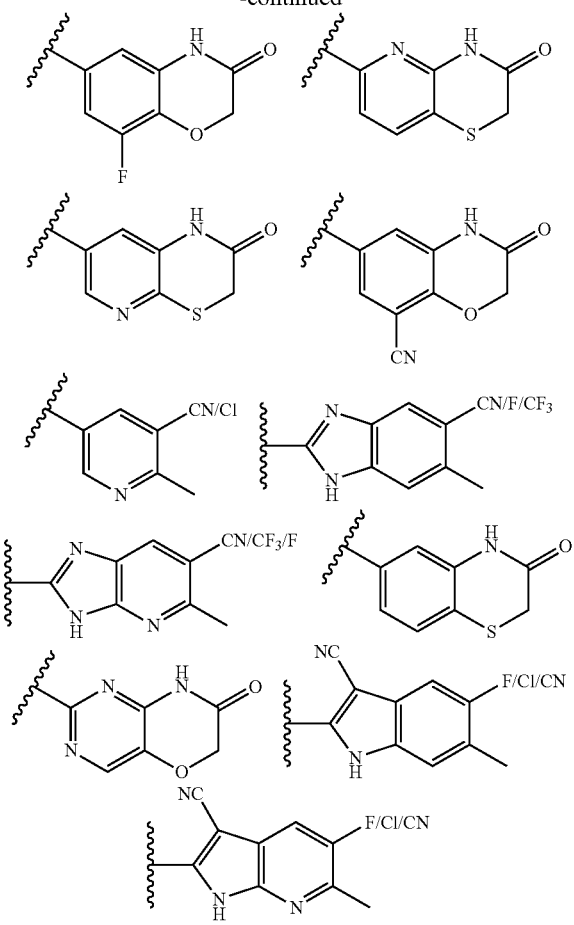

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein $R_1$ is $C_2$ alkyl, wherein alkyl is optionally substituted with 1 to 3 groups independently selected from fluorine, —$OC_1$ alkyl, amino, hydroxyl, $C_{1-2}$ alkylamino, or di($C_{1-2}$ alkyl) amino;

$R_2$ is hydrogen;

X is O or $CR_3R_4$;

$R_3$ and $R_4$ are independently selected from the group consisting of hydrogen, and $C_1$ alkyl;

$Y_1$ is N or $CR_5$;

$R_5$ is selected from the group consisting of hydrogen, $C_1$ alkyl, and cyano;

$Y_2$ is CH;

$Y_3$ is N or $CR_6$;

$R_6$ is selected from the group consisting of hydrogen, fluorine, cyano, —$OCH_3$, $OCHF_2$ and —$OCF_3$;

$Z_1$ is NH when $Z_2$ is $CH_2$; or $Z_1$ is $CH_2$, $CH_2CH_2$ or $CH(OH)CH_2$ when $Z_2$ is NH;

n is 1 or 2;

W is O when dotted line ( ---- ) represents either a bond or no bond; ----

Ring A is selected from the group consisting of

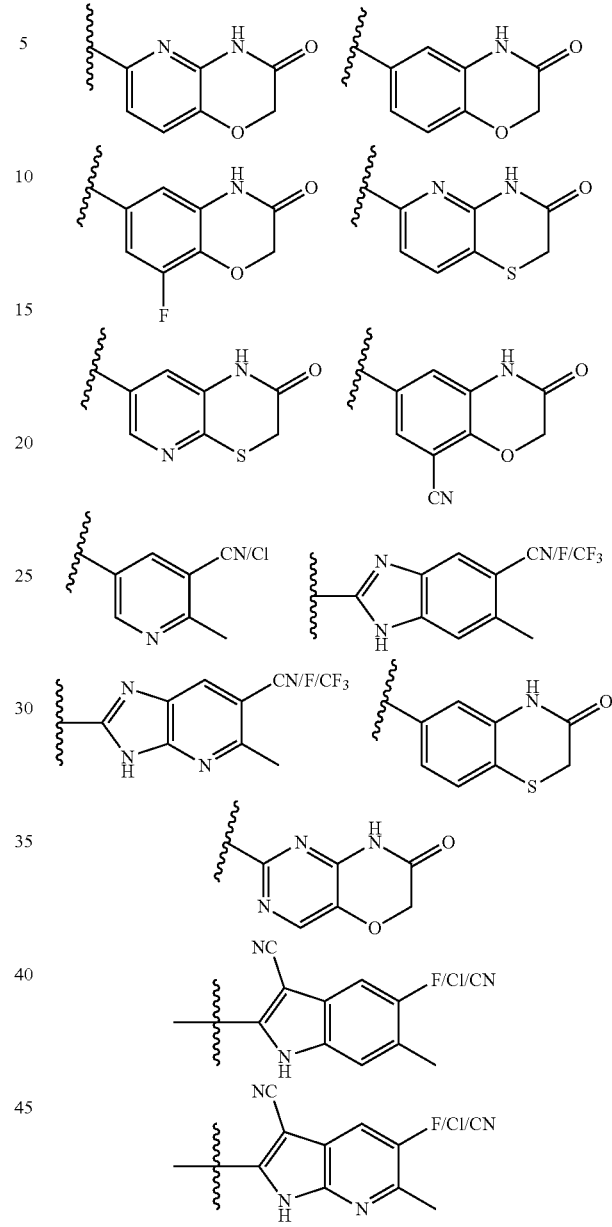

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein $R_1$ is $C_1$ alkyl, wherein alkyl is optionally substituted with 1 to 3 groups independently selected from fluorine, —$OC_1$ alkyl, amino, hydroxyl, $C_{1-2}$ alkylamino, or di($C_{1-2}$ alkyl) amino;

$R_2$ is hydrogen;

X is O;

$R_3$ and $R_4$ are independently selected from the group consisting of hydrogen, and $C_1$ alkyl;

$Y_1$ is N or $CR_5$;

$R_5$ is selected from the group consisting of hydrogen, $C_1$ alkyl, and cyano;

19

$Y_2$ is CH;

$Y_3$ is N or $CR_6$;

$R_6$ is selected from the group consisting of hydrogen, fluorine, cyano, —$OCH_3$, $OCHF_2$ and —$OCF_3$;

$Z_1$ is NH when $Z_2$ is $CH_2$; or $Z_1$ is $CH_2$, $CH_2CH_2$ or $CH(OH)CH_2$ when $Z_2$ is NH;

n is 1 or 2;

W is O when dotted line ( --- ) represents either a bond or no bond;

Ring A is selected from the group consisting of

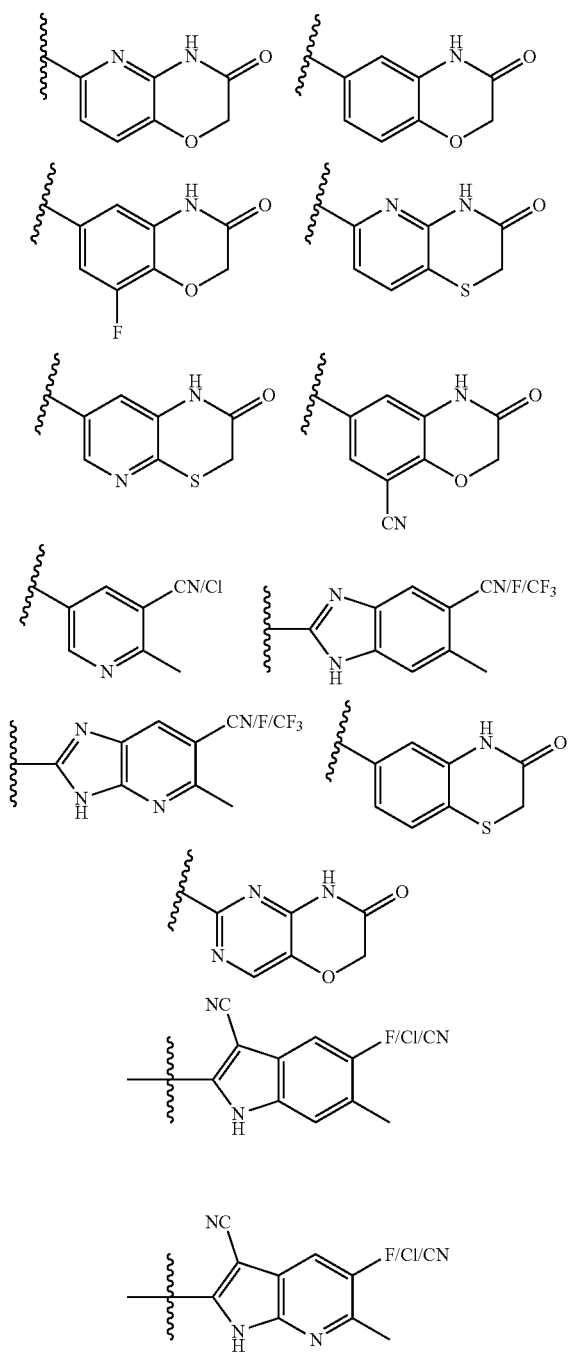

20

According to an embodiment, the present disclosure relates to a compound of Formula I

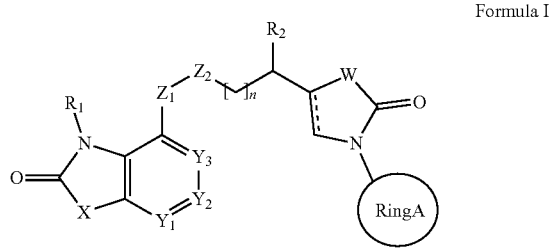

Formula I or its stereoisomers, pharmaceutically acceptable salts, complexes, hydrates, solvates, tautomers, polymorphs, racemic mixtures, optically active forms and pharmaceutically active derivative thereof, wherein $R_1$ is $C_{1-4}$ alkyl;

$R_2$ is hydrogen;

X is O or $CR_3R_4$;

$R_3$ and $R_4$ are independently selected from the group consisting of hydrogen, and $C_1$ alkyl;

$Y_1$ is N or $CR_5$;

$R_5$ is hydrogen;

$Y_2$ is CH;

$Y_3$ is N or $CR_6$;

$R_6$ is selected from the group consisting of hydrogen, fluorine, cyano, —$OCH_3$, and —$OCF_3$;

$Z_1$ is NH when $Z_2$ is $CH_2$; or $Z_1$ is $CH_2$, $CH_2CH_2$ or $CH(OH)CH_2$ when $Z_2$ is NH;

n is 1 or 2;

W is O when dotted line ( --- ) represents either a bond or no bond;

Ring A is selected from the group consisting of

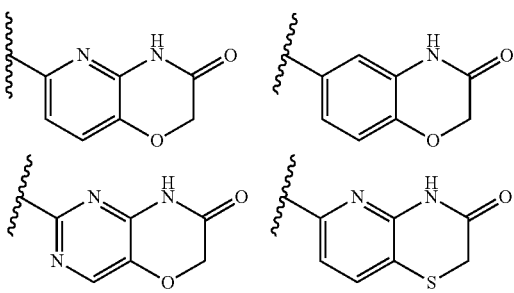

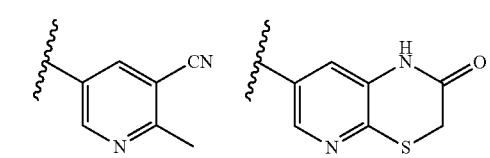

According to an embodiment, the present disclosure relates to a compound of Formula I

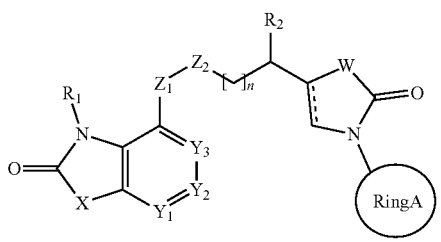

Formula I or its stereoisomers, pharmaceutically acceptable salts, complexes, hydrates, solvates, tautomers, polymorphs, racemic mixtures, optically active forms and pharmaceutically active derivative thereof, wherein
$R_1$ is selected from the group consisting of methyl, ethyl, isopropyl;
$R_2$ is hydrogen;
X is $CR_3R_4$;
$R_3$ and $R_4$ are independently selected from the group consisting of hydrogen and $C_1$ alkyl;
$Y_1$ is N or $CR_5$;
$R_5$ is hydrogen, $CH_3$, CN;
$Y_2$ is CH;
$Y_3$ is $CR_6$;
$R_6$ is hydrogen, fluorine, cyano, —$OCH_3$, and —$OCF_3$;
$Z_1$ is NH when $Z_2$ is $CH_2$; or $Z_1$ is $CH_2CH_2$ or $CH(OH)CH_2$ when $Z_2$ is NH;
n is 1 or 2;
W is O when dotted line (---) represents either a bond or no bond;
Ring A is selected from the group consisting of

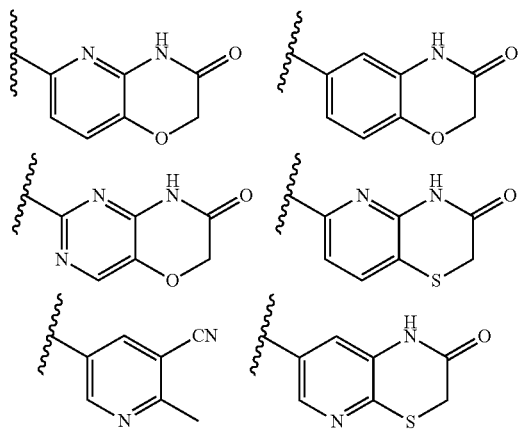

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein
$R_1$ is selected from the group consisting of $C_{1-3}$ alkyl, wherein alkyl is optionally substituted with 1 to 3 groups independently selected from fluorine, —$OC_1$ alkyl, amino, hydroxy, $C_{1-2}$ alkylamino, or di($C_{1-2}$ alkyl)amino;
$R_2$ is hydrogen;
X is $CR_3R_4$;
$R_3$ and $R_4$ are independently selected from the group consisting of hydrogen and $C_1$ alkyl;
$Y_1$ is N or $CR_5$;
$R_5$ is selected from the group consisting of hydrogen, $CH_3$, and CN;
$Y_2$ is CH;
$Y_3$ is N or $CR_6$;
$R_6$ is selected from the group consisting of hydrogen, fluorine, cyano, —$OCH_3$, and —$OCF_3$;
$Z_1$ is NH when $Z_2$ is $CH_2$; or $Z_1$ is $CH_2$, $CH_2CH_2$ or $CH(OH)CH_2$ when $Z_2$ is NH;
n is 1 or 2;
W is O when dotted line (---) represents either a bond or no bond;
Ring A is selected from the group consisting of

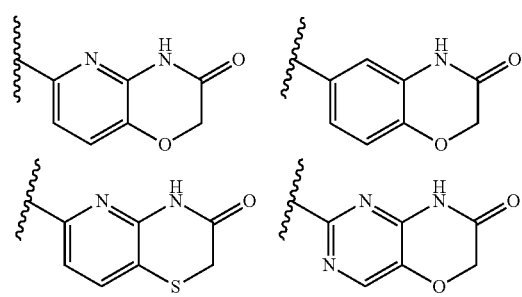

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein
$R_1$ is selected from the group consisting of hydrogen, $C_{1-6}$ alkyl, $C_{2-6}$ alkenyl, and $C_3$-$C_6$ cycloalkyl, wherein alkyl is optionally substituted with 1 to 3 groups independently selected from fluorine, hydroxy, amino, oxetane, —$OC_1$ alkyl, $C_3$-$C_6$ cycloalkylamino, $C_{1-2}$ alkylamino, or di($C_{1-2}$ alkyl)amino;
$R_2$ is selected from the group consisting of hydrogen, hydroxyl, and amino;
X is —NH, —$NC_{1-6}$ alkyl, O, or $CR_3R_4$;
$R_3$ and $R_4$ are independently selected from the group consisting of hydrogen, halogen, and $C_{1-6}$ alkyl;
$Y_1$ is N or $CR_5$;
$R_5$ is selected from the group consisting of hydrogen, halogen, cyano, —$OC_{1-6}$ alkyl, —$OC_{1-6}$ haloalkyl, and $C_{1-6}$ alkyl;
$Y_2$ is N or CH;
$Y_3$ is N or $CR_6$;
$R_6$ is selected from the group consisting of hydrogen, fluorine, cyano, —$OC_{1-6}$ alkyl, —$C_{1-6}$ alkyl, and —$OC_{1-6}$ haloalkyl;
$Z_1$ is NH when $Z_2$ is $C_{1-6}$ alkylene; or $Z_1$ is $C_{1-6}$alkylene when $Z_2$ is NH;
n is 1 or 2
W is $CH_2$ wherein dotted line (---) represents no bond; W is O when dotted line (---) represents either a bond or no bond;
Ring A is selected from the group consisting of

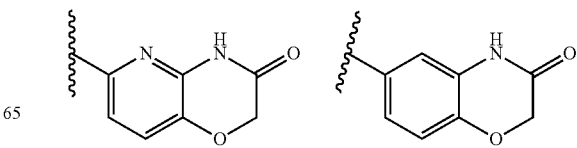

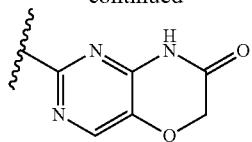

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein X is NH, —N(CH$_3$), O, CH$_2$, CH—F, CH—CH$_3$, CF$_2$ or C(CH$_3$)$_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein X is O, —CH, C(F)$_2$, or C—(CH$_3$)$_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein X is —CH$_2$, or C—(CH$_3$)$_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein R$_2$ is selected from H, hydroxy or amino.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein R$_2$ is H.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein Z$_1$ and Z$_2$ is independently selected from —NH—, —CH$_2$, or CH$_2$CH$_2$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein Y$_2$ is N or CH.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein Y$_2$ is CH.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein Y$_1$ is N, CH, CF, CCl, C—CN, C—OCH$_3$, C—OCF$_3$, C—OCHF$_2$, or C—CH$_3$.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein Y$_1$ is CH.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein Y$_3$ is N, —CH, —CF, —C(CN), —C(OCH$_3$), —C(OCF$_3$), or —C(OCHF$_2$).

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein Y$_3$ is —CH, or —CF.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein n is 1 or 2

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, which is selected from a group consisting of:

6-(5-(2-(((1-Methyl-2-oxoindolin-7-yl)methyl)amino)ethyl)-2-oxooxazolidin-3-yl)-2H-pyrido[3,2-b][1,4]oxazin-3(4H)-one, 6-(5-(2-(((6-Fluoro-1-methyl-2-oxoindolin-7-yl)methyl)amino)ethyl)-2-oxooxazolidin-3-yl)-2H-pyrido[3,2-b][1,4]oxazin-3 (4H)-one, 6-(5-(2-(((6-Fluoro-1-methyl-2-oxoindolin-7-yl)methyl)amino)ethyl)-2-oxooxazolidin-3-yl)-2H-benzo[b][1,4]oxazin-3(4H)-one, 6-(5-(2-(((6-Fluoro-1,3,3-trimethyl-2-oxoindolin-7-yl)methyl)amino)ethyl)-2-oxooxazolidin-3-yl)-2H-pyrido[3,2-b][1,4]oxazin-3(4H)-one, 5-(5-(2-(((6-Fluoro-1-methyl-2-oxoindolin-7-yl)methyl)amino)ethyl)-2-oxooxazolidin-3-yl)-2-methylnicotinonitrile, 6-(5-(3-(((6-Fluoro-1-methyl-2-oxoindolin-7-yl)methyl)amino)propyl)-2-oxooxazolidin-3-yl)-2H-pyrido[3,2-b][1,4]oxazin-3(4H)-one, 6-(5-(2-(((1-Ethyl-6-fluoro-2-oxoindolin-7-yl)methyl)amino)ethyl)-2-oxooxazolidin-3-yl)-2H-pyrido[3,2-b][1,4]oxazin-3 (4H)-one, 6-(5-(3-(((1-Ethyl-6-fluoro-2-oxoindolin-7-yl)methyl)amino)propyl)-2-oxooxazolidin-3-yl)-2H-pyrido[3,2-b][1,4]oxazin-3 (4H)-one, 6-(5-(3-(((6-Fluoro-1-methyl-2-oxoindolin-7-yl)methyl)amino)propyl)-2-oxooxazolidin-3-yl)-2H-pyrido[3,2-b][1,4]oxazin-3(4H)-one (Enantiomer1), 6-(5-(3-(((6-Fluoro-1-methyl-2-oxoindolin-7-yl)methyl)amino)propyl)-2-oxooxazolidin-3-yl)-2H-pyrido[3,2-b][1,4]oxazin-3(4H)-one (Enantiomer2), 6-(5-(2-((2-(6-Fluoro-1-methyl-2-oxoindolin-7-yl)ethyl)amino)ethyl)-2-oxooxazolidin-3-yl)-2H-pyrido[3,2-b][1,4]oxazin-3 (4H)-one, 6-(5-(3-(((6-Fluoro-1-methyl-2-oxoindolin-7-yl)methyl)amino)propyl)-2-oxooxazolidin-3-yl)-2H-benzo[b][1,4]oxazin-3(4H)-one, 6-(5-(2-((2-(6-Fluoro-1-methyl-2-oxoindolin-7-yl)ethyl) amino)ethyl)-2-oxooxazolidin-3-yl)-2H-pyrido[3,2-b][1,4]oxazin-3 (4H)-one (Enantiomer1), 6-(5-(2-((2-(6-Fluoro-1-methyl-2-oxoindolin-7-yl)ethyl) amino)ethyl)-2-oxooxazolidin-3-yl)-2H-pyrido[3,2-b][1,4]oxazin-3 (4H)-one (Enantiomer2), 6-(5-(2-((2-(6-Fluoro-1-methyl-2-oxoindolin-7-yl)-2-hydroxyethyl)amino)ethyl)-2-oxooxazolidin-3-yl)-2H-pyrido[3,2-b][1,4]oxazin-3(4H)-one, 6-(5-(2-((2-(5-Fluoro-3-methyl-2-oxo-2,3-dihydrobenzo[d]oxazol-4-yl)ethyl)amino)ethyl)-2-oxooxazolidin-3-yl)-2H-pyrido[3,2-b][1,4]oxazin-3 (4H)-one, and 6-(5-(3-(((6-Fluoro-1-methyl-2-oxo-2,3-dihydro-1H-pyrrolo[3,2-b]pyridin-7-yl)methyl)amino)propyl)-2-oxooxazolidin-3-yl)-2H-pyrido[3,2-b][1,4]oxazin-3(4H)-one.

According to an embodiment, the present disclosure relates to a process of preparation of compound of Formula I or its stereoisomers, pharmaceutically acceptable salts, complexes, hydrates, solvates, tautomers, polymorphs, racemic mixtures, optically active forms and pharmaceutically active derivative thereof.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, for use in killing or inhibiting the growth of a microorganism selected from the group consisting of bacteria, virus, fungi and protozoa.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, for use in killing or inhibiting the growth of Gram-positive and Gram-negative bacteria.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, for use in killing or inhibiting the growth of drug sensitive and drug resistance bacterium selected from a group consisting of *Escherichia coli, Salmonella typhi, Salmonella paratyphi, Salmonella typhimurium, Salmonella enteritidis, Shigella dysenteriae, Shigella flexneri, Shigella boydii, Shigella sonnei, Staphylococcus aureus, Staphylococcus epidermidis, Streptococcus pneumoniae, Streptococcus pygenes, Stenotrophomonas maltophilia, Haemophilus influenza, Klebsiella pneumoniae, Legionella pneumophila, Mycoplasma pneumoniae, Acinetobacter baumannii, Acinetobacter haemolyticus, Acinetobacter junii, Acinetobacter lwoffi, Burkholderia cepacia, Chlamydophila pneumoniae, Clostridium difficili, Pseudomonas aeruginosa, Enterobacter aerogenes, Enterobacter cloacae, Moraxella catarrhalis, Enterococcus faecium, Enterococcus faecalis, Enterococcus faeciu, Neisseria gonorrhoeae, Neisseria meningitides*, or any combinations thereof.

According to an embodiment, the present disclosure relates to use of a compound of Formula I or its stereoisomers, pharmaceutically acceptable salts, complexes, hydrates, solvates, tautomers, polymorphs, racemic mixtures, optically active forms and pharmaceutically active derivative thereof, in killing or inhibiting the growth of a microorganism selected from the group consisting of bacteria, virus, fungi and protozoa.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, for use in treating a disease or condition in a patient wherein said disease or condition is caused by a microorganism selected from the group consisting of Gran negative and Gram positive pathogens.

According to an embodiment, the present disclosure relates to use of a compound of Formula I or its stereoisomers, pharmaceutically acceptable salts, complexes, hydrates, solvates, tautomers, polymorphs, racemic mixtures, optically active forms and pharmaceutically active derivative thereof, in treating disease or condition in a patient, wherein said disease or condition is caused by a microorganism selected from the group consisting of Gram negative and Gram positive pathogens. The patient is a typically a mammal, preferably a human.

According to an embodiment, the present disclosure relates to a method of treating a disease or condition in a patent, said method comprising administering to a patient a compound of Formula I, or its stereoisomers, pharmaceutically acceptable salts, complexes, hydrates, solvates, tautomers, polymorphs, racemic mixtures, optically active forms and pharmaceutically active derivative thereof, wherein said disease or condition is caused by microorganism selected from the group consisting of Gram negative and Gram positive pathogens.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, for use as a medicament.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, for use in the preparation of medicaments for inhibiting microbial growth.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, for use in the preparation of medicaments for inhibiting bacterial growth.

According to an embodiment, the present disclosure relates to medicaments that include a compound of Formula I, or an addition salt of the compound of formula I with a pharmaceutically acceptable acid or base. These medicaments find their use in therapeutics, especially in the treatment of bacterial infection caused by both drug sensitive and drug resistance bacterium including quinolone resistance belonging to Gram positive and Gram negative species; especially of those caused by *Escherichia coli, Staphylococcus aureus, Klebsiella pneumoniae, Acinetobacter baumannii, Pseudomonas aeruginosa, Clostridium difficili, Neisseria gonorrhoeae*, and *Enterococcus faecalis*.

According to an embodiment, the present disclosure relates to the use of a compound of Formula I, or its stereoisomers, pharmaceutically acceptable salts, complexes, hydrates, solvates, tautomers, polymorphs, racemic mixtures, optically active forms and pharmaceutically active derivative thereof, in the manufacture of a medicament for the treatment of an infection caused by bacterial species in a warm-blooded animal, such as man.

According to an embodiment, the present disclosure relates to the use of a compound of Formula I, or its stereoisomers, pharmaceutically acceptable salts, complexes, hydrates, solvates, tautomers, polymorphs, racemic mixtures, optically active forms and pharmaceutically active derivative thereof, in the manufacture of a medicament for the production of an antibacterial effect in a warm-blooded animal such as man.

According to an embodiment, the present disclosure relates to a method for treating bacterial infections caused by bacterial species in a warm-blooded animal such as man, said method including administering to said animal an effective amount of a compound of formula I, or a pharmaceutically acceptable salt thereof.

According to an embodiment, the present disclosure relates to a method for producing an antibacterial effect in a warm-blooded animal such as man, said method including administering to said animal an effective amount of a compound of formula I, or a pharmaceutically acceptable salt thereof.

According to an embodiment, the present disclosure relates to a compound of Formula I, or a pharmaceutically acceptable salt thereof, for use in the treatment and/or prophylaxis of bacterial infections in a warm-blooded animal, such as man.

According to an embodiment, the present disclosure relates to a compound of Formula I, or a pharmaceutically acceptable salt thereof, for the therapeutic and prophylactic treatment of mammals including humans, in particular in treating bacterial infections caused by bacterial species, is normally formulated in accordance with standard pharmaceutical practice as a pharmaceutical composition.

According to an embodiment, the present disclosure relates to a pharmaceutical composition including a compound of Formula I, or its stereoisomers, pharmaceutically acceptable salts, complexes, hydrates, solvates, tautomers, polymorphs, racemic mixtures, optically active forms and pharmaceutically active derivative thereof, and at least one pharmaceutically acceptable carrier, diluent, or excipient.

According to an embodiment, the present disclosure relates to the use of a pharmaceutical composition including a compound of Formula I, or its stereoisomers, pharmaceutically acceptable salts, complexes, hydrates, solvates, tautomers, polymorphs, racemic mixtures, optically active forms and pharmaceutically active derivative thereof, in the manufacture of a medicament for the treatment of a bacterial infection caused by bacterial species in a warm-blooded animal such as man.

According to an embodiment, the present disclosure relates to the use of a pharmaceutical composition including a compound of Formula I, or its stereoisomers, pharmaceutically acceptable salts, complexes, hydrates, solvates, tautomers, polymorphs, racemic mixtures, optically active forms and pharmaceutically active derivative thereof, in the manufacture of a medicament for the production of an antibacterial effect in a warm-blooded animal such as man.

According to an embodiment, the present disclosure relates to a pharmaceutical composition comprising a compound of formula I or its stereoisomers, pharmaceutically acceptable salts, complexes, hydrates, solvates, tautomers, polymorphs, racemic mixtures, optically active forms and pharmaceutically active derivative thereof together with a pharmaceutically acceptable carrier, and in combination with at least one antibiotic.

According to an embodiment, the present disclosure relates to a method for treating infection caused by bacterial species in a warm-blooded animal such as man, said method including administering to said animal an effective amount of a pharmaceutical composition including a compound of Formula I, or its stereoisomers, pharmaceutically acceptable salts, complexes, hydrates, solvates, tautomers, polymorphs, racemic mixtures, optically active forms and pharmaceutically active derivative thereof.

According to an embodiment, the present disclosure relates to a method for producing an antibacterial effect in a warm-blooded animal such as man, said method including administering to said animal an effective amount of a pharmaceutical composition including a compound of Formula I, or its stereoisomers, pharmaceutically acceptable salts, complexes, hydrates, solvates, tautomers, polymorphs, racemic mixtures, optically active forms and pharmaceutically active derivative thereof.

According to an embodiment, the present disclosure relates to a pharmaceutical composition comprising a compound of Formula I or its stereoisomers, pharmaceutically acceptable salts, complexes, hydrates, solvates, tautomers, polymorphs, racemic mixtures, optically active forms and pharmaceutically active derivative thereof, together with a pharmaceutically acceptable carrier, optionally in combination with one or more other pharmaceutical compositions.

According to an embodiment, the present disclosure relates to a pharmaceutical composition comprising a compound of Formula I, or its stereoisomers, pharmaceutically acceptable salts, complexes, hydrates, solvates, tautomers, polymorphs, racemic mixtures, optically active forms and pharmaceutically active derivative thereof, and a pharmaceutically acceptable diluent or carrier.

According to an embodiment, the present disclosure relates to a composition comprising a compound of Formula I, or its stereoisomers, pharmaceutically acceptable salts, complexes, hydrates, solvates, tautomers, polymorphs, racemic mixtures, optically active forms and pharmaceutically active derivative thereof, and a carrier.

The language "pharmaceutically acceptable" includes compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula I may form stable pharmaceutically acceptable acid or base salts, and in such cases administration of a compound as a salt may be appropriate. Examples of acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Examples of base salts include ammonium salts; alkali metal salts such as sodium, lithium and potassium salts; alkaline earth metal salts such as aluminum, calcium and magnesium salts; salts with organic bases such as dicyclohexylamine salts and N10 methyl-D-glucamine; and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates such as dimethyl, diethyl, dibutyl; diamyl sulfates; long chain halides such as decyl, lauryl, myristyl and stearyl halides; arylalkyl halides such as benzyl bromide and others. Non-toxic physiologically acceptable salts are preferred, although other salts may be useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The present disclosure relates to a process of preparation of a composition comprising a compound of Formula I or its stereoisomers, pharmaceutically acceptable salts, complexes, hydrates, solvates, tautomers, polymorphs, racemic mixtures, optically active forms and pharmaceutically active derivative thereof together with a carrier.

The present disclosure relates to a process of preparation of pharmaceutical composition comprising a compound of Formula I or its stereoisomers, pharmaceutically acceptable salts, complexes, hydrates, solvates, tautomers, polymorphs, racemic mixtures, optically active forms and pharmaceutically active derivative thereof, together with a pharmaceutically acceptable carrier, optionally in combination with one or more other pharmaceutical compositions.

The compositions of the present disclosure may be obtained by conventional procedures using conventional pharmaceutical excipients well known in the art. Thus, compositions intended for oral use may contain, for example, one or more colouring, sweetening, flavouring and/or preservative agents Suitable pharmaceutically acceptable excipients for a tablet formulation include, for example, inert diluents such as lactose, sodium carbonate, calcium phosphate or calcium carbonate; granulating and disintegrating agents such as corn starch or algenic acid; binding agents such as starch; lubricating agents such as magnesium stearate, stearic acid or talc; preservative agents such as ethyl or propyl p-hydroxybenzoate; and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents or procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or oil such as peanut oil, liquid paraffin, or olive oil.

Aqueous suspensions generally contain the active ingredient in finely powdered form or in the form of nano or micronized particles together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives such as ethyl or propyl p-hydroxybenzoate; anti-oxidants such as ascorbic acid); coloring agents; flavoring agents; and/or sweetening agents such as sucrose, saccharine or aspartame.

Oily suspensions may be formulated by suspending the active ingredient in a vegetable oil such as *arachis* oil, olive oil, sesame oil or coconut oil or in a mineral oil such as liquid paraffin. The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the disclosure may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

Compositions for administration may also be formulated as a liposome preparation. The liposome preparation can comprise liposomes which penetrate the cells of interest or stratum corneum, and fuse with the cell membrane, resulting in delivery of the contents of the liposome into the cell. Other suitable formulations can employ niosomes. Niosomes are lipid vesicles similar to liposomes, with membrane consisting largely of nonoinic lipids, some forms of which are effective for transporting compounds across the stratum corneum.

Compositions for administration may also be formulated as a depot preparation, which may be administered by implantation or by intramuscular injection. The compositions may be formulated with suitable polymeric or hydrophobic material (as an emulsion in acceptable oil), ion exchange resins, or sparingly soluble derivatives.

The compound of the present disclosure can also be administered in sustained release forms or from sustained release drug delivery systems.

For further information on formulation, drug delivery as well as processing techniques the reader is referred to Remington's Pharmaceutical Sciences (21$^{st}$ Edition, 2005, University of the sciences in Philadelphia, Lippincott William & Wilkins)

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 4 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990 and Remington's Pharmaceutical Sciences (21$^{st}$ Edition, 2005, University of the sciences in Philadelphia, Lippincott William & Wilkins).

As stated above the size of the dose required for the therapeutic or prophylactic treatment of a particular disease state will necessarily be varied depending on the host treated, the route of administration and the severity of the illness being treated. Preferably a daily dose in the range of 1-25 mg/kg is employed. Accordingly, the optimum dosage may be determined by the practitioner who is treating any particular patient.

In any of the pharmaceutical compositions, processes, methods, uses, medicaments, and manufacturing features mentioned herein, any of the alternate aspects of the compounds of the disclosure described herein also apply.

The compounds disclosed herein may be applied as a sole therapy or may involve, in addition to a compound of the disclosure, one or more other substances and/or treatments. Such conjoint treatment may be achieved by way of the simultaneous, sequential or separate administration of the individual components of the treatment. Where the administration is sequential or separate, the delay in administering the second component should not be such as to lose the beneficial effect of the combination. Suitable classes and substances may be selected from one or more of the following: i) other antibacterial agents for example macrolides e.g. erythromycin, azithromycin or clarithromycin; quinolones e.g. ciprofloxacin or levofloxacin; B lactams e.g. penicillins e.g. amoxicillin or piperacillin; cephalosporins e.g. ceftriaxone or ceftazidime; carbapenems, e.g. meropenem or imipenem etc; aminoglycosides e.g. gentamicin or tobramycin; or oxazolidinones; and/or ii) anti-infective agents for example, an antifungal triazole e.g. or amphotericin; and/or iii) biological protein therapeutics for example antibodies, cytokines, bactericidal/permeability increasing protein (BPI) products; and/or iv) one or more antibacterial agents useful in the treatment of *Mycobacterium tuberculosis* such as one or more of rifampicin, isoniazid, pyrizinamide, ethambutol, quinolones e.g. moxifloxacin or gatifloxacin, streptomycin and/or v) efflux pump inhibitors.

According to an embodiment, the present disclosure relates to a compound of the Formula I, or a pharmaceutically acceptable salt thereof and a chemotherapeutic agent selected from: i) one or more additional antibacterial agents; and/or ii) one or more anti-infective agents; and/or iii) biological protein therapeutics for example antibodies, cytokines, bactericidal/permeability increasing protein (BPI) products; iv) one or more antibacterial agents useful in the treatment of pulmonary tuberculosis, extra-pulmonary tuberculosis, avium infections, buruli ulcers and/or v) one or more efflux pump inhibitors.

If not commercially available, the necessary starting materials for the procedures such as those described herein may be made by procedures which are selected from standard organic chemical techniques, techniques which are analogous to the synthesis of known, structurally similar compounds, or techniques which are analogous to the described procedure or the procedures described in the Examples.

It is noted that many of the starting materials for synthetic methods as described herein are commercially available and/or widely reported in the scientific literature, or could be made from commercially available compounds using adaptations of processes reported in the scientific literature. The reader is further referred to Advanced Organic Chemistry, 5th Edition, by Jerry March and Michael Smith, published by John Wiley & Sons 2001, for general guidance on reaction conditions and reagents.

It will also be appreciated that in some of the reactions mentioned herein it may be necessary/desirable to protect any sensitive groups in compounds. The instances where protection is necessary or desirable are known to those skilled in the art, as are suitable methods for such protection. Conventional protecting groups may be used in accordance with standard practice (for illustration see T. W. Greene, Protective Groups in Organic Synthesis, published by John Wiley and Sons, 1991) and as described hereinabove.

Abbreviations

The following abbreviations are employed in the examples and elsewhere herein:
TLC—thin layer chromatography;
HPLC—high pressure liquid chromatography;

MPLC—medium pressure liquid chromatography;
NMR—nuclear magnetic resonance spectroscopy;
DMSO—dimethylsulfoxide;
CDCl₃—deuterated chloroform;
MeOD—deuterated methanol, i.e. D₃COD;
MS—mass spectroscopy; ESP (or ES)—electrospray; EI—electron impact; APCI—atmospheric pressure chemical ionization;
THF—tetrahydrofuran;
DCM—dichloromethane;
MeOH—methanol;
DMF—dimethylformamide;
EtOAc—ethyl acetate;
LC/MS—liquid chromatography/mass spectrometry;
h—hour(s); min is minute(s);
d—day(s);
MTBD—N-methyl-1,5,7-triazabicyclo[4.4.0]dec-5-ene;
TFA—trifluoroacetic acid; v/v—ratio of volume/volume;
Boc denotes t-butoxycarbonyl;
Cbz denotes benzyloxycarbonyl;
Bz denotes benzoyl;
atm denotes atmospheric pressure;
rt denotes room temperature;
mg denotes milligram; g denotes gram;
μL denotes microliter;
mL denotes milliliter;
L denotes liter;
μM denotes micromolar;
mM denotes millimolar; M denotes molar;
N denotes normal; and
nm denotes nanometer.

EXAMPLES

The following examples provide the details about the synthesis, activities and applications of the compounds of the present disclosure. It should be understood the following is representative only, and that the invention is not limited by the details set forth in these examples.

Materials and Methods:

Evaporations were carried out by rotary evaporation in vacuo and work up procedures were carried out after removal of residual solids by filtration; temperatures are quoted as ° C.; operations were carried out at room temperature, that is typically in the range 18 to 26° C. and without the exclusion of air unless otherwise stated, or unless the skilled person would otherwise work under an inert atmosphere; column chromatography (by the flash procedure) was used to purify compounds and was performed on Merck Kieselgel silica (Art. 9385) unless otherwise stated; in general, the course of reactions was followed by TLC, HPLC, or LC/MS and reaction times are given for illustration only; yields are given for illustration only and are not necessarily the maximum attainable; the structure of the end products of the invention was generally confirmed by NMR and mass spectral techniques. Proton magnetic resonance spectra were generally determined in DMSO d6 unless otherwise stated, using a Bruker DRX 300 spectrometer or a Bruker DRX-400 spectrometer, operating at a field strength of 300 MHz or 400 MHz, respectively. In cases where the NMR spectrum is complex, only diagnostic signals are reported. Chemical shifts are reported in parts per million downfield from tetramethylsilane as an external standard (* scale) and peak multiplicities are shown thus: s, singlet; d, doublet; dd, doublet of doublets; dt, doublet of triplets; dm, doublet of multiplets; t, triplet, m, multiplet; br, broad. Fast atom bombardment (FAB) mass spectral data were generally obtained using a Platform spectrometer (supplied by Micromass) run in electrospray and, where appropriate, either positive ion data or negative ion data were collected or using Agilent 1100 series LC/MS equipped with Sedex 75ELSD, and where appropriate, either positive ion data or negative ion data were collected. The lowest mass major ion is reported for molecules where isotope splitting results in multiple mass spectral peaks (for example when chlorine is present). Reverse Phase HPLC was carried out using YMC Pack ODS AQ (100×20 mmID, S 5 Å particle size, 12 nm pore size) on Agilent instruments; each intermediate was purified to the standard required for the subsequent stage and was characterized in sufficient detail to confirm that the assigned structure was correct; purity was assessed by HPLC, TLC, or NMR and identity was determined by infrared spectroscopy (IR), mass spectroscopy or NMR spectroscopy as appropriate.

Synthesis of Intermediates

Synthesis of 6-Bromo-2H-pyrido[3,2-b][1,4]oxazin-3(4H)-one (Intermediate I)

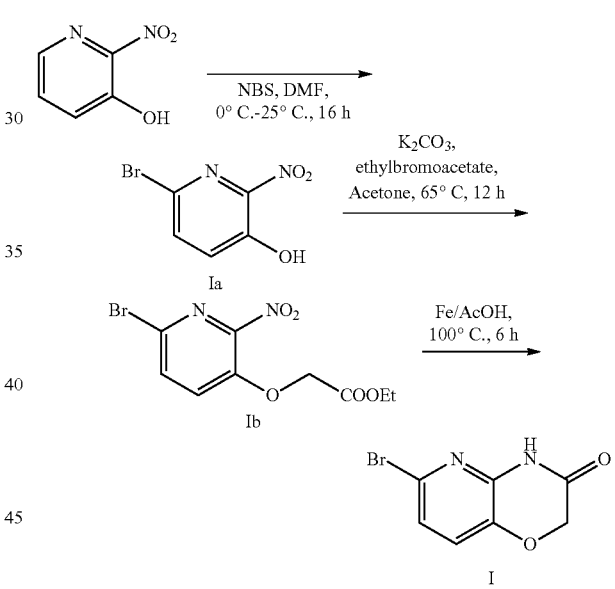

Step 1: Synthesis of 6-bromo-2-nitropyridin-3-ol (Ia)

To a solution of 4,6-dichloro-5-metho 2-nitropyridin-3-ol (20 g, 0.142 mol) in DMF (400 ml), N-bromosuccinimide (32.52 g, 0.187 mol) was added portion wise over a period of 5 hours at 0° C. The reaction mixture was stirred for room temperature for 12 h. After completion of the reaction, the reaction mixture was concentrated in vacuo. The residue was taken up in the Ether and the mixture was stirred for 30 min. The precipitate was removed by filtration and the filtrate was concentrated in vacuo to get 6-bromo-2-nitropyridin-3-ol, Ia (40 g, 46%) as a mixture of mono and di bromo compound. The crude LCMS showed 46% of expected mono-bromo compound, this material was used as such for next step without further purification. LCMS Calculated for C₅H₃BrN₂O₃, 218.99, Observed=219.2.

Step 2: Synthesis of ethyl 2-((6-bromo-2-nitropyridin-3-yl)oxy)acetate (Ib)

To solution of 6-bromo-2-nitropyridin-3-ol, 1a (40 g, 0.182 mol) in Acetone (400 ml), cooled to 0° C., potassium carbonate (50.41 g, 0.365 mol), was added and stirred for 5 min. Then, Ethyl bromoacetate (39.7 g, 0.237 mol) was added slowly and refluxed at 65° C. for 12 h. After completion of the reaction, it was filtered and the filtrate was concentrated in vacuo. The crude was diluted with water and extracted with Ethyl acetate (2*600 mL). The combined organic layers were washed with brine solution, dried over $Na_2SO_4$, filtered and concentrated in vacuo. It was purified by column chromatography on silica gel with gradient elution of 20-22% of Ethyl acetate in pet ether to obtain ethyl 2-((6-bromo-2-nitropyridin-3-yl)oxy)acetate, Ib (21 g, 75.32%) as a pale yellow solid. LCMS=Calculated for $C_9H_9BrN_2O_5$, 305.38, Observed=306.2.

Step 3: Synthesis of 6-bromo-2H-pyrido[3,2-b][1,4]oxazin-3(4H)-one (I)

To a stirred solution of ethyl 2-((6-bromo-2-nitropyridin-3-yl)oxy)acetate, Ib (21 g, 0.0687 mol) in glacial acetic acid (400 ml), Iron powder (11.51 g, 0.2063 mol) was added and heated to 100° C. for 6 hours. After completion of the reaction, reaction mixture was filtered through celite bed using ethyl acetate, 10% Methanol and concentrated in vacuo. It was washed with Methanol to obtain pure 6-bromo-2H-pyrido[3,2-b][1,4]oxazin-3(4H)-one, I (12 g, 76.28%). LCMS=Calculated for $C_7H_5BrN_2O_2$, 229.03, Observed=230.2.

Synthesis of 6-(5-(2-Aminoethyl)-2-oxooxazolidin-3-yl)-2H-pyrido[3,2-b][1,4]oxazin-3(4H)-one (Intermediate II)

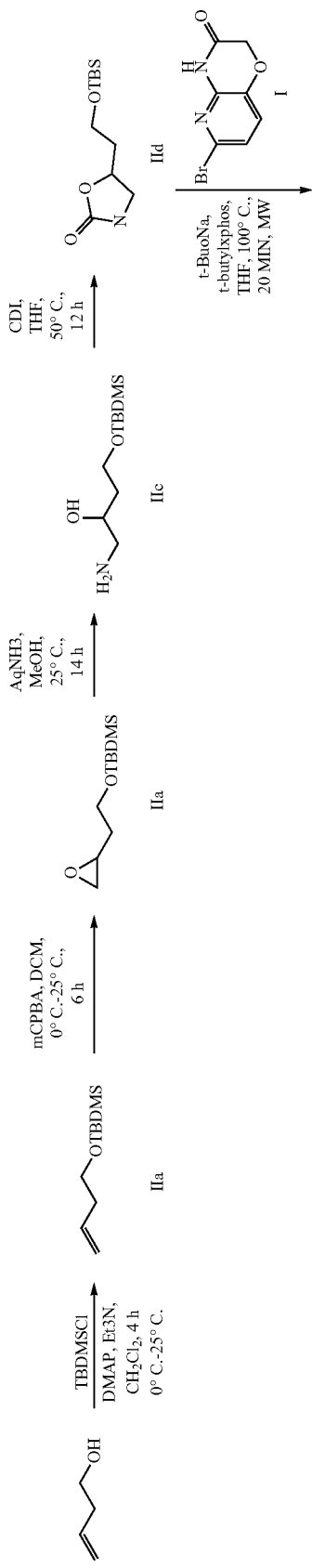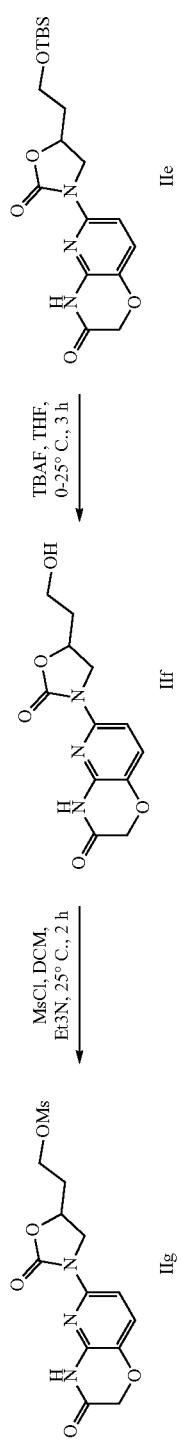

Step 1: Synthesis of (but-3-en-1-yloxy)(tert-butyl)dimethylsilane, IIa

To a stirred solution of but-3-en-1-ol (10 g, 0.1386 mol) in Dichloromethane (150 ml), cooled to 0° C., triethylamine (19.64 g, 0.1941 mol), was added and stirred for 5 min. Then, tert-butyldimethylsilyl chloride (25.08 g, 0.1664 mol) and DMAP (a catalytic amount) in dichloromethane was slowly added to the reaction mixture and stirred at 25° C. for 4 hours. After completion of the reaction, reaction mixture was quenched with water and extracted with MTBE. The combined organic layers were washed with brine solution, dried over $Na_2SO_4$, filtered and concentrated in vacuo at 40° C. to obtain (but-3-en-1-yloxy)(tert-butyl)dimethylsilane, IIa (24 g, 93%). The crude material was taken for the next step without any purification based on NMR monitoring of the reaction.

Step 2: Synthesis of tert-butyldimethyl(2-(oxiran-2-yl)ethoxy)silane, IIb

To a stirred solution of (but-3-en-1-yloxy)(tert-butyl)dimethylsilane, IIa (24 g, 0.1287 mol) in dichloromethane (480 ml), cooled to 0° C., m-CPBA (63.49 g, 0.2575 mol), was added portion wise and stirred at 25° C. for 7 hours. After completion of the reaction, reaction mixture was filtered to remove inorganics. Then, it was quenched with 10% sodium thio sulphate and extracted with dichloromethane. The separated organic layer was washed with 10% sodium bicarbonate, brine solution, dried over $Na_2SO_4$, filtered and concentrated in vacuo at 40° C. to obtain tert-butyldimethyl(2-(oxiran-2-yl)ethoxy)silane, IIb (22 g, 85%). The crude material was taken for the next step without any purification.

Step 3: Synthesis of 1-amino-4-((tert-butyldimethylsilyl)oxy)butan-2-ol, IIc To a stirred solution of tert-butyldimethyl(2-(oxiran-2-yl)ethoxy)silane, lib (22 g, 0.1087 mol) in methanol (100 ml), were added $NH_3$ in methanol (250 ml) and aqueous ammonia (100 ml) and stirred at 25° C. for 14 hours. After completion of the reaction, reaction mixture was concentrated in vacuo to obtain 1-amino-4-((tert-butyldimethylsilyl)oxy)butan-2-ol, IIc (20 g, 84%). The crude material was taken for the next step without any purification. LCMS=Calculated for $C_{10}H_{25}NO_2Si$, 219.4, Observed=220.2.

Step 4: Synthesis of 5-(2-((tert-butyldimethylsilyl)oxy)ethyl)oxazolidin-2-one, IId To a stirred solution of 1-amino-4-((tert-butyldimethylsilyl)oxy)butan-2-ol, IIc (20 g, 0.0912 mol) in THF (300 ml), cooled to 0° C., CDI (22.5 g, 0.1368 mol), was added portion wise and heated at 50° C. for 14 hours. After completion of the reaction, reaction mixture was quenched with water and extracted with ethyl acetate. The separated organic layer was washed with water, brine solution, dried over $Na_2SO_4$, filtered and concentrated in vacuo. It was purified by column chromatography on silica gel (230-400 mesh) with gradient elution of 35-40% ethyl acetate in pet ether to obtain 5-(2-((tert-butyldimethylsilyl)oxy)ethyl)oxazolidin-2-one, IId (10 g, 45%). LCMS=Calculated for $C_{11}H_{23}NO_3Si$, 245.39, Observed=246.4.

Step 5: Synthesis of 6-(5-(2-((tert-butyldimethylsilyl)oxy)ethyl)-2-oxooxazolidin-3-yl)-2H-pyrido[3,2-b][1,4]oxazin-3(4H)-one, IIe To a stirred solution of 6-bromo-2H-pyrido[3,2-b][1,4] oxazin-3(4H)-one, I (0.3 g, 0.0013 mol) and 5-(2-((tert-butyldimethylsilyl)oxy)ethyl)oxazolidin-2-one, IId (0.385 g, 0.0015 mol) in Aldrich dry THF (10 ml), were added t-butyl-X-Phos mesyl chloride complex (0.051 g, 0.00006 mol) and sodium tert-butoxide (0.187 g, 0.0019 mol) and degassed for 20 mins. Then, it was irradiated in microwave at 100° C. for 25 mins. After completion of the reaction, reaction mixture was concentrated in vacuo. It was purified by column chromatography on silica gel (230-400 mesh) with gradient elution of 21-25% ethyl acetate in pet ether to obtain 6-(5-(2-((tert-butyldimethylsilyl)oxy)ethyl)-2-oxooxazolidin-3-yl)-2H-pyrido[3,2-b][1,4]oxazin-3(4H)-one, IIe (0.2 g, 40%). LCMS=Calculated for $C_{18}H_{27}N_3O_5Si$, 393.52, Observed=394.5.

Step 6: Synthesis of 6-(5-(2-hydroxyethyl)-2-oxooxazolidin-3-yl)-2H-pyrido[3,2-b][1,4]oxazin-3(4H)-one, IIf To a stirred solution of 6-(5-(2-((tert-butyldimethylsilyl)oxy)ethyl)-2-oxooxazolidin-3-yl)-2H-pyrido[3,2-b][1,4]oxazin-3 (4H)-one, IIe (1 g, 0.0025 mol) in THF (15 ml), cooled to 0° C., Tert-butyl ammonium fluoride (1.99 g, 0.0076 mol) was added drop wise and stirred at 25° C. for 3 hours. After completion of the reaction, reaction mixture was quenched with water and extracted with ethyl acetate. The separated organic layer was washed with brine solution, dried over $Na_2SO_4$, filtered and concentrated in vacuo to obtain colourless gummy solid of 6-(5-(2-hydroxyethyl)-2-oxooxazolidin-3-yl)-2H-pyrido[3,2-b][1,4]oxazin-3(4H)-one, IIf (0.5 g, 71.63%). The crude material was taken for the next step without any purification. LCMS=Calculated for $C_{12}H_{13}N_3O_5$, 279.24, Observed=280.2.

Step 7: Synthesis of 2-(2-oxo-3-(3-oxo-3,4-dihydro-2H-pyrido[3,2-b][1,4]oxazin-6-yl)oxazolidin-5-yl) ethyl methanesulfonate, IIg To a stirred solution of 6-(5-(2-hydroxyethyl)-2-oxooxazolidin-3-yl)-2H-pyrido[3,2-b][1,4]oxazin-3(4H)-one, IIf (0.5 g, 0.0017 mol) in dichloromethane, cooled to 0° C., triethylamine (0.543 g, 0.0053 mol) and mesyl chloride (0.155 g, 0.0013 mol) were added and stirred at 25° C. for 2 hours. After completion of the reaction, reaction mixture was quenched with water and extracted with dichloromethane. The separated organic layer was washed with water, brine solution, dried over $Na_2SO_4$, filtered and concentrated in vacuo to obtain pale brown gummy solid of 2-(2-oxo-3-(3-oxo-3,4-dihydro-2H-pyrido[3,2-b][1,4]oxazin-6-yl)oxazolidin-5-yl)ethyl methanesulfonate, IIg (0.5 g, 82.50%). The crude material was taken for the next step without any purification. LCMS=Calculated for $C_{13}H_{15}N_3O_7S$, 357.34, Observed=358.4.

Step 8: Synthesis of 6-(5-(2-azidoethyl)-2-oxooxazolidin-3-yl)-2H-pyrido[3,2-b][1,4]oxazin-3(4H)-one, IIh To a stirred solution of 2-(2-oxo-3-(3-oxo-3,4-dihydro-2H-pyrido[3,2-b][1,4]oxazin-6-yl)oxazolidin-5-yl)ethyl methanesulfonate, IIg (0.5 g, 0.0013 mol) in DMF (10 ml), cooled to 0° C., sodium azide (0.181 g, 0.0027 mol) was added and heated at 60° C. for 3 hours. After completion of the reaction, reaction mixture was quenched with water and extracted with ethyl acetate. The separated organic layer was washed with water, brine solution, dried over $Na_2SO_4$, filtered and concentrated in vacuo. It was purified by column chromatography on silica gel (230-400 mesh) with gradient elution of 50-60% ethyl acetate in pet ether to obtain colourless solid of 6-(5-(2-azidoethyl)-2-oxooxazolidin-3-yl)-2H-pyrido[3,2-b][1,4]oxazin-3(4H)-one, IIh (0.32 g, 81.01%). LCMS=Calculated for $C_{12}H_{12}N_6O_4$, 304.27, Observed=305.5.

Step 9: Synthesis of 6-(5-(2-aminoethyl)-2-oxooxazolidin-3-yl)-2H-pyrido[3,2-b][1,4]oxazin-3(4H)-one (Intermediate II)

To a stirred solution of 6-(5-(2-azidoethyl)-2-oxooxazolidin-3-yl)-2H-pyrido[3,2-b][1,4]oxazin-3(4H)-one, 12 (0.32 g, 0.0010 mol) in THF:MeOH (1:1) (10 ml), 10% palladium on carbon (30 mg) was added and stirred at 25° C. under $H_2$ bladder pressure for 3 hours. After completion of the reaction, reaction mixture was filtered through celite bed using THF and MeOH and concentrated in vacuo to obtain colourless solid of 6-(5-(2-aminoethyl)-2-oxooxazolidin-3-yl)-2H-pyrido[3,2-b][1,4]oxazin-3(4H)-one, II (0.25 g, 89.92%). The crude material was taken for the next step without any purification. $^1$H NMR (400 MHz, DMSO-d6) δ 7.60 (d, J=8.6 Hz, 1H), 7.44 (d, J=8.6 Hz, 1H), 4.79-4.80 (m, 1H), 4.62 (s, 2H), 4.21-4.25 (m, 1H), 3.73-3.77 (m, 1H), 2.87-2.90 (m, 2H), 1.75-1.88 (m, 2H), 1.36 (s, 2H); LCMS calculated for $C_{12}H_{14}N_4O_4$, 278.27 Observed=279

Synthesis of 6-(5-(3-Aminopropyl)-2-oxooxazolidin-3-yl)-2H-pyrido[3,2-b][1,4]oxazin-3(4H)-one (Intermediate III)

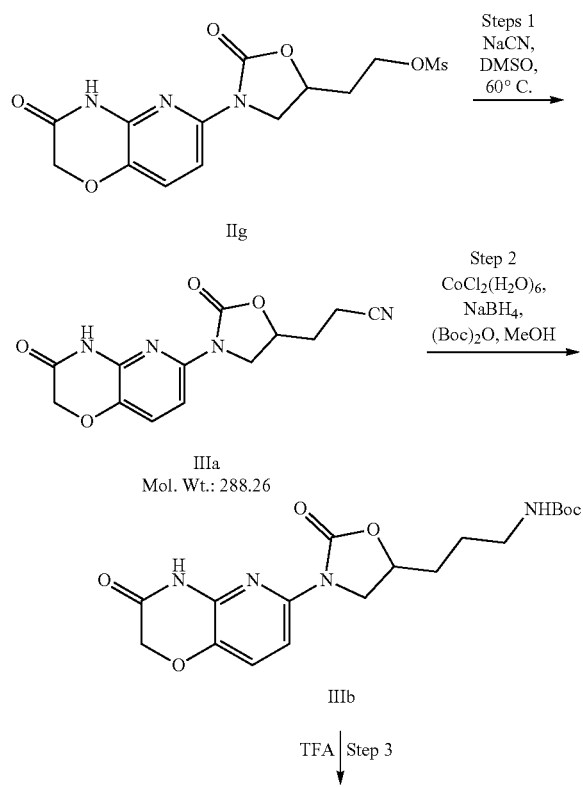

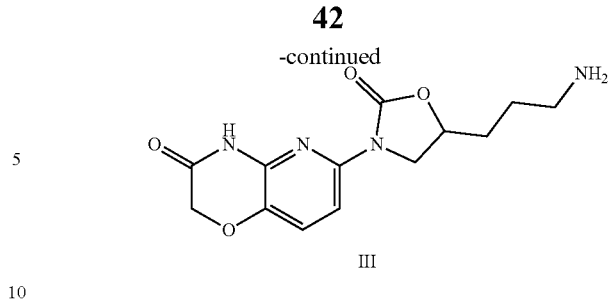

Step-1: Synthesis of 3-(2-oxo-3-(3-oxo-3,4-dihydro-2H-pyrido[3,2-b][1,4]oxazin-6-yl)oxazolidin-5-yl)propanenitrile(IIIa)

To a stirred solution of starting material IIg (0.7 g, 1.96 mmol) in DMSO (5 mL) was added sodium cyanide (0.38 g, 7.84 mmol), and the resulting reaction mixture was heated to 50° C. for 3 h. The reaction was monitored by LCMS. After completion of the reaction, the reaction mixture was poured into water (15 ml) and extracted with Ethyl acetate (2×30 mL). The combined organic layers were washed with brine solution (20 mL) and concentrated under reduced pressure to obtain crude compound, which was purified by column chromatography eluted with 40% EtOAC in pet ether to afford title compound (0.1 g) as an off white solid.

Step-2: Synthesis of tert-butyl (3-(2-oxo-3-(3-oxo-3,4-dihydro-2H-pyrido[3,2-b][1,4]oxazin-6-yl)oxazolidin-5-yl)propyl)carbamate (IIIb)

To a stirred solution of starting material, IIIa (0.1 g, 0.346 mmol) in Methanol (5 mL) was added Cobalt(II)chloride hexahydrate (0.41 g, 1.734 mmol) and Boc-anhydride (0.138 g, 0.692 mmol) at 0° C. After 5 min stirring, sodium borohydride (40 mg, 1.038 mmol) was added, reaction was warmed to room temperature and stirred for 4 h. After the complete consumption of starting material, the reaction mixture was filtered through celite bed, and filtrate was concentrated on rotatory evaporator. Obtained residue was diluted with water, and extracted with ethyl acetate (2×20 mL). The combined organic layers were washed with brine solution (15 mL) and concentrated to obtain a crude residue, which was purified by column chromatography by using 35% EtOAC in pet ether to afford title compound (50 mg) as a pale yellow solid.

Step-3: Synthesis of 6-(5-(3-Aminopropyl)-2-oxooxazolidin-3-yl)-2H-pyrido[3,2-b][1,4]oxazin-3(4H)-one(III)

To a stirred solution of starting material, IIIb (50 mg,) in dichloromethane (5 mL), was added trifluoroacetic acid (0.5 mL) at 0° C. and stirred at RT for 3 h. After completion of the reaction, the reaction mixture was concentrated in vacuo, and washed with pet ether to afford title compound (40 mg) as light brown solid. $^1$H NMR (400 MHz, DMSO-d6) δ 7.71 (bs, 1H), δ 7.59 (d, J=8.6 Hz, 1H), 7.44 (d, J=8.6 Hz, 1H), 4.68-4.75 (m, 1H), 4.61 (s, 2H), 4.22 (dd, J=8.4, 10 Hz, 1H), 3.70 (dd, J=6.6 Hz, 10 Hz, 1H), 2.85 (t, J=8.0 Hz, 2H), 1.73-1.81 (m, 2H), 1.61-1.71 (m, 2H); LCMS calculated for $C_{13}H_{16}N_4O_4$, 292.30 Observed=293.2.

Alternate route for the synthesis of 6-(5-(3-Aminopropyl)-2-oxooxazolidin-3-yl)-2H-pyrido[3,2-b][1,4]oxazin-3(4H)-one (Intermediate III)

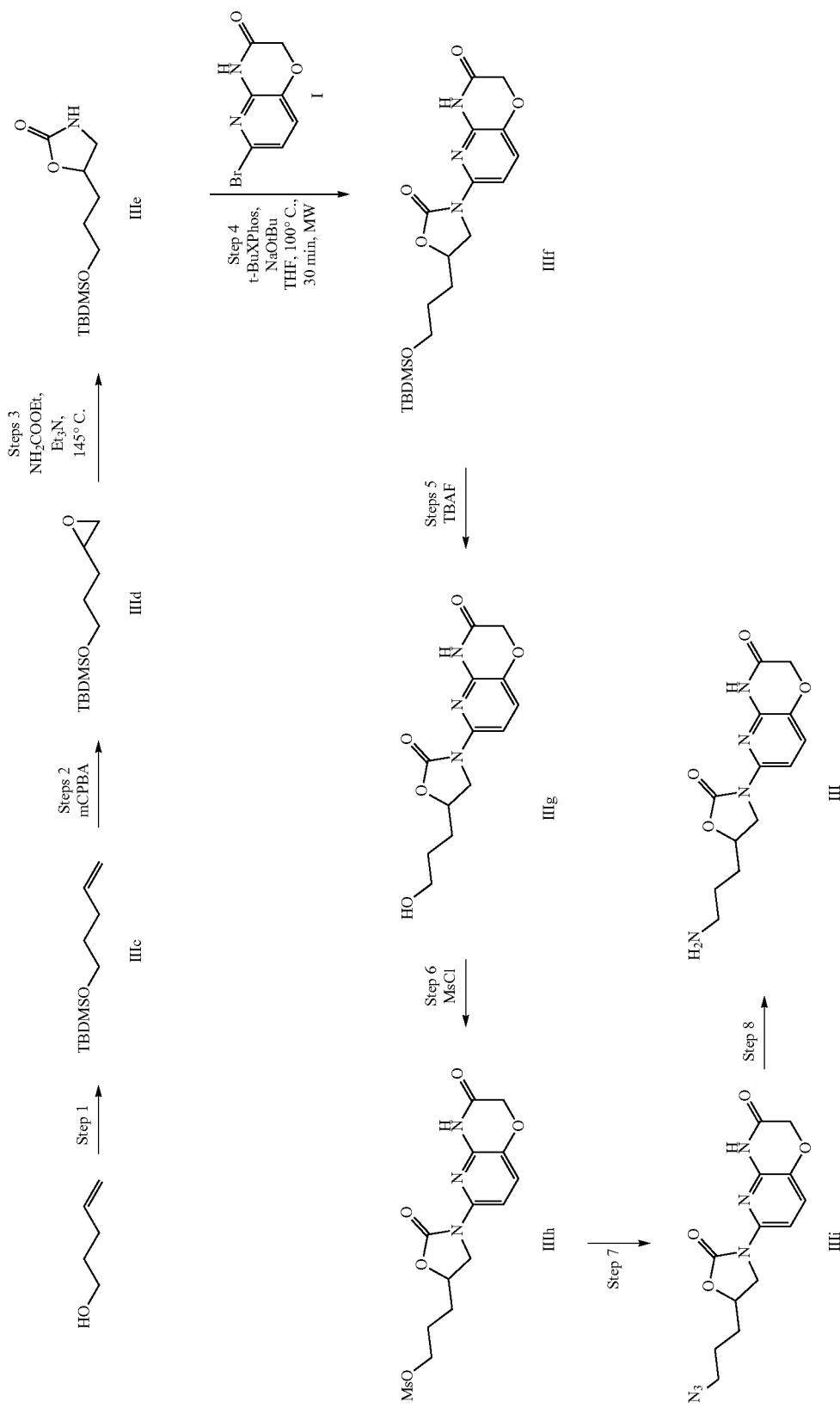

Step 1: Synthesis of (pent-3-en-1-yloxy)(tert-butyl)dimethylsilane, IIIc

The solution of pent-3-en-1-ol (20 g, 0.232 mol) in dichloromethane (200 ml) was cooled to 0° C., and triethylamine (45.01 mL, 0.325 mol), followed by tert-butyldimethylsilyl chloride (50.3 g, 0.0.278 mol) and DMAP (0.56 g, 4.644 mmol) were added to the reaction mixture and stirred at 25° C. for 4 hours. After completion of the reaction, reaction mixture was diluted with dichloromethane (100 mL) and washed successively with water and brine solution. Organic layer was dried over $Na_2SO_4$, and concentrated in vacuo at 40° C. to obtain (pent-3-en-1-yloxy)(tert-butyl)dimethylsilane, IIIc (42.06 g). The crude material was taken for the next step without any purification. $^1HNMR$ (DMSO-d6) δ 5.76-5.86 (m, 1H), 4.93-5.04 (m, 2H), 3.58 (t, J=8.4 hz, 2H), 2.02-2.10 (m, 2H), 1.49-1.58 (m, 2H), 0.93 (s, 9H), 0.09 (s, 6H)

Step 2: Synthesis of tert-butyldimethyl(2-(oxiran-2-yl)ethoxy)silane, IIId

A stirred solution of (pent-3-en-1-yloxy)(tert-butyl)dimethylsilane, IIIc (25 g, 0.125 mol) in dichloromethane (500 ml) was cooled to 0° C. and m-CPBA (63.49 g, 0.2575 mol), was added portion wise over 20 mins. After the completion of addition, reaction was warmed to 25° C. and stirred for 7 hours. Reaction mixture was filtered to remove inorganics. Then, it was quenched with 10% sodium thio sulphate and extracted with dichloromethane. The separated organic layer was washed with 10% sodium bicarbonate, brine solution, dried over $Na_2SO_4$, filtered and concentrated in vacuo at 40° C. to obtain tert-butyldimethyl(2-(oxiran-2-yl)ethoxy)silane, IIId (21 g). The crude material was taken for the next step without any purification.

Step 3: Synthesis of Intermediate IIIe

To the mixture of epoxide IIId (9 g, 0.039 mol) and ethylcarbamate (3.5 g, 0.039 mol) in a sealed tube, was added triethylamine (5 mL, 0.039 mol) and the mixture was heated at 145° C. for overnight.
After the completion of reaction, reaction mixture was diluted with water and extracted with ethyl acetate. Organic layer was washed with water, dried over sodium sulphate and evaporated under reduced pressure. Crude residue was purified by silica gel column chromatography (25% ethyl acetate in pet-ether) to get intermediate IIIe (4.0 g). LCMS calculated for $C_{12}H_{25}NO_3Si$ 259.42, observed=260.0

Step 4: 6-(5-(2-((tert-butyldimethylsilyl)oxy)propyl)-2-oxooxazolidin-3-yl)-2H-pyrido[3,2-b][1,4]oxazin-3(4H)-one, IIIf To a stirred solution of 6-bromo-2H-pyrido[3,2-b][1,4]oxazin-3(4H)-one, I (0.300 g, 1.310 mmol) and 5-(2-((tert-butyldimethylsilyl)oxy)propyl)oxazolidin-2-one, IIIe (0.407 g, 1.572 mmol) in Aldrich dry THF (12 ml), were added t-butyl-X-Phos mesyl chloride complex (0.052 g, 0.0655 mmol) and sodium tert-butoxide (0.189 g, 1.965 mmol) and degassed for 20 mins. Then, it was irradiated in microwave at 100° C. for 40 mins. After completion of the reaction, reaction mixture was concentrated in vacuo. It was purified by column chromatography on silica gel (230-400 mesh) with gradient elution of 21-25% ethyl acetate in pet ether to obtain 6-(5-(2-((tert-butyldimethylsilyl)oxy)propyl)-2-oxooxazolidin-3-yl)-2H-pyrido[3,2-b][1,4]oxazin-3(4H)-one, IIIf (0.231 g). LCMS calculated for $C_{19}H_{29}N_3O_5Si$ 407.42, Observed=408

Step 5: Synthesis of 6-(5-(3-hydroxypropyl)-2-oxooxazolidin-3-yl)-2H-pyrido[3,2-b][1,4]oxazin-3(4H)-one, IIIg To a stirred solution of 6-(5-(2-((tert-butyldimethylsilyl)oxy)propyl)-2-oxooxazolidin-3-yl)-2H-pyrido[3,2-b][1,4]oxazin-3(4H)-one, IIIf (4.3 g, 0.0105 mol) in THF (45 ml), cooled to 0° C., Tert-butyl ammonium fluoride (5.64 g, 0.0216 mol) was added drop wise and stirred at 25° C. for 3 hours. After completion of the reaction, reaction mixture was quenched with water and extracted with ethyl acetate. The separated organic layer was washed with brine solution, dried over $Na_2SO_4$, filtered and concentrated in vacuo to obtain colourless gummy solid of 6-(5-(3-hydroxypropyl)-2-oxooxazolidin-3-yl)-2H-pyrido[3,2-b][1,4]oxazin-3(4H)-one, IIIg (2.95 g, 95.81%). The crude material was taken for the next step without any purification. LCMS=Calculated for $C_{13}H_{15}N_3O_5$, 293.28, Observed=293.8.

Step 6 Synthesis of 3-(2-oxo-3-(3-oxo-3,4-dihydro-2H-pyrido[3,2-b][1,4]oxazin-6-yl)oxazolidin-5-yl) propyl methanesulfonate, IIIh To a stirred solution of 6-(5-(3-hydroxypropyl)-2-oxooxazolidin-3-yl)-2H-pyrido[3,2-b][1,4]oxazin-3(4H)-one, IIIg (2.95 g, 0.010 mol) in dichloromethane (30 ml), cooled to 0° C., triethylamine (3.05 g, 0.030 mol) and mesyl chloride (1.14 g, 0.010 mol) were added and stirred at 25° C. for 2 hours. After completion of the reaction, reaction mixture was quenched with water and extracted with dichloromethane. The separated organic layer was washed with water, brine solution, dried over $Na_2SO_4$, filtered and concentrated in vacuo to obtain pale brown gummy solid of 3-(2-oxo-3-(3-oxo-3,4-dihydro-2H-pyrido[3,2-b][1,4]oxazin-6-yl)oxazolidin-5-yl)propyl methanesulfonate, IIIh (2.8 g, 75.47%). The crude material was taken for the next step without any purification. LCMS=Calculated for $C_{14}H_{17}N_3O_7S$, 371.36, Observed=371.8.

Step 7 Synthesis of 6-(5-(3-azidopropyl)-2-oxooxazolidin-3-yl)-2H-pyrido[3,2-b][1,4]oxazin-3(4H)-one, IIIi To a stirred solution of 3-(2-oxo-3-(3-oxo-3,4-dihydro-2H-pyrido[3,2-b][1,4]oxazin-6-yl)oxazolidin-5-yl)propyl methanesulfonate, IIIh (2.8 g, 0.0075 mol) in DMF (30 ml), cooled to 0° C., sodium azide (0.98 g, 0.0150 mol) was added and heated at 60° C. for 3 hours. After completion of the reaction, reaction mixture was quenched with water and extracted with ethyl acetate. The separated organic layer was washed with water, brine solution, dried over $Na_2SO_4$, filtered and concentrated in vacuo. It was purified by column chromatography on silica gel (230-400 mesh) with gradient elution of 38-43% ethyl acetate in pet ether to obtain colourless solid of 6-(5-(3-azidopropyl)-2-oxooxazolidin-3-yl)-2H-pyrido[3,2-b][1,4]oxazin-3(4H)-one, IIIi (1.5 g, 63.02%). LCMS=Calculated for $C_{13}H_{14}N_6O_4$, 318.29, Observed=318.8.

Step 8 Synthesis of 6-(5-(3-aminopropyl)-2-oxooxazolidin-3-yl)-2H-pyrido[3,2-b][1,4]oxazin-3(4H)-one, III To a stirred solution of 6-(5-(3-azidopropyl)-2-oxooxazolidin-3-yl)-2H-pyrido[3,2-b][1,4]oxazin-3(4H)-one, IIIi (1.3 g, 0.0010 mol) in THF:MeOH (1:1) (10 ml), 10% palladium on carbon (0.6 g) was added and stirred at 25° C. under $H_2$ bladder pressure for 3 hours. After completion of the reaction, reaction mixture was filtered through celite bed using THF and MeOH and concentrated in vacuo to obtain colourless solid of 6-(5-(3-aminopropyl)-2-oxooxazolidin-3-yl)-2H-pyrido[3,2-b][1,4]oxazin-3(4H)-one, III (0.8 g, 67.22%). The crude material was taken for the next step without any purification. $^1$H NMR (400 MHz, DMSO-d6) δ 7.71 (bs, 1H), δ 7.59 (d, J=8.6 Hz, 1H), 7.44 (d, J=8.6 Hz, 1H), 4.68-4.75 (m, 1H), 4.61 (s, 2H), 4.22 (dd, J=8.4, 10 Hz, 1H), 3.70 (dd, J=6.6 Hz, 10 Hz, 1H), 2.85 (t, J=8.0 Hz, 2H), 1.73-1.81 (m, 2H), 1.61-1.71 (m, 2H); LCMS calculated for $C_{13}H_{16}N_4O_4$, 292.30 Observed=293.2.s

Synthesis of 6-(5-(2-Aminoethyl)-2-oxooxazolidin-3-yl)-2H-benzo[b][1,4]oxazin-3(4H)-one (Intermediate IV)

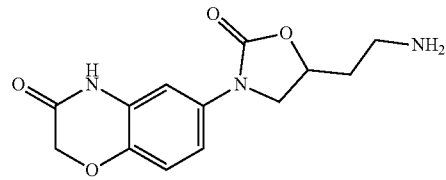 [SMILES: NCCC1CN(c2ccc3c(c2)NC(=O)CO3)C(=O)O1]

Intermediate IV, 6-(5-(2-Aminoethyl)-2-oxooxazolidin-3-yl)-2H-benzo[b][1,4]oxazin-3(4H)-one (CAS number 1072793-84-0) was synthesized as reported earlier in WO2008126024.

Synthesis of 5-(5-(2-aminoethyl)-2-oxooxazolidin-3-yl)-2-methylnicotinonitrile (Intermediate V)

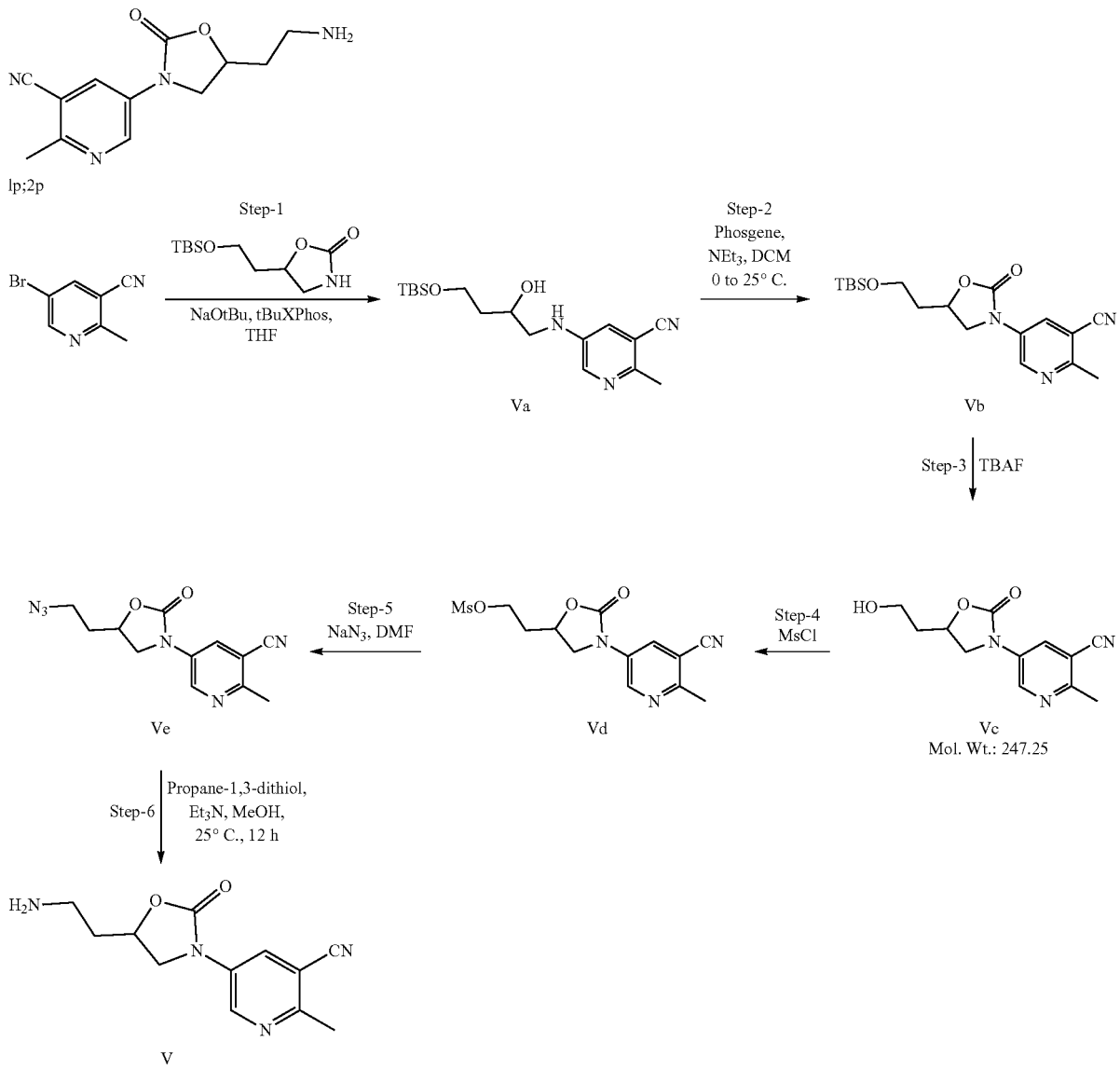

Step 1: Synthesis of 5-((4-((tert-butyldimethylsilyl)oxy)-2-hydroxybutyl)amino)-2-methylnicotinonitrile, Va To a stirred solution of 5-bromo-2-methylnicotinonitrile (850 mg, 4.31 mmol) and 5-(2-((tert-butyldimethylsilyl)oxy)ethyl)oxazolidin-2-one, IId (1268 mg, 5.17 mmol) in Aldrich dry THF (25 ml), were added t-butyl-X-Phos mesyl chloride complex (171 mg, 0.21 mmol) and sodium tert-butoxide (621 mg, 6.47 mmol) and degassed for 20 min. Then, it was irradiated in microwave at 100° C. for 20 mins. After completion of the reaction, reaction mixture was concentrated in vacuo. It was purified by column chromatography on silica gel (230-400 mesh) with gradient elution of 26-30% ethyl acetate in pet ether to obtain 5-((4-((tert-butyldimethylsilyl)oxy)-2-hydroxybutyl)amino)-2-methylnicotinonitrile, Va (500 mg, 35%). LCMS=Calculated for $C_{17}H_{29}N_3O_2Si$, 335.52, Observed=336.2.

Step 2: Synthesis of 5-(5-(2-((tert-butyldimethylsilyl)oxy)ethyl)-2-oxooxazolidin-3-yl)-2-methylnicotinonitrile, Vb To a stirred solution of 5-((4-((tert-butyldimethylsilyl)oxy)-2-hydroxybutyl)amino)-2-methylnicotinonitrile, Va (500 mg, 1.49 mmol) in dry Dichlormethane (5 ml), cooled to 0° C., triethylamine (754 mg, 7.54 mmol) and phosgene (1170 mg, 11.92 mmol) were added and stirred at 25° C. for 2 h. After completion of the reaction, reaction mixture was quenched with water and extracted with ethyl acetate. The separated organic layer was washed with brine solution, dried over $Na_2SO_4$, filtered and concentrated in vacuo. It was purified by column chromatography on silica gel (230-400 mesh) with gradient elution of 25-27% ethyl acetate in pet ether to obtain 5-(5-(2-((tert-butyldimethylsilyl)oxy)ethyl)-2-oxooxazolidin-3-yl)-2-methylnicotinonitrile, Vb (340 mg, 64%). LCMS=Calculated for $C_{18}H_{27}N_3O_3Si$, 361.52, Observed=362.

Step 3: Synthesis of 5-(5-(2-hydroxyethyl)-2-oxooxazolidin-3-yl)-2-methylnicotinonitrile, Vc To a stirred solution of 5-(5-(2-((tert-butyldimethylsilyl)oxy)ethyl)-2-oxooxazolidin-3-yl)-2-methylnicotinonitrile, Vb (340 mg, 0.94 mmol) in THF (8 ml), cooled to 0° C., Tert-butyl ammonium fluoride (737 mg, 2.82 mmol) was added drop wise and stirred at 25° C. for 3 hours. After completion of the reaction, reaction mixture was quenched with water and extracted with ethyl acetate. The separated organic layer was washed with brine solution, dried over $Na_2SO_4$, filtered and concentrated in vacuo to obtain colourless gummy solid of 5-(5-(2-hydroxyethyl)-2-oxooxazolidin-3-yl)-2-methylnicotinonitrile, Vc (200 mg, 86.2%). The crude material was taken for the next step without any purification. LCMS=Calculated for $C_{12}H_{13}N_3O_3$, 247.25, Observed=247.8.

Step 4: Synthesis of 2-(3-(5-cyano-6-methylpyridin-3-yl)-2-oxooxazolidin-5-yl)ethyl methanesulfonate, Vd To a stirred solution 5-(5-(2-hydroxyethyl)-2-oxooxazolidin-3-yl)-2-methylnicotinonitrile, Vc (200 mg, 0.80 mmol) in dichloromethane, cooled to 0° C., triethylamine (245 mg, 2.42 mmol) and mesyl chloride (91 mg, 0.80 mmol) were added and stirred at 25° C. for 2 hours. After completion of the reaction, reaction mixture was quenched with water and extracted with dichloromethane. The separated organic layer was washed with water, brine solution, dried over $Na_2SO_4$, filtered and concentrated in vacuo to obtain pale brown gummy solid of 2-(3-(5-cyano-6-methylpyridin-3-yl)-2-oxooxazolidin-5-yl)ethyl methanesulfonate, Vd (200 mg, 77%). The crude material was taken for the next step without any purification. LCMS=Calculated for $C_{13}H_{15}N_3O_5S$, 325.34, Observed=326.

Step 5: Synthesis of 5-(5-(2-azidoethyl)-2-oxooxazolidin-3-yl)-2-methylnicotinonitrile, Ve To a stirred solution of 2-(3-(5-cyano-6-methylpyridin-3-yl)-2-oxooxazolidin-5-yl)ethyl methanesulfonate, Vd (200 mg, 0.614 mmol) in DMF (4 ml), cooled to 0° C., sodium azide (59 mg, 0.92 mmol) was added and heated at 60° C. for 3 hours. After completion of the reaction, reaction mixture was quenched with water and extracted with ethyl acetate. The separated organic layer was washed with water, brine solution, dried over $Na_2SO_4$, filtered and concentrated in vacuo. It was purified by column chromatography on silica gel (230-400 mesh) with gradient elution of 48-52% ethyl acetate in pet ether to obtain colourless gummy solid of 5-(5-(2-azidoethyl)-2-oxooxazolidin-3-yl)-2-methylnicotinonitrile, Ve (100 mg, 60%). LCMS=Calculated for $C_{12}H_{12}N_6O_2$, 272.27, Observed=273.5.

Step 6: Synthesis of 5-(5-(2-aminoethyl)-2-oxooxazolidin-3-yl)-2-methylnicotinonitrile, V To a stirred solution of 5-(5-(2-azidoethyl)-2-oxooxazolidin-3-yl)-2-methylnicotinonitrile, Ve (50 mg, 0.183 mmol) in Methanol (5 ml), triethylamine (74 mg, 0.734 mmol) and 1,3-propane dithiol (79 mg, 0.734 mmol) were added and stirred at 25° C. for 12 hours. After completion of the reaction, reaction mixture was filtered to remove inorganics and concentrated in vacuo to obtain crude pale green colour of gummy liquid of 5-(5-(2-aminoethyl)-2-oxooxazolidin-3-yl)-2-methylnicotinonitrile, V (43 mg, 95%). The crude material was taken for the next step without any purification. LCMS=Calculated for $C_{12}H_{14}N_4O_2$, 246.27, Observed=247.0.

Synthesis of 1-methyl-2-oxoindoline-7-carbaldehyde, Intermediate VI

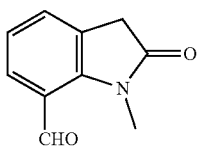

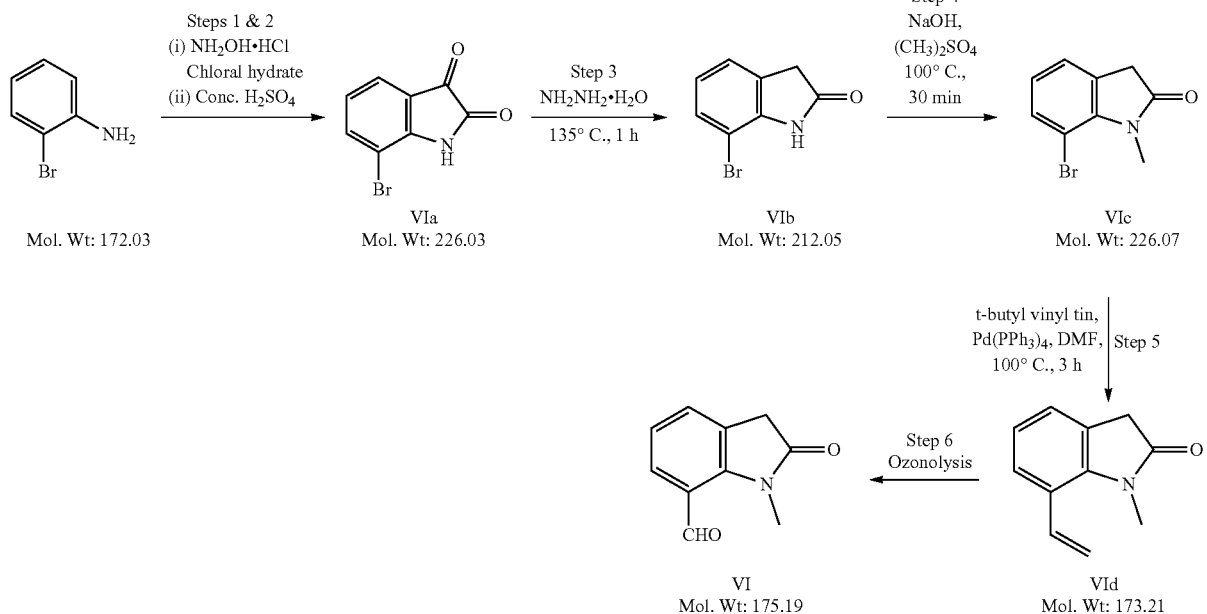

Step-1: Synthesis of VIa

To a solution of chloral hydrate (5.28 g, 31.9 mmol) in deionized water (90 mL), sodium sulphate (53.6 g, 377.9 mmol), 2-bromoaniline (5 g, 29.11 mmol), were added sulphuric acid (20 mL) followed by hydroxylamine hydrochloride (6.66 g, 87.2 mmol) and the whole mixture was heated to 13° C. for 30 min. The mixture was cooled to room temperature, poured on ice-water mixture and extracted with ethylacetate. Organic layer was washed with brine, dried over sodium sulphate and evaporated under reduced pressure. Crude obtained was taken for the next step without any purification.

Step-2

Sulphuric acid (50 mL) was added to the crude obtained in step 1 and the mixture was heated to 70° C. for 1 h. After the complete consumption of starting material, reaction mixture was poured over ice, and extracted with ethyl acetate (2×200 mL). Organic layer was washed with brine, dried over sodium sulphate and evaporated under reduced pressure. Crude was purified by silica gel column chromatography by using 20% ethyl acetate in pet ether for elution to get 2.5 g of VIa.

Step-3: Synthesis of VIb

To a solution of VIa (2.5 g, 11.061 mmol) in ethanol (50 mL), hydrazine hydrate (99%, 0.5 mL) was added and the mixture was refluxed under nitrogen atmosphere for 30 min. Formed yellow precipitate was isolated by filtration, and suspended in anhydrous ethanol. Potassium tertiary butoxide (4.03 g, 35.90 mmol) was added to the above suspension. The mixture was refluxed for 2 h. After the completion of reaction, mixture was poured over ice-water, acidified with dil. HCl to pH 2. Mixture was extracted with ethyl acetate. Organic layer was washed with brine, dried over sodium sulphate and evaporated under reduced pressure to get crude of VIb (0.89 g) which was taken for the next step without any purification.

Step-4: Preparation of VIc

To the suspension of VIb (200 mg, 0.94 mmol) in water (5 mL) and sodium hydroxide (56 mg, 1.41 mmol) was added dimethyl sulphate (178 mg, 1.41 mmol) and the mixture was heated at 100° C. for 1 h. After the consumption of starting material, reaction mixture was cooled to 0° C., added water and extracted with ethyl acetate. Organic layer was washed with brine, dried over sodium sulphate and evaporated under reduced pressure. So obtained crude was purified by column chromatography by using 10% ethyl acetate in pet-ether to get pure VIc (180 mg).

Step-5: Preparation of VId

To a solution of VIc (180 mg, 0.79 mmol) in DMF (4 mL) was added tributylvinyltin (0.26 mL, 2.25 mmol) followed by palladium tetrakis-triphenylphosphine (45 mg, 0.103 mmol) and the mixture was degassed for 30 min by purging with argon. Reaction was heated to 100° C. for 3 h. After the completion of reaction, mixture was cooled to 0° C., added water and extracted with ethyl acetate. Organic layer was washed with brine, dried over sodium sulphate and evaporated under reduced pressure. So, obtained crude was purified by column chromatography using 10% ethyl acetate in pet-ether to pure VId (100 mg)

Step-6 Preparation of VI

Olefin VId (100 mg, 0.52 mmol) was dissolved in 4 mL methanol and purged with oxygen for 10 min. Mixture was than cooled to −78° C. and ozone was continuously passed through reaction mixture for 30 min. After the complete consumption of VId, reaction mass was quenched with dimethylsulphide (0.5 mL) and evaporated under reduced pressure to dryness. Residue obtained was purified by column chromatography with eluent 15% ethyl acetate in pet ether to obtain pale yellow solid (30 mg). $^1$HNMR (400 MHz, CDCl$_3$) δ 10.45 (s, 1H), 7.81 (d, J=7.6 Hz, 1H), 7.45 (dd, J=1.2, 7.6 Hz, 1H), 7.13 (t, J=7.6 Hz, 1H), 3.60 (s, 2H), 3.55 (s, 3H); UPLCMS calculated for C$_{10}$H$_9$NO$_2$ 175.19, observed=175.8 pressure. Crude was purified by silica gel column chromatography by using 20% ethyl acetate in pet ether for elution to get 7.5 g of VIIa.

Step-3: Preparation of VIIb

To a solution of VIIa (2.8 g, 11.48 mmol) in ethanol (50 mL), hydrazine hydrate (99%, 0.5 mL) was added and the mixture was refluxed under nitrogen atmosphere for 30 min. Formed yellow precipitate was isolated by filteration, and suspended in anhydrous ethanol. Potassium tertiary butoxide Synthesis of 1-methyl-2-oxoindoline-7-carbaldehyde, Intermediate VII

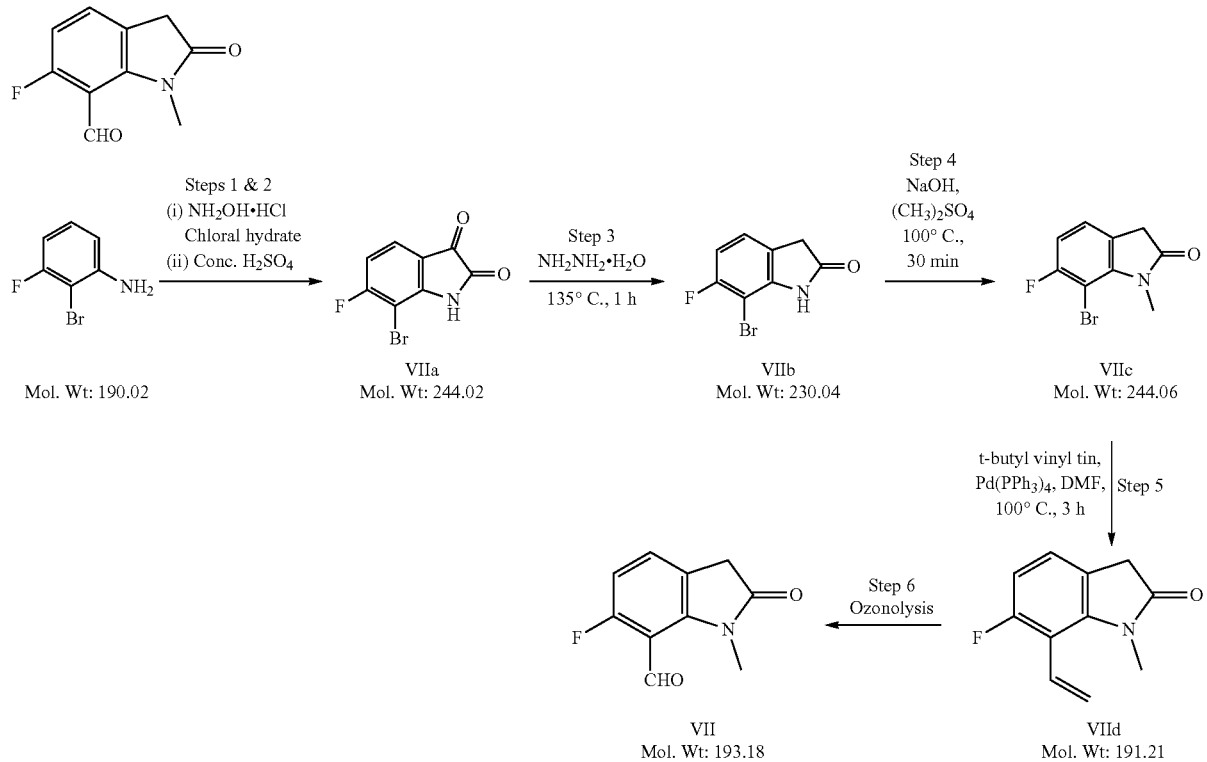

Step-1: Synthesis of VIIa

To a solution of chloral hydrate (9.55 g, 57.89 mmol) in deionized water (150 mL), sodium sulphate (100 g, 684.19 mmol), 3-bromo-2-fluoroaniline (10 g, 52.63 mmol), were added sulphuric acid (40 mL) followed by hydroxylamine hydrochloride (10.97 g, 157.89 mmol) and the whole mixture was heated to 130° C. for 30 min. The mixture was cooled to room temperature, powered on ice-water mixture and extracted with ethylacetate. Organic layer was washed with brine, dried over sodium sulphate and evaporated under reduced pressure. Crude obtained was taken for the next step without any purification.

Step-2

Sulphuric acid (100 mL) was added to the crude obtained in step 1 and the mixture was heated to 70° C. for 1 h. After the complete consumption of starting material, reaction mixture was poured over ice, and extracted with ethyl acetate (2×200 mL). Organic layer was washed with brine, dried over sodium sulphate and evaporated under reduced (4.03 g, 35.90 mmol) was added to the above suspension. The mixture was refluxed for 2 h. After the completion of reaction, mixture was poured over ice-water, acidified with dil. HCl to pH 2. Mixture was extracted with ethyl acetate. Organic layer was washed with brine, dried over sodium sulphate and evaporated under reduced pressure to get crude of VIIb (2.0 g) which was taken for the next step without any purification.

Step-4: Preparation of VIIc

To the suspension of VIIb (1 g, 4.34 mmol) in water (30 mL) and sodium hydroxide (0.397 g, 13.04 mmol) was added dimethyl sulphate (1.4 mL, 13.04 mmol) and the mixture was heated at 100° C. for 2 h. After the consumption of starting material, reaction mixture was cooled to 0° C., added water and extracted with ethyl acetate. Organic layer was washed with brine, dried over sodium sulphate and evaporated under reduced pressure. So, obtained crude was purified by column chromatography by using 21% ethyl acetate in pet-ether to get pure VIIc (0.500 g)

Step-5: Preparation of VIId

To a solution of VIIc (0.500 g, 2.04 mmol) in DMF (10 mL) was added tributylvinyltin (0.65 mL, 2.25 mmol) followed by palladium tetrakis-triphenylphosphine (0.118 g, 0.103 mmol) and the mixture was degassed for 30 min by purging with argon. Reaction was heated to 100° C. for 3 h. After the completion of reaction, mixture was cooled to 0° C., added water and extracted with ethyl acetate. Organic layer was washed with brine, dried over sodium sulphate and evaporated under reduced pressure. So, obtained crude was purified by column chromatography by using 40% dichloromethane in pet-ether to pure VIId (0.300 g).

Step-6: Preparation of VII

Olefin VIId (0.300 g, 1.57 mmol) was dissolved in 10 mL methanol purged with oxygen for 10 min. Mixture was than cooled to −40° C. and ozone was continuously passed through reaction mixture for 30 min. After the complete consumption of VIId, reaction mass was quenched with dimethylsulphide (0.5 mL) and evaporated under reduced pressure to dryness. Residue obtained was purified by column chromatography with eluent 40% ethyl acetate in pet ether to obtain white fluffy solid (0.050 g). $^1$HNMR (400 MHz, CDCl$_3$) δ 10.47 (s, 1H), 7.34-7.37 (m, 1H), 6.78-6.83 (m, 1H), 3.53 (s, 2H), 3.35 (s, 3H); UPLCMS calculated for C$_{10}$H$_8$FNO$_2$ 193.18, observed=194.1

Synthesis of 6-fluoro-1,3,3-trimethyl-2-oxoindoline-7-carbaldehyde, Intermediate VIII

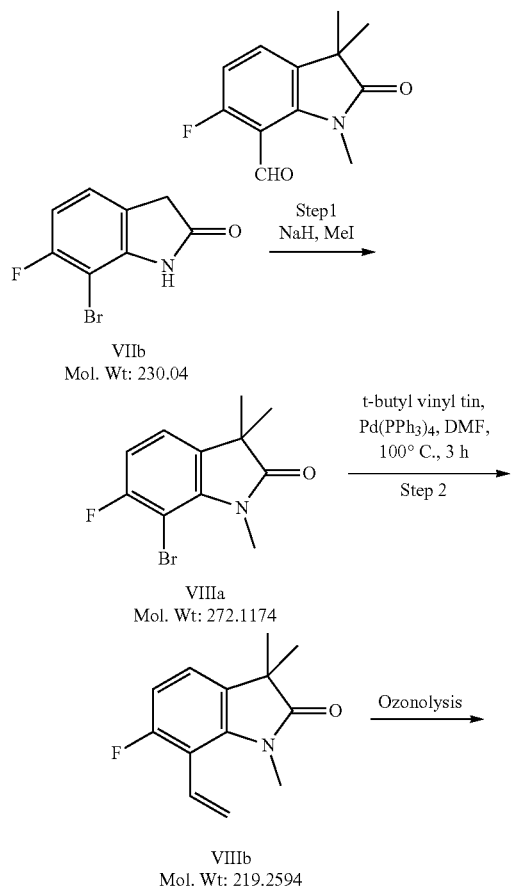

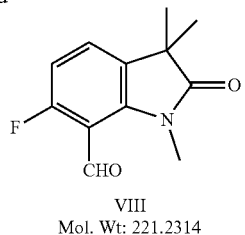

VIII
Mol. Wt: 221.2314

Step-1: Preparation of VIIIa

To the solution of VIIb (0.200 g, 0.869 mmol) in DMF (5 mL) was added sodium hydride (60%, 0.140 g, 3.478 mmol), at 0° C. After stirring at same temperature for 5 min., methyl iodide (2 mL, 3.478 mmol) was introduced slowly, reaction temperature was gradually raised to room temperature and stirred for 2 h. After the completion of reaction, whole reaction mixture was poured slowly on ice-cold water and extracted with ethyl acetate. Crude obtained after solvent evaporation was purified by column chromatography using 10% ethyl acetate in hexane to yield 0.180 g of VIIIa

Step-2: Preparation of VIIIb

To a solution of VIIIa (0.180 g, 0.66 mmol) in DMF (5 mL) was added tributylvinyltin (0.2 mL, 0.727 mmol) followed by palladium tetrakis-triphenylphosphine (0.038 g, 0.033 mmol) and the mixture was degassed for 30 min by purging with argon. Reaction was heated to 100° C. for 3 h. After the completion of reaction, mixture was cooled to 0° C., added water and extracted with ethyl acetate. Organic layer was washed with brine, dried over sodium sulphate and evaporated under reduced pressure. So, obtained crude was purified by column chromatography by using 40% dichloromethane in pet-ether to pure VIIIb (0.080 g)

Step-3: Preparation of VIII

Olefin VIIIb (0.080 g, 3.65 mmol) was dissolved in 5 mL methanol purged with oxygen for 10 min. Mixture was than cooled to −40° C. and ozone was continuously passed through reaction mixture for 30 min. After the complete consumption of VIIIb, reaction mass was quenched with dimethylsulphide (0.5 mL) and evaporated under reduced pressure to dryness. Residue obtained was purified by column chromatography with eluent 40% ethyl acetate in pet ether to obtain white fluffy solid (0.038 g). Structure was confirmed by NMR. $^1$HNMR (400 MHz, CDCl$_3$) δ10.48 (s, 1H), 7.27-7.32 (m, 1H), 6.79-6.84 (m, 1H), 3.36 (s, 3H), 1.38 (s, 6H).

Synthesis of 1-ethyl-6-fluoro-2-oxoindoline-7-carbaldehyde, Intermediate IX

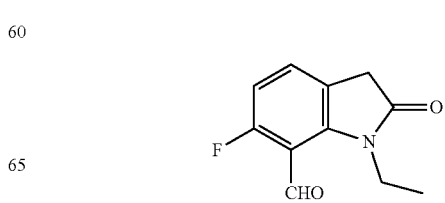

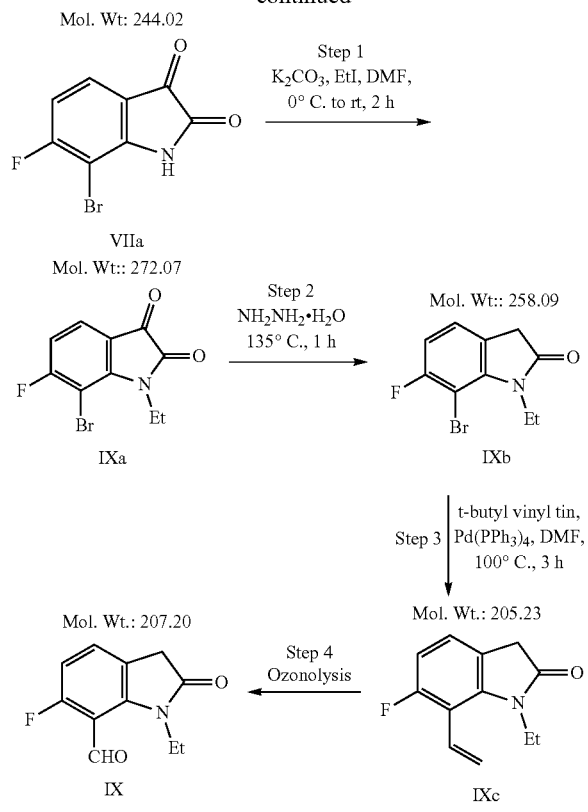

water and extracted with ethyl acetate. Organic layer was washed with brine, dried over sodium sulphate and evaporated under reduced pressure. So, obtained crude was purified by column chromatography by using 40% dichloromethane in pet-ether to pure IXc (0.370 g) LCMS Calculated for $C_{12}H_{12}FNO$ 205.09, Observed=205.8

Step-4: Preparation of IX

Olefin IXc (0.300 g, 1.57 mmol) was dissolved in 10 mL methanol purged with oxygen for 10 min. Mixture was than cooled to −40° C. and ozone was continuously passed through reaction mixture for 30 min. After the complete consumption of, reaction mass was quenched with dimethylsulphide (0.5 mL) and evaporated under reduced pressure to dryness. Residue obtained was purified by column chromatography with eluent 40% ethyl acetate in pet ether to obtain white fluffy solid of aldehyde IX (0.090 g). $^1$HNMR (400 MHz, $CDCl_3$) δ 10.46 (s, 1H), 7.34-7.37 (m, 1H), 6.78-6.83 (m, 1H), 4.13, 4.10 (ABq, J=7.0 Hz, 2H), 3.52 (s, 2H), 1.12 (t, J=7.0 Hz, 1H); UPLCMS calculated for $C_{11}H_{10}FNO_2$ 207.20, observed=208

Synthesis of 2-(6-fluoro-1-methyl-2-oxoindolin-7-yl)acetaldehyde, IntermediateX

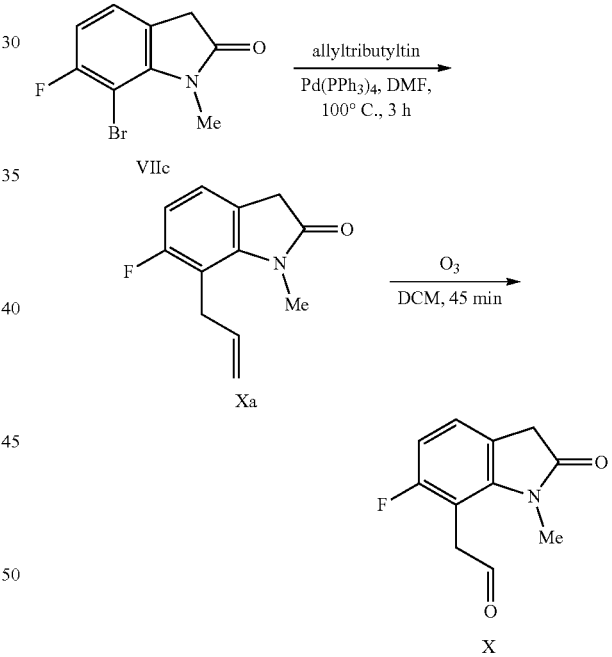

Step-1: Preparation of IXa

To the solution of isatin intermediate VIIa (6.6 g, 27.04 mmol) in DMF (66 mL), were sequentially added $K_2CO_3$ (5.4 g, 39.08 mmol) and ethyl iodide (5.8 mL, 72.51 mmol) at room temperature, under nitrogen atmosphere. After stirring at rt for 2 h, reaction mixture was cooled in ice-bath and water (100 mL) was added. Whole mixture was extracted with ethyl acetate. Organic layer was washed successively with cold water followed by brine and dried over sodium sulphate before evaporating on rotatory evaporator. Obtained crude residue was suspended in n-hexane and stirred for 20 mins. Solid was isolated by filtration to get the intermediate IXa (4.63 g)

Step-2: Preparation of IXb

Hydrazine hydrate (0.5 mL) was added to the solution of intermediate IXa (0.300 g) in ethanol and the mixture was heated in sealed tube to 130° C. After 2 hours, usual aqueous work up was performed to isolate crude solid which was purified by column chromatography with eluent 30% ethylacetate in pet-ether to get 140 mg of compound IXb. UPLC calculated for $C_{10}H_9BrFNO$; 258.09, Observed=258.0.

Step-3: Preparation of IXc

To a solution of IXb (1.0 g, 3.815 mmol) in DMF (20 mL) was added tributylvinyltin (1.3 mL, 4.263 mmol) followed by palladium tetrakis-triphenylphosphine (0.223 g, 0.193 mmol) and the mixture was degassed for 30 min by purging with argon. Reaction was heated to 100° C. for 3 h. After the completion of reaction, mixture was cooled to 0° C., added Step 1: Synthesis of 7-allyl-6-fluoro-1-methylindolin-2-one (Xa)

To a solution of VIIc (0.5 g, 2.049 mmol) in DMF (8 mL) was added allyltributyltin (0.45 mL, 1.45 mmol) followed by tetrakis(triphenylphosphine)palladium (0) (0.15 g, 0.13 mmol) and the mixture was degassed for 30 min by purging with argon. Reaction was heated to 100° C. for 4 h. After the completion of reaction, the mixture was cooled to 0° C., diluted with water and extracted with EtOAc (100 mL). Organic layer was washed with brine, dried over sodium sulphate and evaporated under reduced pressure. The crude was purified by column chromatography on silica gel (230-400 mesh, 15% EtOAc in pet-ether) to pure Xa (0.255 g). UPLC_MS Calc. for $C_{12}H_{12}FNO$, 205.23; Obs. 206.5 [M$^+$+H].

Step 2: Synthesis of 2-(6-fluoro-1-methyl-2-oxoindolin-7-yl)acetaldehyde (X)

Intermediate Xa (0.15 g, 0.731 mmol) was dissolved in 5 mL of DCM and cooled to −78° C. Ozone was continuously passed through reaction mixture for 30 min. After the complete consumption of Xa, reaction mass was quenched with dimethylsulphide (0.2 mL) and evaporated under reduced pressure to dryness. The residue obtained was purified by column chromatography on silica gel (230-400 mesh, 10% ethyl acetate in pet ether) to obtain X (0.125 g). This was characterized by GCMS Calc. for $C_{11}H_{10}FNO_2$, 207.20; Obs. 207.0 [M+].

Intermediate XI, 6-(5-(3-aminopropyl)-2-oxooxazolidin-3-yl)-2H-benzo[b][1,4]oxazin-3(4H)-one (CAS number 1072800-19-1) was synthesized as reported earlier in WO2008126024

Synthesis of 2-(5-fluoro-3-methyl-2-oxo-2,3-dihydrobenzo[d]oxazol-4-yl)acetaldehyde (XII)

product XIIa as a yellow solid. Yield: (3.00 g, 31%); $^1$H NMR (400 MHz, CDCl$_3$): δ 10.38 (s, 1H), 7.90 (d, J=7.6 Hz, 1H), 7.48 (d, J=6.0 Hz, 1H); UPLC-MS: Calc. for $C_6H_3BrFNO_3$ 234.93; Obs. 235.9 [M+H]$^+$.

Step 2: Synthesis of 2-amino-3-bromo-4-fluorophenol (XIIb)

To a stirring solution of XIIa (3.00 g, 12.7 mmol) in methanol (50 mL) was added NiCl$_2$ (3.20 g, 25.4 mmol) and NaBH$_4$ (1.44 g, 38.0 mmol) and allowed to stir at room temperature for 10 minutes. The reaction mixture was filtered and washed with ethyl acetate (200 mL). The filtrate was concentrated to get the crude product XIIb (2.0 gm). The crude was used for the next step without any further purification.

Step 3: Synthesis of 4-bromo-5-fluorobenzo[d]oxazol-2(3H)-one (XIIc)

To a stirring solution of XIIb (2.00 g, 9.70 mmol) in THF (30 mL) was added CDI (2.04 g, 12.6 mmol) and heated to 70° C. for 12 hours. After completion, the reaction mixture was allowed to cool to room temperature and diluted with ethyl acetate (50 mL) and washed with water (2×30 mL).

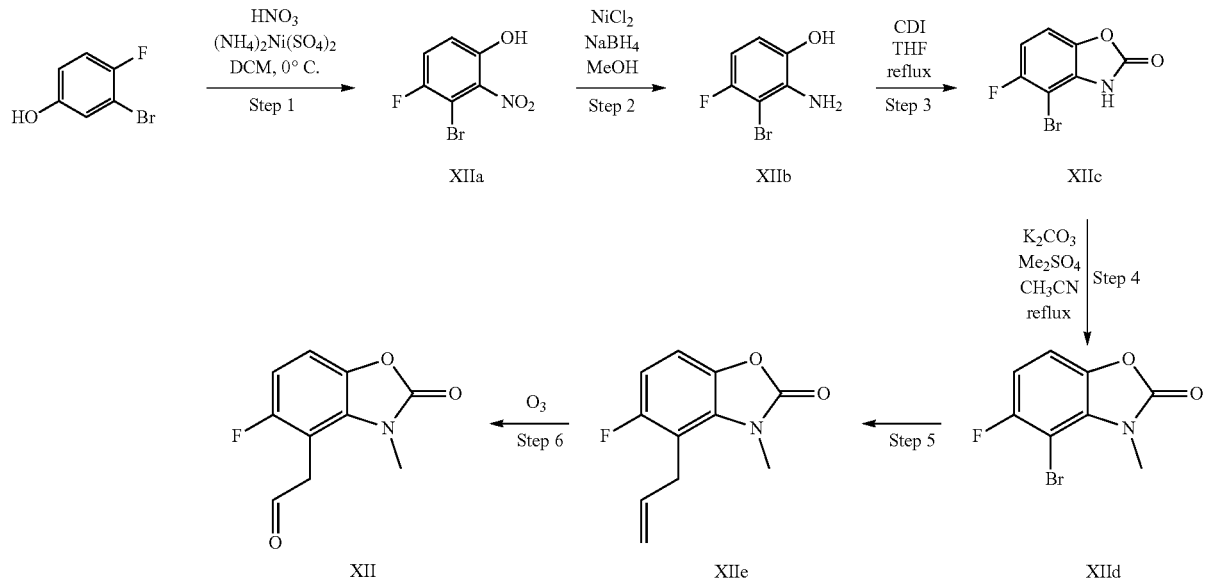

Step 1: Synthesis of 3-bromo-4-fluoro-2-nitrophenol (XIIa)

To a suspension of 3-bromo-4-fluoro phenol (8.00 g, 42.0 mmol) and ammonium nickel-(II)sulfate hexahydrate (8.00 g, 20.5 mmol) in 100 mL of dichloromethane was added 6 mL of nitric acid over 10 minutes while maintaining the internal temperature below 25° C. with an ice bath. The resulting mixture was allowed to stir for 20 minutes and poured into 250 g of crushed ice. The layers were separated and the aqueous phase was extracted with dichloromethane (2×100 mL). The organic layers were combined, washed with brine solution (100 mL), dried over anhydrous Na$_2$SO$_4$ and concentrated under reduced pressure. The residue was purified by flash chromatography using silica gel (60-120 mesh) eluting with 70% dichloromethane in hexane give the The organic layer was dried over Na$_2$SO$_4$ and concentrated under reduced pressure to get the crude product. The crude was purified by column chromatography using silica gel (60-120 mesh) eluting with 25% EtOAc in hexane to afford product XIIc (2.00 g, 67%). H NMR (400 MHz, DMSO-d$_6$): δ 12.02 (brs, 1H), 7.73 (d, J=6.0 Hz, 1H), 7.22 (d, J=8.0 Hz, 1H). LC_MS: Calc. for $C_7H_3BrFNO_2$ 230.93; Obs. 232.0 [M+H]$^+$.

Step 4: Synthesis of 4-bromo-5-fluoro-3-methyl-benzo[d]oxazol-2(3H)-one (XIId)

To a stirring solution of XIIc (1.50 g, 6.50 mmol) in acetonitrile (20 mL) was added K$_2$CO$_3$ (2.69 g, 19.5 mmol) and Me$_2$SO$_4$ (1.70 mL, 19.5 mmol) and the mixture was heated to reflux for 1 hour. The reaction mixture was cooled to room temperature and diluted with ethyl acetate (50 mL) and washed with water (2×30 mL). The organic layer was dried over Na$_2$SO$_4$ and concentrated under reduced pressure to get the crude product, which was purified by column chromatography using silica gel (60-120 mesh) eluting with 25% ethyl acetate in hexane to afford product XIId (1.00 g, 62%); $^1$H NMR (400 MHz, CDCl$_3$): δ 7.40 (d, J=8.0 Hz, 1H), 6.81 (d, J=8.0 Hz, 1H), 3.40 (s, 1H).

Step 5: Synthesis of 4-allyl-5-fluoro-3-methylbenzo[d]oxazol-2(3H)-one (XIIe)

To a solution of XIId (1.00 g, 4.06 mmol) in DMF (20 mL) was added tributylallyltin (1.5 mL, 4.87 mmol) and the mixture was degassed for 30 minutes by purging with nitrogen, followed by added Pd(PPh$_3$)$_4$(0.23 g, 0.20 mmol). The reaction mixture was heated to 100° C. for 8 hours. After completion, the reaction mixture was cooled to 0° C., quenched with water and extracted with ethyl acetate (2×50 mL). The combined organic layers were washed with water (50 mL), brine (50 mL), dried over Na$_2$SO$_4$ and evaporated under reduced pressure to get crude product, which was purified by column chromatography using silica gel (60-120 mesh) eluting with 20% ethyl acetate in petroleum ether to get pure product XIIe (0.45 gm, 53%).

Step 6: Synthesis of 2-(5-fluoro-3-methyl-2-oxo-2,3-dihydrobenzo[d]oxazol-4-yl)acetaldehyde (XII)

To a solution of XIIe (0.30 g, 1.44 mmol) in methanol (10 mL) was purged O$_3$ at −78° C. for 10 minutes. The reaction mixture was quenched with dimethylsulphide (1 mL) and allowed to stir for 30 minutes. The reaction mixture was concentrated and the residue was diluted with ethyl acetate (2×25 mL) and washed with water (20 mL), brine solution (20 mL), dried over Na$_2$SO$_4$ and evaporated under reduced pressure to get crude product XII (0.13 g, crude). The crude was used for the next step without any further purification

Synthesis of 7-(aminomethyl)-6-fluoro-1-methyl-1,3-dihydro-2H-pyrrolo[3,2-b]pyridin-2-one (XIII)

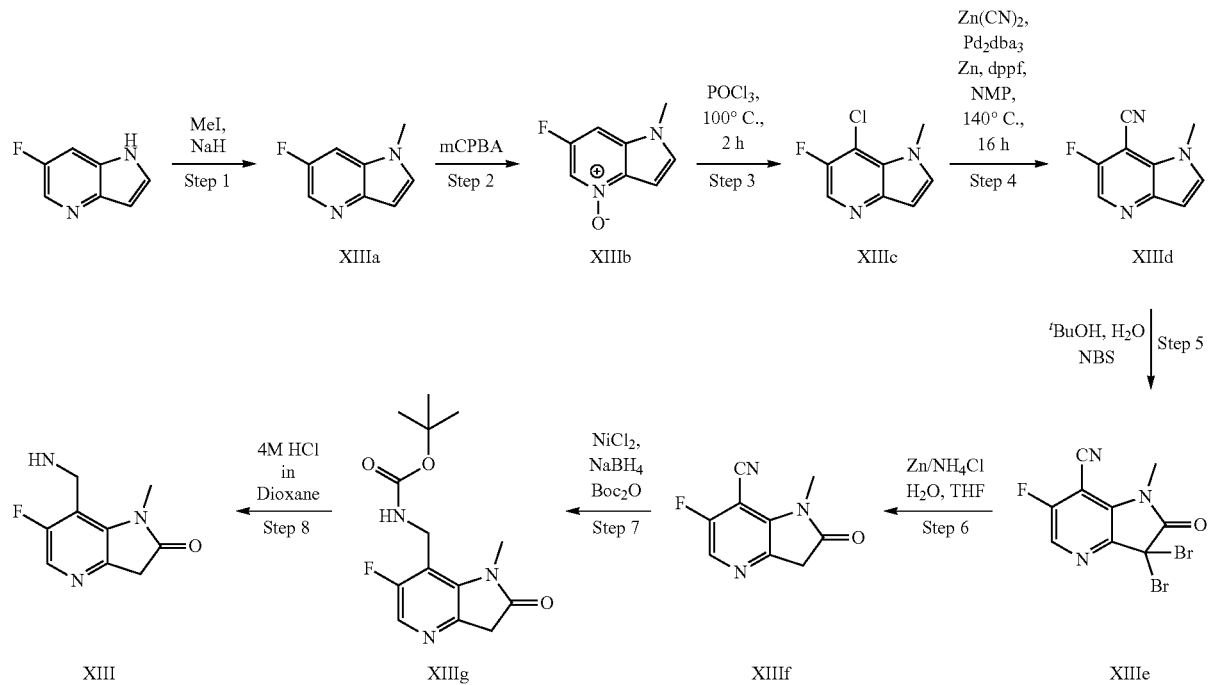
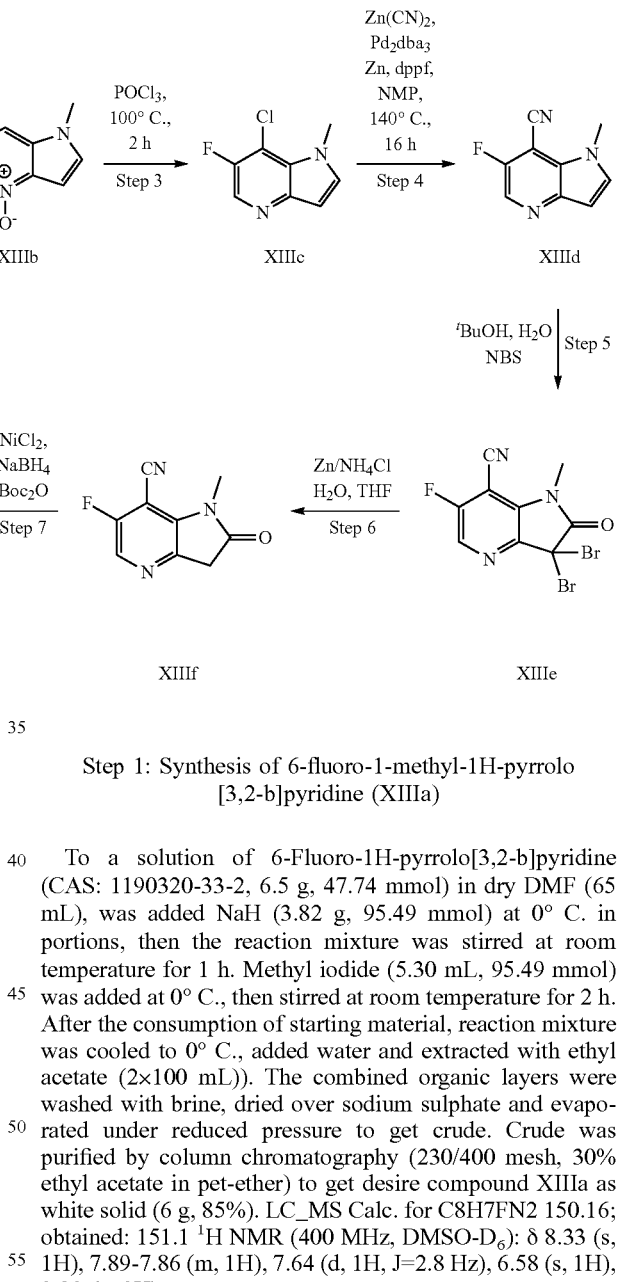

Step 1: Synthesis of 6-fluoro-1-methyl-1H-pyrrolo[3,2-b]pyridine (XIIIa)

To a solution of 6-Fluoro-1H-pyrrolo[3,2-b]pyridine (CAS: 1190320-33-2, 6.5 g, 47.74 mmol) in dry DMF (65 mL), was added NaH (3.82 g, 95.49 mmol) at 0° C. in portions, then the reaction mixture was stirred at room temperature for 1 h. Methyl iodide (5.30 mL, 95.49 mmol) was added at 0° C., then stirred at room temperature for 2 h. After the consumption of starting material, reaction mixture was cooled to 0° C., added water and extracted with ethyl acetate (2×100 mL)). The combined organic layers were washed with brine, dried over sodium sulphate and evaporated under reduced pressure to get crude. Crude was purified by column chromatography (230/400 mesh, 30% ethyl acetate in pet-ether) to get desire compound XIIIa as white solid (6 g, 85%). LC_MS Calc. for C8H7FN2 150.16; obtained: 151.1 $^1$H NMR (400 MHz, DMSO-D$_6$): δ 8.33 (s, 1H), 7.89-7.86 (m, 1H), 7.64 (d, 1H, J=2.8 Hz), 6.58 (s, 1H), 3.80 (s, 3H).

Step 2: Synthesis of 6-fluoro-1-methyl-1H-pyrrolo[3,2-b]pyridine 4-oxide (XIIIb)

To a solution of XIIIa (6 g, 39.95 mmol) in dry DCM (120 mL), was added mCPBA (13.80 g, 79.91 mmol) at 0° C. in portions, then the reaction mixture was stirred at room temperature for 16 h. After the consumption of starting material, reaction mixture was cooled to 0° C., added 10% aq NaHCO$_3$(100 mL) and extracted with DCM (2×100 mL)). The combined organic layers were washed with brine, dried over sodium sulphate and evaporated under reduced pressure to get crude. Crude was washed with n-Hexane (2×100 mL), then dried to get desire compound XIIIb as white solid (4 g, 62%). LC_MS Calc. for $C_8H_7FN_2O$ 166.16; obtained: 167.1; $^1$H NMR (400 MHz, DMSO-D$_6$): δ 8.34-8.33 (m, 1H), 7.71-7.69 (m, 1H), 7.58-7.53 (m, 1H), 6.65 (d, 1H, J=3.2 Hz), 3.81 (s, 3H).

Step 3: Synthesis of 7-chloro-6-fluoro-1-methyl-1H-pyrrolo[3,2-b]pyridine (XIII c)

POCl$_3$ (40 mL), was added to a compound XIIIb (4 g, 24.07 mmol) drop wise at 0° C., then the reaction mixture was heated at 100° C. for 2 h. After the consumption of starting material, reaction mixture was cooled to 0° C., added 10% aq NaHCO$_3$(100 mL) in drop wise and extracted with ethyl acetate (2×100 mL)). The combined organic layers were washed with brine, dried over sodium sulphate and evaporated under reduced pressure to get crude. Crude was purified by column chromatography (230/400 mesh, 30% ethyl acetate in pet-ether) to get desire compound XIIIc as white solid (2 g, 45%). LC_MS Calc. for $C_8H_6ClFN_2$ 184.60; obtained: 185.2; $^1$H NMR (400 MHz, DMSO-D$_6$): δ 8.43 (s, 1H), 7.71 (s, 1H), 6.63 (d, 1H, J=3.6 Hz), 4.09 (s, 3H).

Step 4: Synthesis of 6-fluoro-1-methyl-1H-pyrrolo[3,2-b]pyridine-7-carbonitrile (XIII d)

To a solution of XIIIc (2 g, 10.83 mmol) in NMP (40 mL), was added zinc dust (14 mg, 0.21 mmol), Pd2dba3 (0.20 g, 0.21 mmol) and DPPF (0.24 g, 0.43 mmol) at 0° C., then the reaction mixture was purged with N2 for 15 min, then Zinc cyanide (2.54 g, 21.66 mmol) was added and the reaction mixture was heated at 130° C. for 24 h. After the consumption of starting material, reaction mixture was diluted with water (100 mL) and extracted with ethyl acetate (2×100 mL)). The combined organic layers were washed with brine, dried over sodium sulphate and evaporated under reduced pressure to get crude. Crude was purified by column chromatography (230/400 mesh, 30% ethyl acetate in pet-ether) to get desire compound XIIId as white solid (1 g, 57%). LC_MS Calc. for $C_9H_6FN_3$ 175.17; obtained: 176.2; $^1$H NMR (400 MHz, DMSO-D$_6$): δ 8.60 (s, 1H), 7.87-7.86 (m, 1H), 6.78-6.76 (m, 1H), 4.05 (s, 3H).

Step 5: Synthesis of 3,3-dibromo-6-fluoro-1-methyl-2-oxo-2,3-dihydro-1H-pyrrolo[3,2-b]pyridine-7-carbonitrile (XIIIe)

To a solution of XIIId (1 g, 5.70 mmol) in tert-Butanol (30 mL) and water (30 mL) was added N-Bromo succinimide (2.03 g, 11.40 mmol) in portions. Then the reaction mixture was stirred at room temperature for 1 h. After the consumption of starting material, reaction mixture was diluted with water (100 mL) and extracted with ethyl acetate (2×100 mL)). The combined organic layers were washed with brine, dried over sodium sulphate and evaporated under reduced pressure to get crude. The resultant crude was washed with n-hexane to get pure compound XIIIe as pale yellow solid (1 g, 57%). LC_MS Calc. for $C_9H_4Br_2FN_3O$ 348.96; obtained: 349.7; $^1$H NMR (400 MHz, DMSO-D6): δ 8.49 (s, 1H), 3.52 (s, 3H).

Step 6: Synthesis of 6-fluoro-1-methyl-2-oxo-2,3-dihydro-1H-pyrrolo[3,2-b]pyridine-7-carbonitrile (XIIIf)

To a solution of XIIIe (1 g, 2.86 mmol) in dry THF (10 mL) and aq.sat. Ammonium chloride solution (10 mL) was added Zinc dust (3.74 g, 57.31 mmol) in portions. Then the reaction mixture was stirred at room temperature for 16 h. After the consumption of starting material, reaction mixture was filtered through celite, diluted with water (100 mL) and extracted with ethyl acetate (2×100 mL)). The combined organic layers were washed with brine, dried over sodium sulphate and evaporated under reduced pressure to get crude. The resultant crude was washed with n-hexane to get pure compound XIIIf as pale yellow oil (0.5 g, 91%). LC_MS Calc. for $C_9H_6FN_3O$ 191.17; obtained: 192.0; $^1$H NMR (400 MHz, DMSO-D$_6$): δ 8.22 (s, 1H), 3.71 (s, 2H), 3.44 (s, 3H).

Step 7: Synthesis of tert-butyl ((6-fluoro-1-methyl-2-oxo-2,3-dihydro-1H-pyrrolo[3,2-b]pyridin-7-yl)methyl)carbamate (XIIIg)

To a solution of XIIIf (0.50 g, 2.61 mmol) in dry Methanol (10 mL) was added Boc anhydride (0.7 mL, 3.13 mmol) and Nickel chloride (0.680 g, 5.23 mmol), then the reaction mixture was cooled to 0° C., NaBH4 (0.297 g, 7.84 mmol) in portions. Then the reaction mixture was stirred at room temperature for 30 min. After the consumption of starting material, reaction mixture was filtered through celite, diluted with water (20 mL) and extracted with ethyl acetate (2×50 mL)). The combined organic layers were washed with brine, dried over sodium sulphate and evaporated under reduced pressure to get crude. Crude was purified by column chromatography (230/400 mesh, 30% ethyl acetate in pet-ether) to get desire compound XIIIg as white solid (0.35 g, 50%). LC_MS Calc. for $C_{14}H_{18}FN_3O_3$ 295.31; obtained: 296.2; $^1$H NMR (400 MHz, DMSO-D$_6$): δ 11.06 (s, 2H), 8.08-8.06 (m, 1H), 7.45-7.40 (m, 1H), 4.38 (s, 2H), 3.65-3.64 (m, 2H), 2.56 (s, 9H).

Step 8: Synthesis of 7-(aminomethyl)-6-fluoro-1-methyl-1,3-dihydro-2H-pyrrolo[3,2-b]pyridin-2-one (XIII)

To a solution of XIIIf (0.35 g, 1.18 mmol) in dry DCM (7 mL) was added 4M HCl in 1,4-dioxane (2 mL) at 0° C., then the reaction mixture was stirred at room temperature for 1 h. After the consumption of starting material, reaction mixture was concentrate to dryness. The crude was dissolved in dry Methanol (10 mL) neutralized by adding Amberlyst A26 resin at 0° C., filtered and evaporated under reduced pressure to get crude. The resultant crude was washed with n-hexane to get XIII as pale yellow oil (0.20 g, 90%) and the product is taken next without further characterization.

Example 1: 6-(5-(2-(((1-Methyl-2-oxoindolin-7-yl)methyl)amino)ethyl)-2-oxooxazolidin-3-yl)-2H-pyrido[3,2-b][1,4]oxazin-3(4H)-one

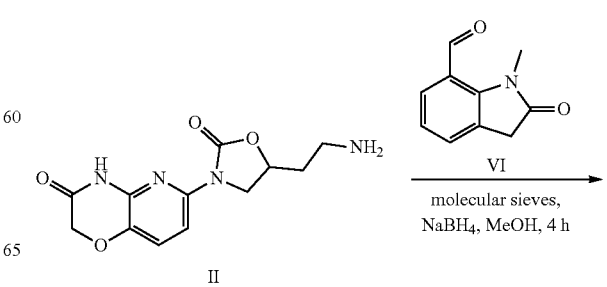

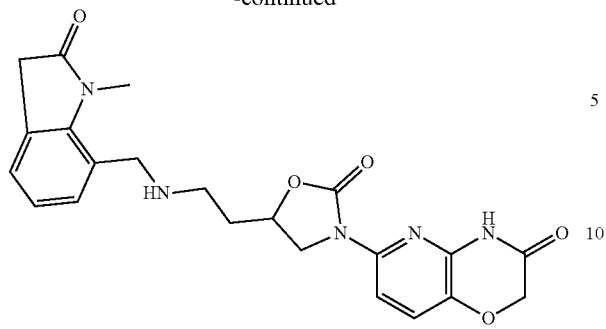

Example 1

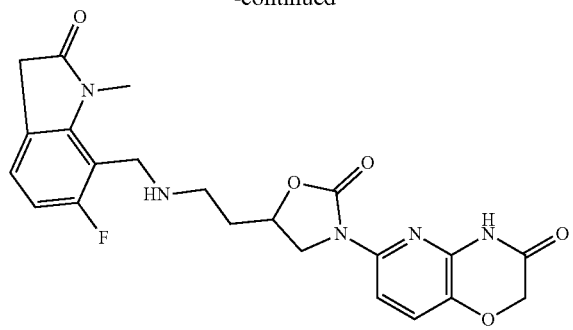

Example 2

-continued

To a stirred solution of 6-(5-(2-aminoethyl)-2-oxooxazo-lidin-3-yl)-2H-pyrido[3,2-b][1,4]oxazin-3(4H)-one II (45 mg, 0.161 mmol) and 1-methyl-2-oxoindoline-7-carbaldehyde VI (29 mg, 0.00018 mol) in Dichlormethane:methanol (9:1=5 ml), molecular sieves (0.1 g) was added and stirred at 25° C. for 2 hours. After confirmation of imine generation by $^1$H NMR, it was filtered and concentrated in vacuo. Residue obtained was dissolved in methanol, cooled to 0° C., and sodium borohydride (12 mg, 0.322 mmol) was added. Reaction was gradually warmed to 25° C. and stirred for 2 hours. After completion of reaction, the reaction mixture was quenched by water and concentrated in vacuo to remove methanol. Residual mixture was extracted with ethyl acetate. The combined organic layer was washed with water followed by brine, dried over sodium sulphate and concentrated in vacuo. The crude was purified by mass based preparative purification to afford title compound (3 mg) as a white solid. $^1$H NMR (400 MHz, MeOD) δ 8.52 (bs, 1H), 7.70 (d, 8.8 Hz, 1H), 7.367 (dd, 1H, J=8.8 Hz, 0.8 Hz, 1H), 7.28 (d, J=7.6 Hz, 2H), 7.07 (t, J=7.6 Hz, 1H), 4.82 (m, 1H), 4.64 (s, 2H), 4.32 (t, J=9.6 Hz, 1H), 3.89-3.93 (m, 1H), 3.57 (s, 3H), 3.03-3.09 (m, 1H), 2.18 (s, 2H), 2.01-2.08 (m, 2H). LCMS=Calculated for $C_{22}H_{23}N_5O_5$, 437.56, Observed=438, HPLC=89.04% (HPLC Column: ATLANTIS dC18(250×4.6)mm, 5µ, Mobile Phase A: 0.1% TFA in water, Mobile Phase B: Acetonitrile.

Example 2: 6-(5-(2-(((6-Fluoro-1-methyl-2-oxoindolin-7-yl)methyl)amino)ethyl)-2-oxooxazolidin-3-yl)-2H-pyrido[3,2-b][1,4]oxazin-3(4H)-on To a stirred solution of 6-(5-(2-aminoethyl)-2-oxooxazo-lidin-3-yl)-2H-pyrido[3,2-b][1,4]oxazin-3(4H)-one, II (0.26 g, 0.0009 mol) and 6-fluoro-1-methyl-2-oxoindoline-7-carbaldehyde, VII (0.198 g, 0.0010 mol) in methanol (5 ml), glacial acetic acid (0.2 ml) and stirred at 25° C. for 2 hours. Then, cooled to 0° C., sodium cyano borohydride resin (0.0011 mol) was added and stirred at 25° C. for 2 hours. After completion of reaction, the reaction mixture was filtered to remove the resin and the filtrate was concentrated in vacuo. It was purified by reverse phase preparative HPLC to get pure compound colourless solid of 6-(5-(2-(((5-fluoro-1-methyl-2-oxoindolin-4-yl)methyl)amino)ethyl)-2-oxooxazolidin-3-yl)-2H-pyrido[3,2-b][,4]oxazin-3(4H)-one (90 mg, 21.27%). $^1$H NMR (400 MHz, MeOD) δ=7.71-7.73 (m, 1H), 7.38-7.42 (m, 2H), 6.95-7.00 (m, 1H), 4.82-4.89 (m, 1H), 4.64-4.67 (m, 4H), 4.38-4.43 (m, 1H), 3.91-3.96 (m, 1H), 3.54 (s, 2H), 3.61 (s, 3H), 3.42-3.49 (m, 2H), 2.23-2.29 (m, 2H). LCMS calculated for $C_{22}H_{22}FN_5O_5$ 455.16, observed=456.01, HPLC=99.69% (HPLC Column: ATLANTIS dC18(250×4.6)mm, 5µ, Mobile Phase A: 0.1% TFA in water, Mobile Phase B: Acetonitrile.

Example 3: 6-(5-(2-(((6-fluoro-1-methyl-2-oxoindolin-7-yl)methyl)amino)ethyl)-2-oxooxazolidin-3-yl)-2H-benzo[b][1,4]oxazin-3(4H)-one

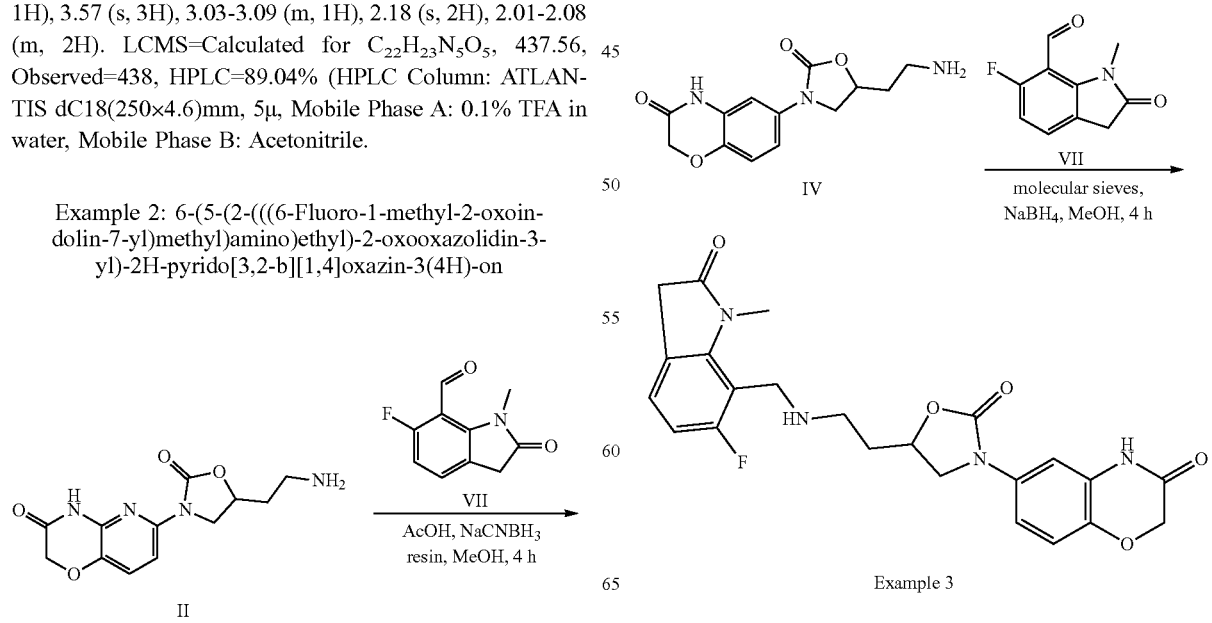

Example 3

To a stirred solution of IV (40 mg, 0.144 mmol) and oxoindole VII (29 mg, 0.00018 mol) in dichlormethane:methanol (9:1=5 ml), molecular sieves (0.1 g) was added and stirred at 25° C. for 2 hours. After confirmation of imine generation by $^1$H NMR, it was filtered and concentrated in vacuo. Residue obtained was dissolved in methanol, cooled to 0° C., and sodium borohydride (12 mg, 0.322 mmol) was added. Reaction was gradually warmed to 25° C. and stirred for 2 hours. After completion of reaction, the reaction mixture was quenched by water and concentrated in vacuo to remove methanol. Residual mixture was extracted with ethyl acetate. The combined organic layer was washed with water followed by brine, dried over sodium sulphate and concentrated in vacuo. The crude was purified by mass based preparative purification to afford title compound (13 mg) as a white solid. $^1$H NMR (400 MHz, MeOD) 7.36-7.43 (m, 1H), 7.36-7.37 (m, 1H), 6.95-7.03 (m, 3H), 4.83-4.86 (m, 1H), 4.66 (s, 2H), 4.57 (s, 2H), 4.24 (t, J=8.8 Hz, 1H), 3.79-3.83 (m, 1H), 3.70 (s, 2H), 3.54 (s, 3H), 3.42-3.48 (m, 2H), 2.26-2.31 (m, 2H); LCMS calculated for $C_{23}H_{23}FN_4O_5$, 454.6 observed 455.

Example 4: Synthesis of 6-(5-(2-(((6-fluoro-1,3,3-trimethyl-2-oxoindolin-7-yl)methyl)amino)ethyl)-2-oxooxazolidin-3-yl)-2H-pyrido[3,2-b][1,4]oxazin-3(4H)-one

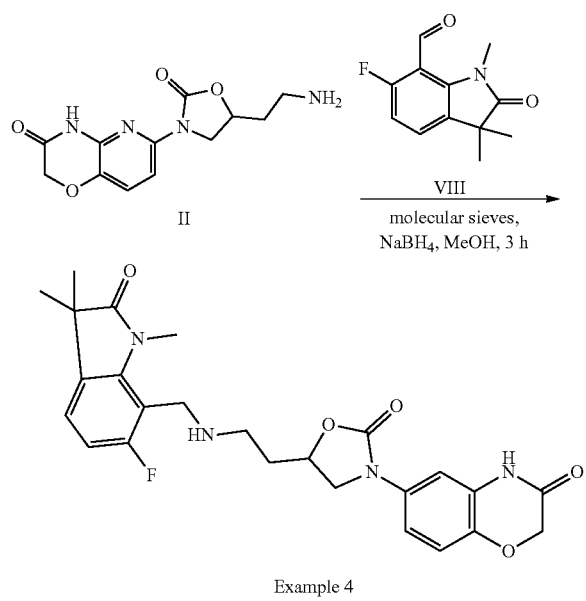

Example 4

To a stirred solution of 6-(5-(2-aminoethyl)-2-oxooxazolidin-3-yl)-2H-pyrido[3,2-b][1,4]oxazin-3(4H)-one, II (0.045 g, 0.00016 mol) and 6-fluoro-1,3,3-trimethyl-2-oxoindoline-7-carbaldehyde, VIII (0.035 g, 0.00016 mol) in Dichlormethane:methanol (9:1=5 ml), molecular sieves (0.1 g) was added and stirred at 25° C. for 2 hours. After confirmation of imine generation by $^1$H NMR, reaction mixture was filtered through celite and filtrate was concentrated under reduced pressure. Resulting residue was dissolved in methanol, cooled to 0° C., and sodium borohydride (0.012 g, 0.00033 mol) was added. After the completion of addition, reaction was gradually warmed to room temperature and stirred for 1 hour. After completion of reaction, the reaction mixture was quenched by water and concentrated in vacuo to remove methanol. It was extracted with ethyl acetate and water. The separated organic layer was washed with brine, dried over sodium sulphate and concentrated in vacuo. It was purified by column chromatography on silica gel with gradient elution of 4-5% methanol in dichloromethane to obtain white solid of 6-(5-(2-(((6-fluoro-1,3,3-trimethyl-2-oxoindolin-7-yl)methyl)amino)ethyl)-2-oxooxazolidin-3-yl)-2H-pyrido[3,2-b][1,4]oxazin-3(4H)-one (21 mg, 21.27%). $^1$H NMR (400 MHz, MeOD) δ 7.58-7.69 (m, 1H), 7.35-7.37 (m, 1H), 7.21-7.24 (m, 1H), 4.79-4.80 (m, 1H), 4.633 (s, 2H), 4.293-4.297 (m, 1H), 4.27 (s, 2H), 3.89-3.92 (m, 1H), 3.37 (s, 3H), 2.88-2.91 (m, 2H), 2.00-2.04 (m, 2H), 1.30 (s 6H). LCMS Calculated for $C_{24}H_{26}FN_5O_5$, 483.50, Observed=484.5 HPLC=92.99% (HPLC Column: ATLANTIS dC18(250×4.6) mm, 5μ, Mobile Phase A: 0.1% TFA in water, Mobile Phase B: Acetonitrile.

Example 5: Synthesis of 5-(5-(2-(((6-Fluoro-1-methyl-2-oxoindolin-7-yl)methyl)amino)ethyl)-2-oxooxazolidin-3-yl)-2-methylnicotinonitrile

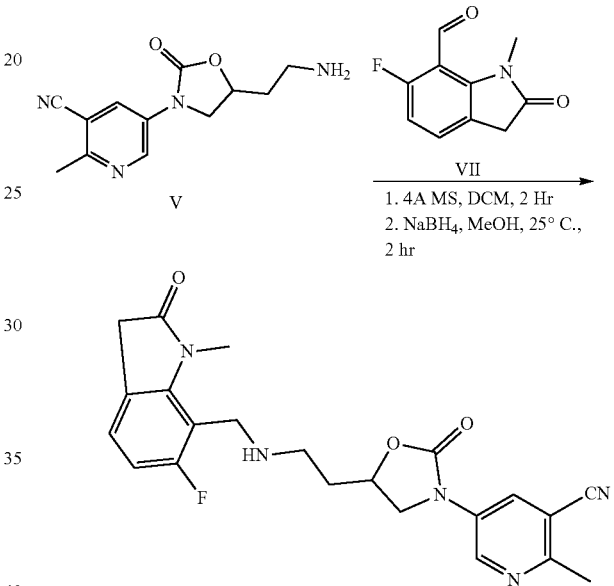

Example 5

To a stirred solution of 6-(5-(2-aminoethyl)-2-oxooxazolidin-3-yl)-2H-pyrido[3,2-b][1,4]oxazin-3(4H)-one, V (43 mg, 0.174 mmol) and 6-fluoro-1-methyl-2-oxoindoline-7-carbaldehyde (VII; 35 mg, 0.183 mmol) in Dichlormethane:methanol (9:1=5 ml), molecular sieves (0.1 g) was added and stirred at 25° C. for 2 hours. After confirmation of imine generation by $^1$H NMR, it was filtered and concentrated in vacuo. It was dissolved in methanol, cooled to 0° C., sodium borohydride (12 mg, 0.348 mmol) was added and stirred at 25° C. for 1.5 hours. After completion of reaction, the reaction mixture was quenched by water and concentrated in vacuo to remove methanol. It was extracted with ethyl acetate and water. The separated organic layer was washed with brine, dried over sodium sulphate and concentrated in vacuo. It was purified by reverse phase preparative HPLC to get pure compound colourless solid of 5-(5-(2-(((6-fluoro-1-methyl-2-oxoindolin-7-yl)methyl)amino)ethyl)-2-oxoxazolidin-3-yl)-2-methylnicotinonitrile, BWC0136 (6 mg, 8%). purification. $^1$H NMR (400 MHz, MeOD) δ=8.89 (d, J=2.8 Hz, 1H), 8.36 (d, J=2.8 Hz, 1H), 7.25-7.29 (m, 1H), 6.84-6.88 (m, 1H), 4.488-4.492 (m, 1H), 4.22-4.26 (m, 3H), 3.85-3.89 (m, 1H), 3.52-3.60 (m, 4H), 3.06-3.11 (m, 2H), 2.72 (s, 3H), 2.12-2.17 (m, 2H); LCMS=Calculated for $C_{22}H_{22}FN_5O_3$, 423.45, Observed=424. HPLC=94.92% (HPLC Column: ATLANTIS dC18(250×4.6) mm, 5μ, Mobile Phase A: 0.1% TFA in water, Mobile Phase B: Acetonitrile).

Example 6: 6-(5-(3-(((6-fluoro-1-methyl-2-oxoindolin-7-yl)methyl)amino)propyl)-2-oxooxazolidin-3-yl)-2H-pyrido[3,2-b][1,4]oxazin-3(4H)-one

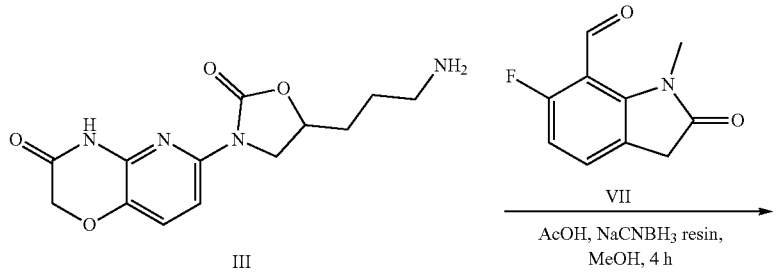

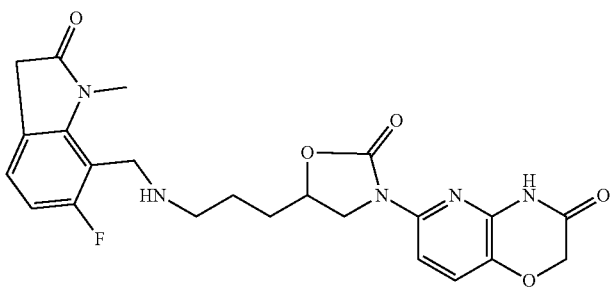

Example 6

To a stirred solution of starting material, III (0.02 g, 0.068 mmol) in DCM/MeOH (9/1, 5 ml) was added aldehyde, VII (13.15 mg, 0.068 mmol), followed by molecular sieves (50 mg), and triethyl amine (few drops). The resulting reaction mixture was stirred at RT for 3 h. After confirming the formation of imine by $^1$H-NMR, the reaction mixture was filtered and concentrated under reduced pressure. The residue was dissolved in methanol, cooled to 0° C. and sodium cyanoborohydride (5 mg, 0.136 mmol) was added. After stirring at RT for 2 h, the reaction mixture was concentrated on rotary evaporator. Obtained residue was diluted with water and extracted with ethyl acetate. The crude was purified by mass based preparative purification to afford title compound (5 mg) as a pale yellow liquid. $^1$H NMR (400 MHz, MeOD) δ 8.44 (bs, 1H), 7.70 (d, J=8.6 Hz, 1H), 7.36 (d, J=8.6 Hz, 1H), 7.30-7.34 (m, 1H), 6.87-6.92 (m, 1H), 4.74-4.76 (m, 1H), 4.63 (s, 2H), 4.39 (s, 2H), 4.31-4.36 (m, 1H), 3.84-3.88 (m, 1H), 3.67-3.70 (m, 2H), 3.54-3.58 9 m, 5H), 3.08-3.10 (m, 2H), 1.84-1.90 (m, 4H); LCMS calculated for $C_{23}H_{24}FN_5O_5$, 469.47 Observed=470.0; HPLC=87.33% (Zorbax Eclipse plus C18 RRHD (50×2.1) mm, 1.8μ; Mobile phase A: 0.1% TFA in WaterB: Acetonitrile)

Example 7: 6-(5-(2-(((1-Ethyl-6-fluoro-2-oxoindolin-7-yl)methyl)amino)ethyl)-2-oxooxazolidin-3-yl)-2H-pyrido[3,2-b][1,4]oxazin-3(4H)-one

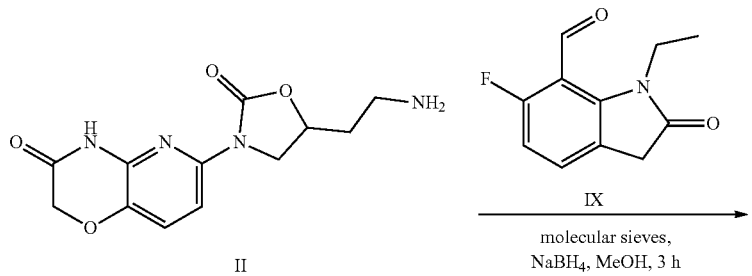

-continued

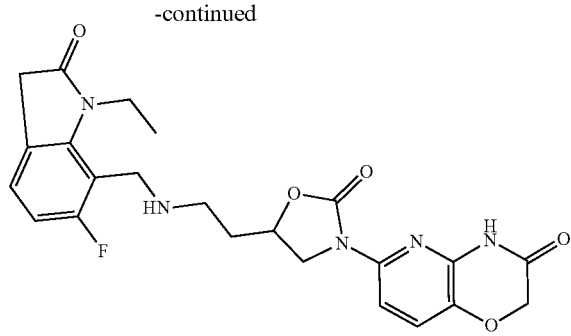

Example 7

To a stirred solution of II (30 mg, 0.108 mmol) and oxoindole IX (23 mg, 0.113 mol) in dichlormethane:methanol (9:1=5 ml), molecular sieves (0.1 g) was added and stirred at 25° C. for 2 hours. After confirmation of imine generation by $^1$H NMR, it was filtered and concentrated in vacuo. Residue obtained was dissolved in methanol, cooled to 0° C., and sodium borohydride (8 mg, 0.2162 mmol) was added. Reaction was gradually warmed to 25° C. and stirred for 2 hours. After completion of reaction, the reaction mixture was quenched by water and concentrated in vacuo to remove methanol. Residual mixture was extracted with ethyl acetate. The combined organic layer was washed with water followed by brine, dried over sodium sulphate and concentrated in vacuo. The crude was purified by mass based preparative purification to afford title compound, (7.2 mg) as a white solid. H NMR (400 MHz, MeOD) 8.35 (bs, 1H), 7.69 (d, J=8.6 Hz, 1H), 7.36 (d, J=8.6 Hz, 1H), 7.33-7.30 (m, 1H), 6.92-6.87 (m, 1H), 4.84-4.82 (m, 1H), 4.33 (t, J=8.8 Hz, 1H), 4.23 (s, 2H), 4.02-4.08 (m, 2H), 3.89-3.93 (m, 1H), 3.53-3.70 (m, 2H), 3.13-3.16 (m, 2H), 2.68 (s, 1H), 2.12-2.14 (d, 2H), 1.27-1.31 (m, 2H); LCMS calculated for $C_{24}H_{25}FN_4O_5$, 469.47 observed 470.

Example 8: 6-(5-(3-(((1-Ethyl-6-fluoro-2-oxoindolin-7-yl)methyl)amino)propyl)-2-oxooxazolidin-3-yl)-2H-pyrido[3,2-b][1,4]oxazin-3(4H)-one

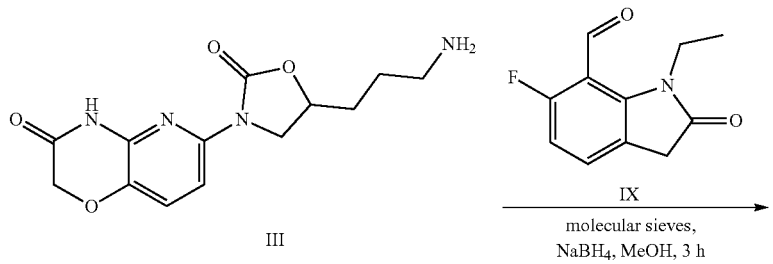

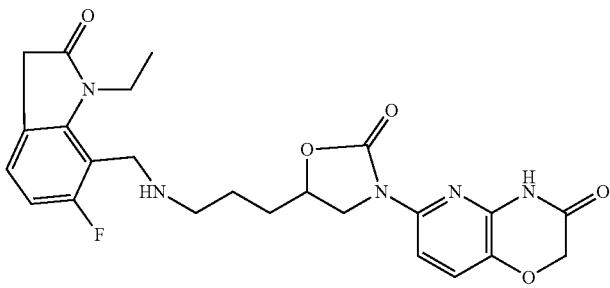

Example 8

To a stirred solution of III (20 mg, 0.0684 mmol) and oxoindole IX (15 mg, 0.0724 mol) in dichlormethane:methanol (9:1=5 ml), molecular sieves (0.1 g) was added and stirred at 25° C. for 2 hours. After confirmation of imine generation by ¹H NMR, it was filtered and concentrated in vacuo. Residue obtained was dissolved in methanol, cooled to 0° C., and sodium borohydride (8 mg, 0.2162 mmol) was added. Reaction was gradually warmed to 25° C. and stirred for 2 hours. After completion of reaction, the reaction mixture was quenched by water and concentrated in vacuo to remove methanol. Residual mixture was extracted with ethyl acetate. The combined organic layer was washed with water followed by brine, dried over sodium sulphate and concentrated in vacuo. The crude was purified by mass based preparative purification to afford title compound, (3.3 mg) as a white solid. ¹H NMR (400 MHz, MeOD) 8.28 (bs, 1H), 7.71 (d, J=8.8 Hz, 1H), 736-7.41 (m, 2H), 6.93-6.98 (m, 1H), 4.75-4.78 (m, 1H), 4.64 (s, 2H), 4.40 (s, 2H), 4.33-4.37 (m, 1H), 3.98-4.03 (m, 2H), 3.85-3.89 (m, 1H), 3.56-3.59 (m, 1H), 3.22 (t, J=6.8 Hz, 2H); LCMS calculated for C$_{25}$H$_{27}$FN$_4$O$_5$, 483.5 observed 484.

Example 9: Chiral 6-(5-(3-(((6-fluoro-1-methyl-2-oxoindolin-7-yl)methyl)amino)propyl)-2-oxooxazolidin-3-yl)-2H-pyrido[3,2-b][1,4]oxazin-3(4H)-one (Enantiomer 1)

Example 10: Chiral 6-(5-(3-(((6-fluoro-1-methyl-2-oxoindolin-7-yl)methyl)amino)propyl)-2-oxooxazolidin-3-yl)-2H-pyrido[3,2-b][1,4]oxazin-3(4H)-one (Enantiomer2)

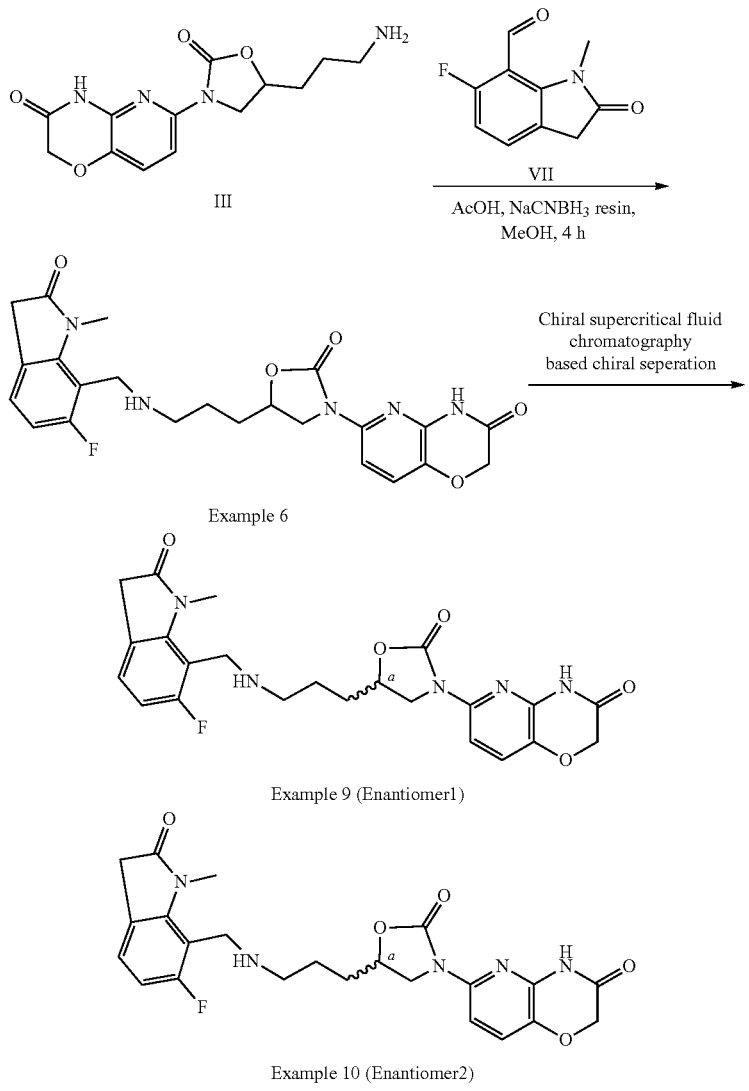

a = Absolute configuration unknown

To a stirred solution of III (4.95 g, 0.025 mol) in MeOH (370 mL), glacial acetic acid (10 mL) was added was added aldehyde, VII (4.825, 0.025 mol) and stirred at 25° C. for 15 min. The solution was then, cooled to 0° C. followed by addition of sodium cyanoborohydride resin (20 g, 0.050 mol) and stirred at 25° C. for 6 h. After completion of reaction, the reaction mixture was filtered to remove the resin and the filtrate was concentrated in vacuo. It was purified by flash column chromatography on silica gel (230-400 mesh, 8% MeOH in DCM to get the racemic Example 6 as a pale yellow solid (2.52 g, 21.48%). $^1$H NMR (400 MHz, CD$_3$OD). δ 7.71 (d, J=8.40 Hz, 1H), 7.37-7.43 (m, 2H), 7.0-6.94 (m, 1H), 4.87 (m, 1H), 4.79-4.7 (m, 1H), 4.7-4.6 (m, 4H), 4.34-4.39 (m, 1H), 3.9-3.8 (m, 1H), 3.61 (s, 2H), 3.52 (s, 3H), 1.91-1.97 (m, 4H). LC_MS calculated for C$_{23}$H$_{24}$FN$_5$O$_5$ 469.47, observed=470.01. HPLC=96.84% (HPLC Column: ATLANTIS dC18(250×4.6) mm, 5µ, Mobile Phase A: 0.1% TFA in water, Mobile Phase B: Acetonitrile.

The Part of racemic compound (Example 6, 2 gm) was separated into its enantiomers (Example 9 and Example 10) by Chiral supercritical fluid chromatography (SFC) using the following SCF conditions
Column: Lux C$_3$ (250*30) mm
Mobile phase: CO$_2$: 20 mm Ammonia in Methanol (65:35)
Total flow: 100 g/min
Injection volume: 0.5 ml
Back Pressure: 100 bar
Wave length: 212 nm
Cycle time: 11.0 min Two pure fractions were collected and their solvents were evaporated under vacuo afforded enantiomer1 and 2 as off white solid.
Enantiomer 1 (Example 9): 0.750 gm, Chiral HPLC retention time: 5.74 min.
Enantiomer 2 (Example 10): 0.650 gm, Chiral HPLC retention time: 7.38 min.

Example 11: 6-(5-(2-((2-(6-fluoro-1-methyl-2-oxoindolin-7-yl)ethyl)amino)ethyl)-2-oxooxazolidin-3-yl)-2H-pyrido[3,2-b][1,4]oxazin-3(4H)-one

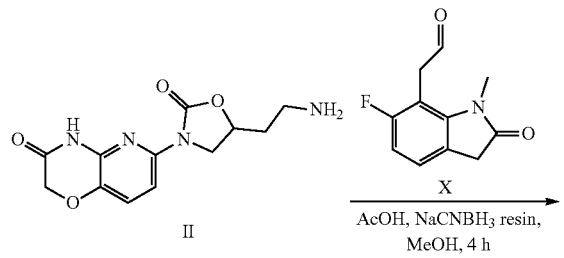

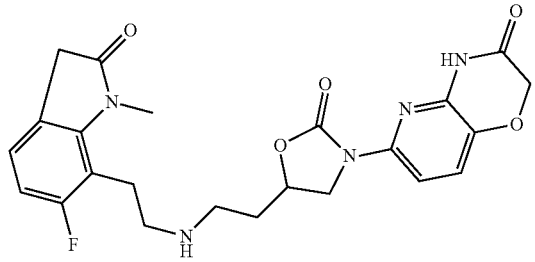

Example 11

To a stirred solution of amine II (0.13 g, 0.467 mmol) and aldehyde X (0.125 g, 0.603 mmol) in MeOH (4 mL), glacial acetic acid (0.2 mL) was added and stirred at 25° C. for 15 min. The solution was then, cooled to 0° C. followed by addition of sodium cyanoborohydride resin (0.125 g) and stirred at 25° C. for 2 h. After completion of reaction, the reaction mixture was filtered to remove the resin and the filtrate was concentrated in vacuo. It was purified by reverse phase preparative HPLC to get Example 11 as a pale yellow solid (21 mg). $^1$H NMR (400 MHz, DMSO-d$_6$). δ 11.22 (s, 1H), 8.77 (brs, 2H), 7.61 (d, 1H, J=8.40 Hz), 7.45 (d, 1H J=8.40 Hz), 7.23-7.18 (m, 1H), 6.9-6.84 (m, 1H), 4.81-4.77 (m, 1H), 4.77 (s, 2H), 4.26 (t, 1H, J=6 Hz), 3.60 (s, 2H), 3.42 (s, 3H), 3.23-3.15 (m, 6H), 2.15-2.10 (m, 2H). LC_MS calculated for C$_{23}$H$_{24}$FN$_5$O$_5$ 469.47; observed 470.0.

Example 12: 6-(5-(3-(((6-fluoro-1-methyl-2-oxoindolin-7-yl)methyl)amino)propyl)-2-oxooxazolidin-3-yl)-2H-benzo[b][1,4]oxazin-3(4H)-one

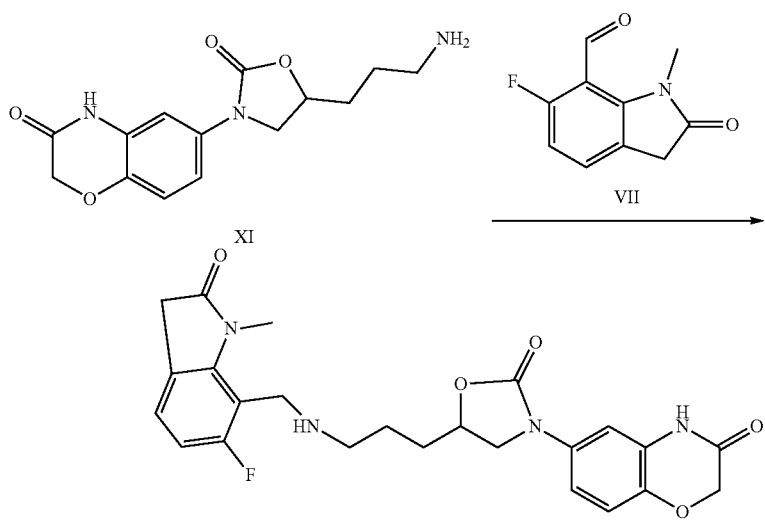

Example 12

To a stirred solution of XI (0.1 g, 0.34 mmol) and 6-fluoro-1-methyl-2-oxoindoline-7-carbaldehyde, VII (0.066 g, 0.34 mmol) in methanol (5 ml), glacial acetic acid (0.2 ml) and stirred at 25° C. for 15 min. Then, cooled to 0° C., sodium cyanoborohydride resin (0.295 g, 0.68 mmol) was added and stirred at 25° C. for 6 h. After completion of reaction, the reaction mixture was filtered to remove the resin and the filtrate was concentrated under reduced pressure. It was purified by reverse phase preparative HPLC to obtain example 12 (0.04 g, 25%). $^1$H NMR (400 MHz, DMSO-$d_6$): (510.76 (s, 1H), 8.79 (brs, 2H), 7.4-7.3 (m, 2H), 7.0-6.9 (m, 3H), 4.75-4.7 (m, 1H), 4.55 (s, 2H), 4.5-4.4 (m, 2H), 3.7-3.63 (m, 3H), 3.41 (s, 3H), 3.2-3.16 (m, 2H), 1.85-1.7 (m, 4H). LCMS calculated for $C_{24}H_{25}FN_4O_5$ 468.49, observed 469.0.

Example 13: Chiral 6-(5-(2-((2-(6-fluoro-1-methyl-2-oxoindolin-7-yl)ethyl)amino)ethyl)-2-oxooxazolidin-3-yl)-2H-pyrido[3,2-b][1,4]oxazin-3(4H)-one (Enantiomer1)

Example 14: Chiral 6-(5-(2-((2-(6-fluoro-1-methyl-2-oxoindolin-7-yl)ethyl)amino)ethyl)-2-oxooxazolidin-3-yl)-2H-pyrido[3,2-b][1,4]oxazin-3(4H)-one (Enantiomer2)

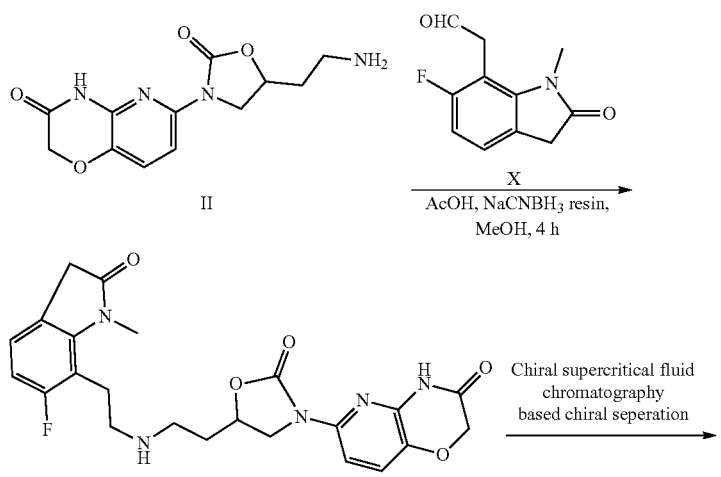

Example 11

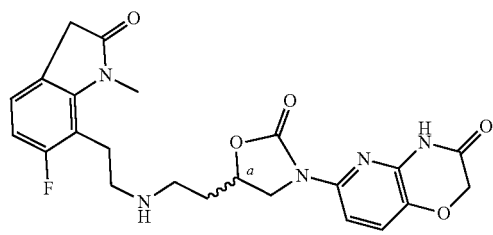

Example 13 (Enantiomer1)

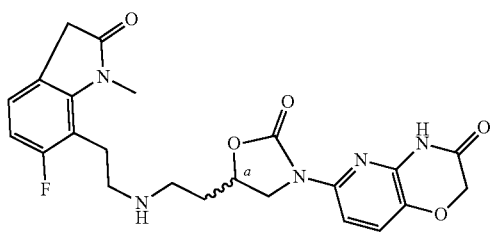

Example 14 (Enantiomer2)

a= Absolute configuration unknown

To a mixture of X (1 g, 4.82 mmol) and amine II (1.60 g, 5.79 mmol) in dry MeOH (20 mL) and DCM (20 mL) was added AcOH (1 mL) and allowed to stir for 16 h. To this was added Sodium cyanoborohydride resin (3.97 g, 9.65 mmol) and stirred for 15 min. The reaction mixture was filtered and concentrated. Crude was purified by column chromatography (230/400 mesh, 7% DCM in MeOH) to get the racemic mixture of compound as an Off-white solid (Example 11, 0.5 g, 26%)

The Part of racemic compound (Example 11, 0.5 gm) was separated into its enantiomers (Example 13 and Example 14) by Chiral supercritical fluid chromatography (SFC) using the following SCF conditions
Column: YMC Cellulose
Mobile phase: $CO_2$: 20 mm Ammonia in Methanol (65:35)
flow Rate: 4 mL/min
Injection volume: 0.5 ml
Back Pressure: 100 bar
Wave length: 212 nm
Cycle time: 11.0 min
The separated pure fractions were collected and their solvents were evaporated under vacuo afforded enantiomer1 and 2 as off white solid.

Enantiomer 1 (Example 13): 0.200 gm, Chiral HPLC Retention Time: 3.7 Min

LC_MS Calc. for Calc. for $C_{23}H_{24}FN_5O_5$, 469.47; Obs 470.0; $[M^++H]$; HPLC Purity=95.07% (HPLC Column: Atlantis dC18 (250*4.6) mm 5 µm, Mobile Phase A: 0.1% TFA in water, Mobile Phase B: Acetonitrile.); $^1$H NMR (400 MHz, DMSO-$D_6$): δ 11.23 (s, 1H), 7.59 (d, 1H, J=8.4 Hz), 7.44 (d, 1H, J=8.8 Hz), 7.18-7.15 (m, 1H), 6.86-6.82 (m, 1H), 4.79-4.76 (m, 1H), 4.62 (s, 2H), 4.26-4.22 (m, 1H), 3.79-3.75 (m, 1H), 3.53 (s, 2H), 3.12-3.10 (m, 2H), 2.96 (s, br, 4H), 2.03 (s, br, 2H).

Enantiomer 2 (Example 14): 0.200 gm Chiral HPLC Retention Time: 4.5 Min

LC_MS Calc. for Calc. for $C_{23}H_{24}FN_5O_5$, 469.47; Obs 470.0; $[M^++H]$; HPLC Purity=97.02% (HPLC Column: Atlantis dC18 (250*4.6) mm 5 µm, Mobile Phase A: 0.1% TFA in water, Mobile Phase B: Acetonitrile.); $^1$H NMR (400 MHz, DMSO-$D_6$): δ 11.20 (s, 1H), 7.59 (d, 1H, J=8.8 Hz), 7.43 (d, 1H, J=8.8 Hz), 7.13-7.09 (m, 1H), 6.82-6.78 (m, 1H), 4.76-4.73 (m, 1H), 4.61 (s, 2H), 4.23-4.18 (m, 1H), 3.76-3.72 (m, 1H), 3.50 (s, 2H), 3.47 (s, 3H), 2.99-2.96 (m, 2H), 2.72-2.65 (m, 4H), 1.90-1.83 (m, 2H).

Example 15: 6-(5-(2-((2-(6-fluoro-1-methyl-2-oxoindolin-7-yl)-2-hydroxyethyl) amino)ethyl)-2-oxoxazolidin-3-yl)-2H-pyrido[3,2-b][1,4]oxazin-3(4H)-one

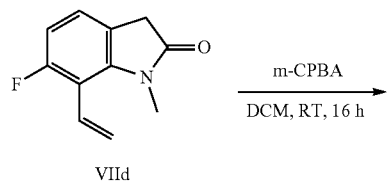

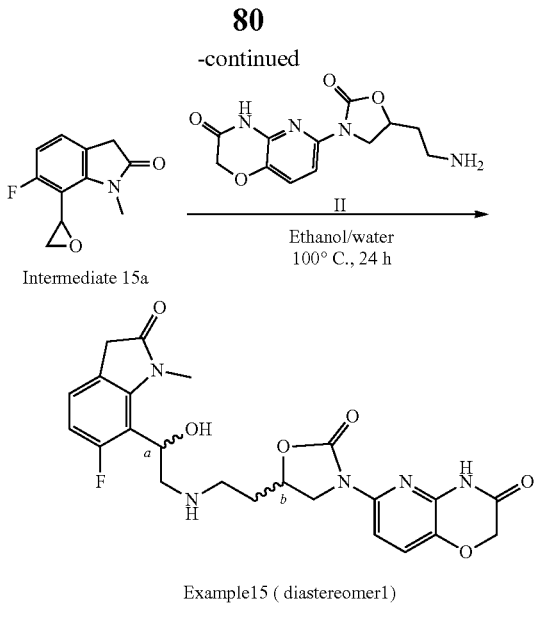

Intermediate 15a

Example15 ( diastereomer1)

a&b= configuration unknown

Step 1: 6-fluoro-1-methyl-7-(oxiran-2-yl)indolin-2-one(15a)

To a solution of VIId (2 g, 10.45 mmol) in DCM (60 mL) and 5% NaHCO$_3$ aqueous solution (20 mL) was added meta chloroperbenzoic acid (5.41 g 31.38 mmol) at 0° C. The reaction mass was stirred at room temperature for 16 h. After completion of the reaction, added 5% NaHCO$_3$ aqueous solution (50 mL) and extracted with ethyl acetate (2×100 mL). The combined organic layers were washed with brine, dried over sodium sulphate and evaporated under reduced pressure to get crude to afford compound 15a (1.3 g, 60% yield) as off-white solid. LC_MS Calc. for Calc. for $C_{11}H_{10}FNO_2$, 207.20; Obs 208.1 $[M^++H]$ $^1$H NMR (400 MHz, DMSO-$D_6$): δ 7.90 (s, 1H), 7.72-7.52 (m, 1H), 7.26-7.21 (m, 1H), 6.85-6.78 (m, 1H), 4.25 (s, 1H), 3.54 (s, 2H), 3.33 (s, 3H).

Step 2: 6-(5-(2-((2-(6-fluoro-1-methyl-2-oxoindolin-7-yl)-2-hydroxyethyl) amino)ethyl)-2-oxooxazolidin-3-yl)-2H-pyrido[3,2-b][1,4]oxazin-3(4H)-one To a mixture of 15a (1.3 g, 6.27 mmol) and amine II (2.09 g, 7.52 mmol) in ethanol (52 mL) and water (13 mL) was heated at 100° C. in a sealed tube for 24 h. After completion, the reaction mixture was concentrated to get the crude product. The crude was purified by reverse phase grace column chromatography to afford desired product (Example 15) as an off white solid (0.3 g) and the only one diastereomer was obtained from the epoxide 15a opening reaction. LC_MS Calc. for Calc. for $C_{23}H_{24}FN_5O_6$, 485.47; Obs 486.2; $[M^++H]$; HPLC Purity=88.67% (HPLC Column: Atlantis dC18 (250*4.6) mm 5 µm, Mobile Phase A: 0.1% TFA in water, Mobile Phase B: Acetonitrile.); $^1$H NMR (400 MHz, DMSO-$D_6$): δ 11.22 (s, 1H), 8.78 (s, 1H), 7.59 (d, 1H, J=8.4 Hz), 7.45 (d, 1H, J=8.8 Hz), 7.25 (s, br, 1H), 6.31 (s, 1H), 4.79-4.78 (m, 1H), 4.62 (s, 1H), 4.28-4.23 (m, 2H), 3.61 (s, 3H), 3.46 (s, 3H), 3.17 (s, 2H), 2.16-2.09 (m, 2H).

Example 16: 6-(5-(2-((2-(5-Fluoro-3-methyl-2-oxo-2,3-dihydrobenzo[d]oxazol-4-yl)ethyl)amino)ethyl)-2-oxooxazolidin-3-yl)-2H-pyrido[3,2-b][1,4]oxazin-3(4H)-one

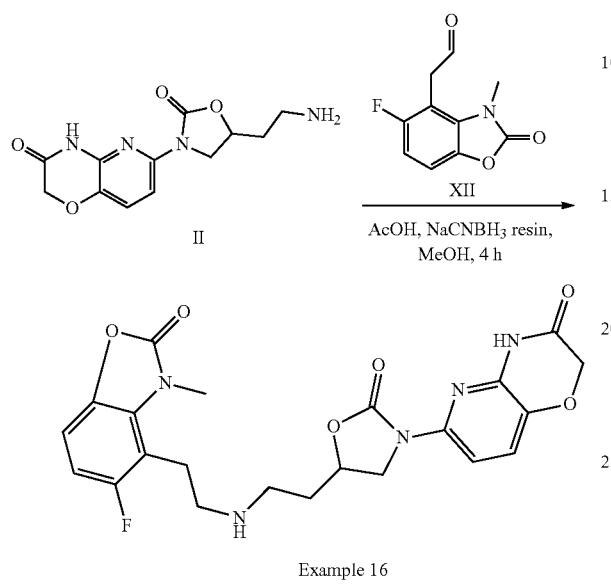

Example 16

To a mixture of XII (0.12 g, 0.57 mmol) and amine (II, 0.19 g, 0.68 mmol) in dry methanol (10 mL) and dichloromethane (10 mL) was added AcOH (0.10 mL) and allowed to stir for 16 hours at room temperature. To this was added MP-cyanoborohydride resin (0.46 g, 1.14 mmol) and stirred for another 15 minutes at room temperature. The reaction mixture was filtered and concentrated to remove methanol. The residue was diluted with dichloromethane (50 mL) and washed with 10% aqueous NaHCO₃. The organic layer was dried over Na₂SO₄ and concentrated to get the crude product. The crude was purified by preparative HPLC to afford Example 16 as an off-white solid (0.026 g, 10%). LC_MS: Calc. for $C_{22}H_{22}FN_5O_6$ 471.45; Obs. 472.0 [M+H]⁺; ¹H NMR (400 MHz, DMSO-D₆): δ 11.22 (brs, 1H), 8.67 (brs, 2H), 7.60 (d, J=8.4 Hz, 1H), 7.45 (d, J=8.8 Hz, 1H), 7.37-7.32 (m, 2H), 4.80-4.78 (m, 1H), 4.63 (s, 2H), 4.28-4.24 (m, 1H), 3.79-3.75 (m, 1H), 3.31 (s, 3H), 3.20-3.14 (m, 4H), 2.98-2.96 (m, 2H), 2.12-2.10 (m, 2H).

Example 17: 6-(5-(3-(((6-Fluoro-1-methyl-2-oxo-2,3-dihydro-1H-pyrrolo[3,2-b]pyridin-7-yl)methyl)amino)propyl)-2-oxooxazolidin-3-yl)-2H-pyrido[3,2-b][1,4]oxazin-3(4H)-one

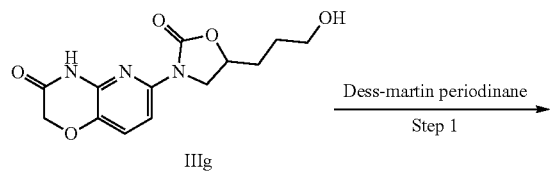

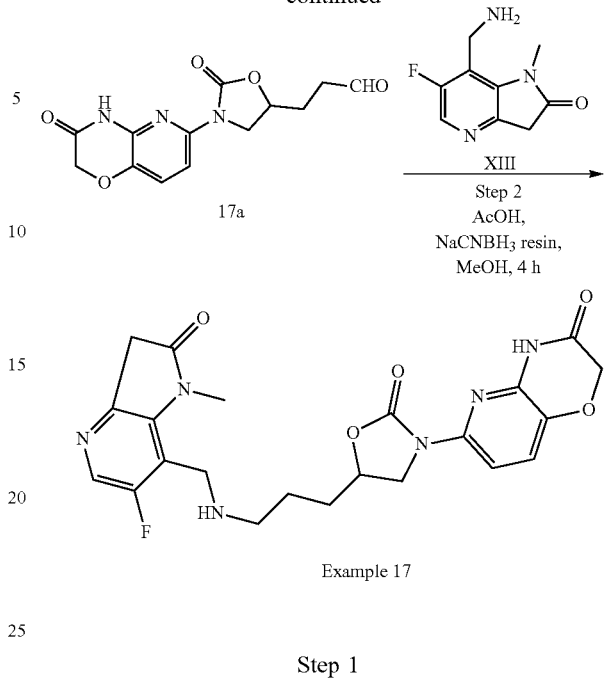

Example 17

Step 1

To a stirred solution of IIIg (1 g, 3.40 mmol) in DCM (20 mL), cooled to 0° C., was added Dess-martin periodinane (2.16 g, 5.11 mmmol) and allowed to stir at rt for 2 h. The reaction mixture was carefully quenched with NaHCO₃ solution (10 mL). The organic layer was separated and washed with sodiumthiosulphate solution (2×25 mL) and over Na₂SO₄, filtered and concentrated in vacuum to obtain colorless gummy solid of 17a. This was used in the next step without further purification (0.5 g, crude). LC_MS: Calculated for $C_{13}H_{13}N_3O_5$, 291.26, Observed=292.0

Step 2

To a mixture of XIII (0.20 g, 1.02 mmol) and aldehyde 17a (0.298 g, 1.02 mmol) in dry MeOH (6 mL) and DCM (6 mL) was added AcOH (0.20 mL) and allowed to stir for 16 h. To this was added Sodium cyanoborohydride resin (0.843 g, 2.04 mmol) and stirred for 15 min. The reaction mixture was filtered and concentrated. Crude was purified by column chromatography (230/400 mesh, 7% DCM in MeOH) to get desire compound Example 17 as white solid (40 mg, 12%). LC_MS Calc. for Calc. for $C_{22}H_{23}FN_6O_5$, 470.46; Obs 471.2; [M⁺+H]; HPLC Purity=94.20% (HPLC Column: Phenomenex Gemini-N×C18 (150*4.6) mm, 3 μm, Mobile Phase A: 10 mM NH4OAc in water, Mobile Phase B: Acetonitrile.); ¹H NMR (400 MHz, DMSO-D₆): δ 11.21 (s, 1H), 8.96 (s, br, 2H), 8.23 (s, 1H), 7.59 (d, 1H, J=8.8 Hz), 7.44 (d, 1H, J=8.4 Hz), 7.24-6.98 (m, 1H), 4.76 (s, br, 1H), 4.62 (s, 2H), 4.45 (s, 2H), 4.25-4.20 (m, 1H), 3.76-3.70 (m, 3H), 3.40 (s, 3H), 3.17-3.13 (m, 2H), 1.81-1.75 (m, 4H).

Example 18

Biological Activity
1. Antibacterial Activity:
The compounds of Formula I are of interest due to their potent antibacterial effects. The ability of the invention compounds disclosed herein to achieve an antibacterial effect may be evaluated with regard to their ability to inhibit the growth of bacterial species like *Escherichia coli* ATCC 25922, *Staphylococcus aureus* ATCC 29213, *Klebsiella pneumoniae* ATCC 13883, *Acinetobacter baumannii* ATCC 19606, *Pseudomonas aurigenosa* ATCC 27853, *Enterococcus faecalis* ATCC 29212 and *Enterococcus faecalis* ATCC 29212 using an assay based on the following Minimum Inhibitory Concentration (MIC) protocol:

The test bacteria are grown in Luria Bertani Broth (HI-MEDIA M1245), 25 grams of the powder is dissolved in 1000 ml distilled water and sterilized by autoclaving at 15 lbs pressure (121° C.) for 20 minutes. The medium sterility is checked by incubating at 37° C. for a period of 48 h.

Bacterial cultures that are stored as glycerol stocks at −80° C. are sub cultured on LB agar plates to obtain isolated colonies. A single colony of each strain is cultured in LB broth. The cultures are incubated at 37° C., 200 rpm till they reach an optical density (OD at 600 nm) of 0.8 to 1. This log phase culture is diluted in LB broth to a cell number of $5\text{-}8*10^5$ CFU/mL to be used as inoculum for MIC experiments. Test compounds are dissolved in dimethyl sulfoxide (DMSO) to a stock concentration of 4 mg/ml. A twofold dilution series of this DMSO stock is prepared in a 96 well V bottom microtitre plate from rows A to H. A 3 µL volume of these dilutions are transferred to a 96-well flat bottom microtitre assay plate. Controls to monitor the effects of DMSO and media sterility are included. Each well is inoculated with 150 µL of the above diluted culture. The plates are incubated at 37° C. overnight in a humidified incubator. The following morning, the plates are read using a Spectrophotometer at 600 nM wavelength. Minimum Inhibitory Concentration (MIC) is defined as the lowest drug concentration containing well which shows no turbidity. The antibacterial activity (MIC) determined against representative Gram positive (*S. aureus, E. faecalis*) and Gram negative (*E. coli, P. aurigenosa, K. pneumoniae* and *A. baumannii*) pathogen were reported Table 1. The exemplified compounds belonging to Formula I demonstrated potent antibacterial activity both Gram positive and Gram negative pathogens.

2. Enzyme Inhibition Assay: Determination $IC_{50}$ Against *E. coli* Gyrase Supercoiling The compounds belonging to Formula I or its stereoisomers, pharmaceutically acceptable salts, complexes, hydrates, solvates, tautomers, polymorphs, racemic mixtures, optically active forms and pharmaceutically active derivative thereof, for use in killing or inhibiting the growth of Gram-positive and Gram-negative bacteria through inhibition of bacterial Type II topoisomerases namely, DNA gyrase and Topo IV.

The present invention also provides evidence for treating infection caused both Gram positive and Gram negative bacteria through the inhibition of bacterial topoisomerases using *E. coli* DNA gyrase enzyme.

Procedure for *E. coli* DNA Gyrase Supercoiling Assay

*E. coli* gyrase supercoiling and its inhibition was assayed using a kit procured from Inpiralis (K0001) and the protocol (PMID: 2172086) was adapted with necessary modifications. The compounds to be tested are incubated for 10 minutes with 2.5 nM of *E. coli* DNA gyrase in a 30 µl volume reaction and 3.2% DMSO. The reactions are then started with the addition of 60 ng relaxed pBR322 plasmid DNA and continued for 45 min at 37° C. The reaction mixture contains 35 mM Tris.HCl (pH 7.5), 24 mM KCl, 1.8 mM spermidine, 4 mM $MgCl_2$, 2 mM DTT, 6.5% (w/v) glycerol, 0.1 mg/mL BSA, and 1 mM ATP. The reaction is then stopped by addition of 0.75 µL of Proteinase K (20 mg/mL) and 3 µL of 2% SDS and further incubated at 37° C. for 30 min. This was followed by the addition of 4 µL of STEB (40% (w/v) sucrose, 100 mM Tris-HCl pH8, 1 mM EDTA, 0.5 mg/ml Bromophenol Blue) and the supercoiled/relaxed forms of plasmid DNA were separated by agarose gel electrophoresis. The 1% agarose gels are run for 3 h at 4V/cm in 1×TAE (40 mM Tris, 20 mM Acetic acid, 1 mM EDTA). To visualize the DNA the gels are stained for 10 min with 0.7 µg/mL ethidium bromide and excess dye is removed by several washes with water. $IC_{50}$s are determined by quantifying the supercoiled and relaxed DNA in each of the reactions from a gel image by a densitometric method using the Quantity One Software (Bio-rad).

TABLE 1

Minimum Inhibitory Concentration (µg/mL) in LB Media

| Example | S. aureus ATCC 29213 | E. faecalis ATCC 29212 | E. coli ATCC 25922 | P. aurigenosa ATCC 27853 | K. pneumoniae ATCC 13883 | A. baumannii ATCC 19606 |
|---|---|---|---|---|---|---|
| 1 | 5 | 5 | 2.5 | 40 | 10 | 0.6 |
| 2 | 0.6 | 1.25 | 1.25 | 10 | 2.5 | 0.3 |
| 3 | 0.6 | 1.25 | 1.25 | 20 | 5 | 0.6 |
| 4 | >80 | >80 | >80 | >80 | >80 | >80 |
| 5 | 80 | 80 | 80 | >80 | >80 | 40 |
| 6 | 0.13 | 0.5 | 0.25 | 1 | 0.5 | 0.25 |
| 7 | 0.15 | 0.6 | 1.25 | 20 | 5 | 0.3 |
| 8 | 0.07 | 0.15 | 0.15 | 2.5 | 0.3 | 0.15 |
| 9 | 0.13 | 0.5 | 0.25 | 2 | 0.5 | 0.125 |
| 10 | 0.06 | 0.5 | 0.125 | 1 | 0.25 | 0.06 |
| 11 | 0.03 | 0.13 | 0.06 | 0.5 | 0.125 | 0.03 |
| 12 | 0.25 | 0.5 | 0.25 | 2 | 0.5 | 0.13 |
| 13 | 0.03 | 0.25 | 0.06 | 0.5 | 0.125 | 0.06 |
| 14 | 0.03 | 0.25 | 0.03 | 0.5 | 0.125 | 0.03 |
| 15 | 1 | 2 | 1 | 2 | 2 | 4 |
| 16 | 4 | 4 | 0.5 | 4 | 1 | 0.5 |
| 17 | 1 | 4 | 1 | >16 | 2 | 0.5 |
| Ciprofloxacin | 0.4 | 0.4 | 0.012 | 0.1 | 0.05 | 0.4 |

Procedure for *E. coli* Topoisomerase IV Decatenation Assay

*E. coli* topoisomerase IV decatenation activity and its inhibition was assayed using a kit procured from Inpiralis (D4002) and the kit protocol was adapted with necessary modifications similar to the gyrase supercoiling assays. The compounds to be tested were incubated for 10 minutes with 5 nM of *E. coli* topoisomerase IV in a 30 µl volume reaction and 3.2% DMSO. The reactions were started with the addition of 60 ng of kDNA and continued for 40 min at 37° C. The final reaction mixture contains 40 mM Tris.HCl (pH 7.6), 100 mM potassium glutamate, 10 mM magnesium acetate, 10 mM DTT, 1 mM ATP, and 50 µg/ml albumin. The reactions were stopped by addition of 0.75 µL of Proteinase K (20 mg/mL) and 3 µL of 2% SDS and further incubated at 37° C. for 30 min. This was followed by the addition of 4 µL of STEB (40% (w/v) sucrose, 100 mM Tris-HCl pH8, 1 mM EDTA, 0.5 mg/ml Bromophenol Blue) and the kDNA/minicircles forms were separated by agarose gel electrophoresis. The 1% agarose gels were run for 3 h at 4V/cm in 1×TAE (40 mM Tris, 20 mM Acetic acid, 1 mM EDTA). To visualize the DNA, the gels were stained for 10 min with 0.7 µg/mL ethidium bromide and excess dye was removed by several washes with water. $IC_{50}$s were determined by quantifying the Kinetoplast DNA band inside the gel well and decatenated minicircles that migrate into the gel in each of the reactions from a gel image by a densitometric method using the Quantity One Software (Bio-rad).

Representing examples belonging to Formula I were evaluated against of *E. coli* DNA gyrase and Topo IV enzyme using gel based supercoiling assay for gyrase inhibition and decatenation assay for Topo IV inhibition. The results of bacterial Type II Topo isomerases (Gyrase and Topo IV) were presented in the table 2. The results presented in the Table 2 indicates that compounds belonging to Formula I exerts its' antibacterial activity through inhibition bacterial type II topoisomerase activity and signifies the dual mode of inhibition for observed antibacterial activity of the compounds.

TABLE 2

| Example | *E. coli* DNA Gyrase $IC_{50}$ (µM) | *E. coli* Topo IV $IC_{50}$ (µM) |
| --- | --- | --- |
| 2 | 0.360 | ND |
| 4 | 14 | ND |
| 6 | 0.056 | 0.459 |
| 8 | 0.054 | 0.362 |
| 9 | 0.089 | ND |
| 10 | 0.106 | 0.398 |
| 11 | 0.055 | ND |
| 12 | 0.089 | 0.600 |
| 13 | 0.05 | ND |
| 14 | 0.100 | 0.036 |
| 15 | 0.135 | ND |
| Ciprofloxacin | 0.233 | 14.4 |
| Novobiocin | 0.058 | NA |

ND—Not determined,
NA—Not applicable $MIC_{50}$ and $MI_{90}$ Studies Using Clinical Strains To test if the compounds from the series are able to retain the antibacterial activity against clinical strains of bacteria, antibacterial susceptibility studies ($MIC_{50}$ and $MIC_{90}$ determination) were carried for a representative compound (Example 14) from the series using clinical strains of four gram negative bacterial species (*E. coli, P. aurigenosa, K. pneumoniae* and *A. baumannii*) according the standard CLSI guidelines and the results are presented in FIG. 1 and Table 3. The standard drugs ciprofloxacin and meropenem were as positive control in the study.

TABLE 3

Results of $MIC_{50}$ and $MIC_{90}$ studies

| | Ciprofloxacin | Meropenem | Example 14 |
| --- | --- | --- | --- |
| *E. coli* | | | |
| Number of strain | 201 | 201 | 201 |
| ATCC25922 | 0.015 | 0.06 | 0.06 |
| Minimum | 0.015 | 0.03 | 0.03 |
| $MIC_{50}$ (µg/ml) | 16 | 0.06 | 0.25 |
| $MIC_{90}$ (µg/ml) | 16 | 4 | 0.5 |
| Aba | | | |
| Number of strain | 169 | 169 | 169 |
| ATCC19606 | 0.5 | 0.5 | 0.06 |
| Minimum | 0.06 | 0.03125 | 0.015 |
| $MIC_{50}$ (µg/ml) | 16 | 8 | 0.25 |
| $MIC_{90}$ (µg/ml) | 16 | 32 | 0.5 |
| Kpn | | | |
| Number of strain | 211 | 211 | 211 |
| ATCC13883 | 0.03 | 0.06 | 0.25 |
| Minimum | 0.015 | 0.03 | 0.06 |
| $MIC_{50}$ (µg/ml) | 4 | 1 | 1 |
| $MIC_{90}$ (µg/ml) | 16 | 16 | 4 |
| Pae | | | |
| Number of strain | 215 | 215 | 215 |
| ATCC27853 | 0.25 | 0.5 | 0.5 |
| Minimum | 0.015 | 0.03 | 0.03125 |
| $MIC_{50}$ (µg/ml) | 0.125 | 2 | 0.5 |
| $MIC_{90}$ (µg/ml) | 16 | 8 | 1 |

The results presented in the Table 3 and FIG. 1 indicates that compounds belonging to formula I works against both drug sensitive and resistant clinical strains of gram negative bacteria and retain the antibacterial activity. The MIC 90 values of Example 14 are 0.5 to 4 µg/ml range for 4 bacterial species and it is found to be superior in comparison to standard drugs used in the study.

Mouse In-Vivo Pharmacokinetic Profile of Example 13

To assess the Oral and Intravenous pharmacokinetic profile of Example 13, pharmacokinetics (PK) of Example 13 was characterized in BALB/c mice following single intravenous (i.v.) dose of 2 mg/kg and single escalating oral doses of 2, 10, 50 and 100 mg/kg, respectively. This study was performed following all ethical practices as laid down in the guidelines for animal care (Registration number No. 1852/PO/Rc/S/16/CPCSEA). The study was approved by the Institutional Animals Ethics Committee (IAEC) of the test facility. For IVPK in BALB/c mice, the formulation used was DMSO: PEG400: Ethanol: Water (10:20:10:60 v/v) and Example 13 administered as solution. For POPK, the formulation used was 0.1% Tween80 in 0.25% CMC and Example 13 administered as suspension through an oral gavage. The plasma (mice) samples were analyzed by LC-MS/MS. PK parameters were estimated by non-compartmental analysis in Phoenix WinNonlin 6.4 The results of the per-oral and intravenous PK study of Example 13 are presented in Table 4 and 5

TABLE 4

NCA PK parameters of Example 13 in mice [i.v., 2 mg/kg]

| Parameter | Estimate |
| --- | --- |
| $K_e$ (1/h) | 0.403 |
| $t_{1/2}$ (h) | 1.718 |
| $AUC_{last}$ (h * µg/ml) | 0.352 |
| $AUC_{0-\infty}$ (h * µg/ml) | 0.352 |
| AUC (% Extrap) | 0.002 |

TABLE 4-continued

NCA PK parameters of Example 13 in mice [i.v., 2 mg/kg]

| Parameter | Estimate |
|---|---|
| CL (ml/h/kg) | 5688 |
| $V_{ss}$ (ml/kg) | 13339 |

TABLE 5

NCA PK parameters of example 13 in mice following single oral doses

| Parameter | Dose [mg/kg] | | | |
| | 2 | 10 | 50 | 100 |
| | Estimate | | | |
|---|---|---|---|---|
| $K_e$ (1/h) | 0.123 | 0.325 | 0.433 | 0.489 |
| $t_{1/2}$ (h) | 5.626 | 2.132 | 1.600 | 1.417 |
| $T_{max}$ (h) | 1.0 | 0.50 | 0.50 | 1.0 |
| $C_{max}$ (µg/ml) | 0.006 | 0.108 | 0.740 | 2.380 |
| $T_{last}$ (h) | 24 | 8 | 8 | 8 |
| $C_{last}$ (µg/ml) | 0.004 | 0.009 | 0.028 | 0.072 |
| $AUC_{last}$ (h * µg/ml) | 0.07 | 0.311 | 1.902 | 4.699 |
| $AUC_{0-\infty}$ (h * µg/ml) | 0.07 | 0.335 | 1.967 | 4.821 |
| F (%) | 20.6 | 19.0 | 22.3 | 27.4 |
| AUC/Dose | 0.036 | 0.034 | 0.039 | 0.048 |
| $C_{max}$/dose | 0.003 | 0.011 | 0.015 | 0.024 |

Following a single i.v. dose of 2.0 mg/kg in BALB/c mice, Example 13 showed high systemic clearance [5.7 L/h/kg], a very high volume of distribution at steady state [13.3 L/kg], and a moderate t/2 of 1.7 h. Following single oral doses of 2, 10, 50 and 100 mg/kg in BALB/c mice, the $AUC_{0-\infty}$ ranged between 0.07 to 4.82 µg·h/ml, $C_{max}$ ranged between 0.004 to 0.072 µg/ml and $t_{1/2}$ ranged between 1.4 to 5.6 h. The oral bioavailability was moderate and ranged between 19-27%.

The $AUC_{0-\infty}$ increased linearly [$r^2$=0.9914] with dose [AUC/Dose range 0.036 to 0.048]. $C_{max}$ also increased linearly with dose between 10 and 100 mg/kg [$C_{max}$/Dose range 0.011 to 0.024].

Figure 2:
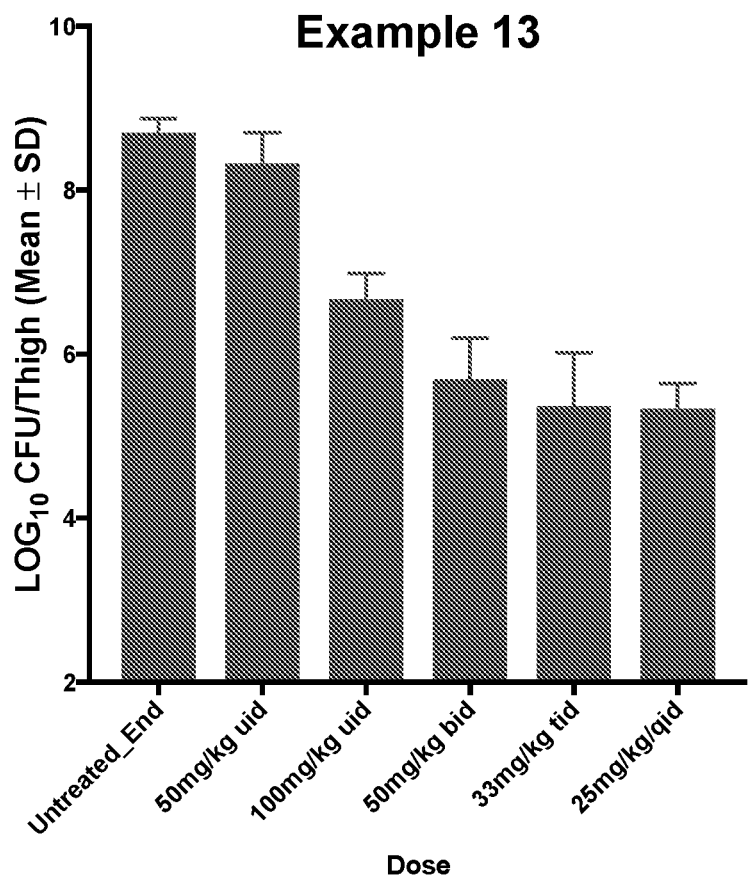
FIG. 2 illustrates the in vivo efficacy of Example 13 in mice thigh infection model, in accordance with an embodiment of the present disclosure.

In Vivo Efficacy in the Mouse E. coli Thigh Model:

To assess the Oral efficacy, Example 13 was tested in BALB/c mice thigh infection model following per oral doses of 100 mg/kg once, 50 mg/kg once and twice, 33 mg/kg thrice and 25 mg/kg four times over a 24 hour period post infection. This study was performed following all ethical practices as laid down in the guidelines for animal care (Registration number No. 1852/PO/Rc/S/16/CPCSEA). The study was approved by the Institutional Animals Ethics Committee (IAEC) of the test facility. The formulation used was 0.1% Tween80 in 0.25% CMC and Example 13 administered as suspension through an oral gavage. Neutropenic mice were infected with [~1×10$^6$ CFU/mouse] E. coli [ATCC 25922] by intramuscular route. Two hours post infection, mice were treated orally with total doses of 100, 50, 50, 33 and 25 mg/kg of Example 13 as one, two, three and four equally divided doses over a 24 h period. Animals were sacrificed 24 hr post infection and thigh tissues were harvested to enumerate the bacterial CFU count. Thigh muscles were placed in 1 ml of sterile LB broth and homogenized using a homogenizer (Omni Tip (220 volt hand held)). Serial ten-fold dilutions of the thigh homogenates were prepared in sterile LB broth, 0.05 ml of four dilutions for each thigh was plated onto Lactose agar plates. Bacterial colonies were enumerated on each plate following ~20 hours of incubation at 37° C. to determine the density of bacteria per thigh. The Mean±SD bacterial density Log 10 CFU/thigh was estimated for each group. The means of the treated groups were compared with the corresponding vehicle groups using a one way ANOVA at a 95% confidence levels. A P<0.05 was considered significant. The mean Log 10 CFU/thigh reduction at 24 h post treatment relative to the 2 h infection control was estimated for each group. The results of the efficacy study is presented in FIG. 2.

Example 13 showed significant efficacy when dosed with 100 mg/kg single, two, three and four equally divided doses, whereas single dose of 50 mg/kg was found to be ineffective.

Advantages

The above mentioned implementation examples as described on this subject matter and its equivalent thereof have many advantages, including those which are described.

The compounds of the present disclosure show high antibacterial activity against various pathogens including Gram-positive and Gram-negative bacteria through the inhibition of bacterial topoisomerase via a novel mechanism.

Although the subject matter has been described in considerable detail with reference to certain embodiments thereof, other embodiments are possible. As such, the spirit and scope of the invention should not be limited to the description of the embodiments contained herein.

We claim:
1. A compound of Formula I:

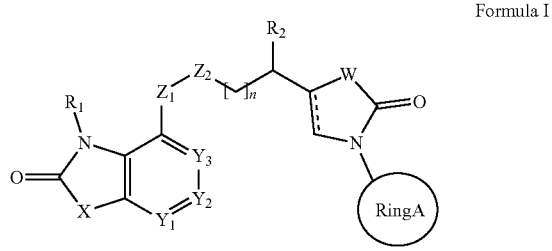

Formula I or a pharmaceutically acceptable salt, stereoisomer, or tautomer thereof,
wherein:
Ring A is selected from the group consisting of:

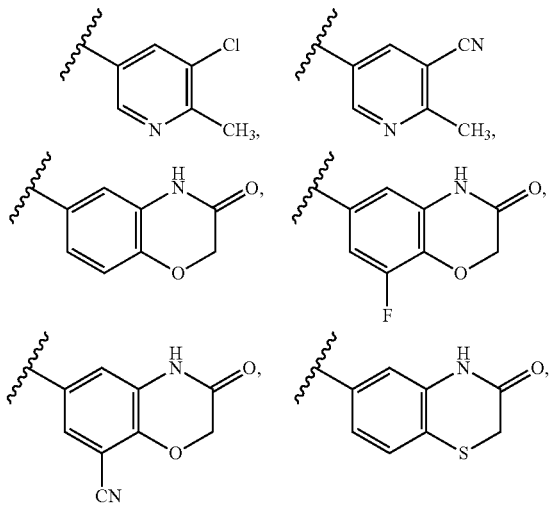

-continued

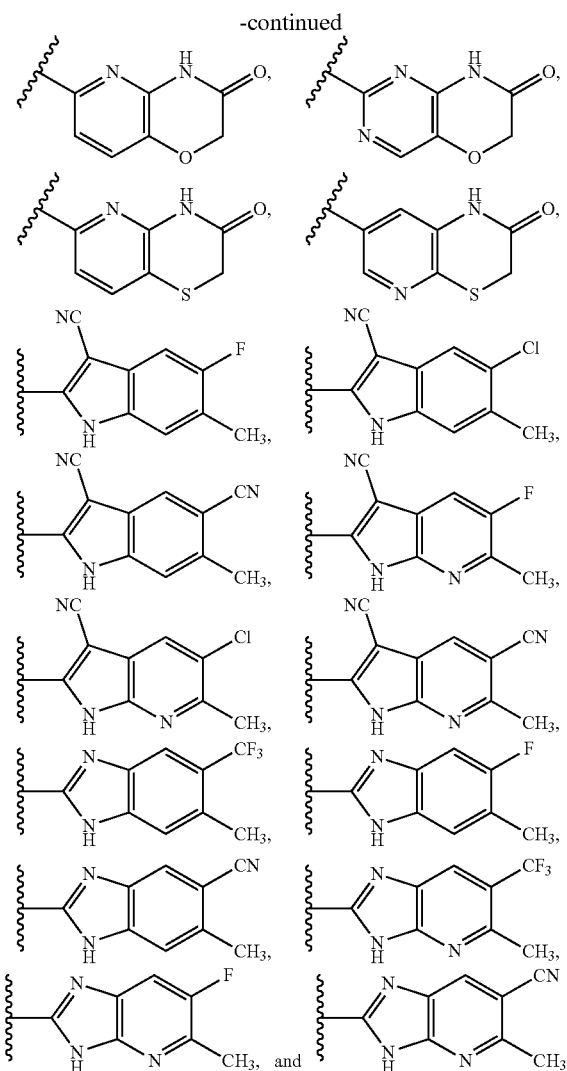

X is —CR₃R₄—, —NH—, —N(C₁₋₆ alkyl)-, or —O—;
Y₁ is CR₅ or N;
Y₂ is CH or N;
Y₃ is CR₆ or N;
Z₁-Z₂ is —(C₁₋₆ alkylene)-NH—, wherein the C₁₋₆ alkylene is optionally substituted with OH;
R₁ is hydrogen, C₁₋₆ alkyl, C₂₋₆ alkenyl, or C₃₋₆ cycloalkyl, wherein the C₁₋₆ alkyl, C₂₋₆ alkenyl, and C₃₋₆ cycloalkyl are each optionally substituted with 1, 2, or 3 substituents independently selected from the group consisting of halogen, NH₂, NH(C₁₋₆ alkyl), N(C₁₋₆ alkyl)₂, NH(C₃₋₆ cycloalkyl), OH, OC₁₋₆ alkyl, and oxetanyl;
R₂ is hydrogen, NH₂, or OH;
R₃ is hydrogen, halogen, or C₁₋₆ alkyl;
R₄ is hydrogen, halogen, or C₁₋₆ alkyl;
R₅ is hydrogen, halogen, CN, C₁₋₆ alkyl, OC₁₋₆ alkyl, or OC₁₋₆ haloalkyl;
R₆ is hydrogen, halogen, CN, C₁₋₆ alkyl, OC₁₋₆ alkyl, or OC₁₋₆ haloalkyl;
W is —O—;
n is 1 or 2; and
is absent.

2. The compound of claim 1, or a pharmaceutically acceptable salt, stereoisomer, or tautomer thereof, wherein:

X is —CR₃R₄—, —NH—, —N(CH₃)—, or —O—;
Z₁-Z₂ is —CH₂—NH—, —(CH₂)₂—NH—, or —CH(OH)CH₂—NH—;
R₁ is hydrogen, C₁₋₆ alkyl, C₂₋₆ alkenyl, or C₃₋₆ cycloalkyl, wherein C₁₋₆ alkyl is optionally substituted with 1, 2, or 3 substituents independently selected from the group consisting of F, NH₂, NH(C₁₋₂ alkyl), N(C₁₋₂ alkyl)₂, NH(C₃₋₆ cycloalkyl), OH, OCH₃, and oxetanyl;
R₃ is hydrogen, F, or CH₃;
R₄ is hydrogen, F, or CH₃;
R₅ is hydrogen, F, Cl, CN, CH₃, OCH₃, OCHF₂, or OCF₃; and
R₆ is hydrogen, F, CN, OCH₃, OCHF₂, or OCF₃.

3. The compound of claim 1, wherein the compound is selected from the group consisting of:

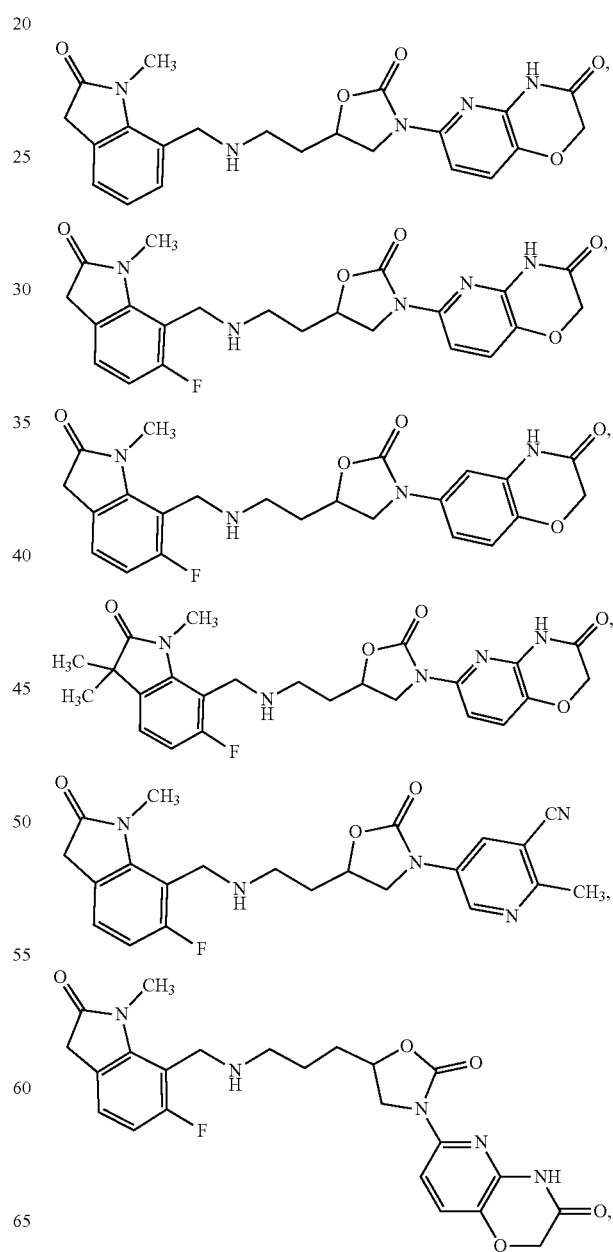

-continued

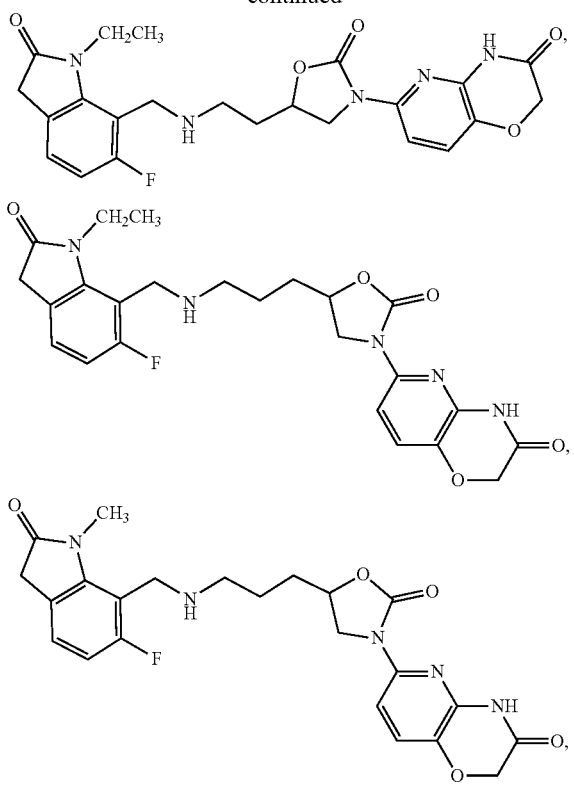

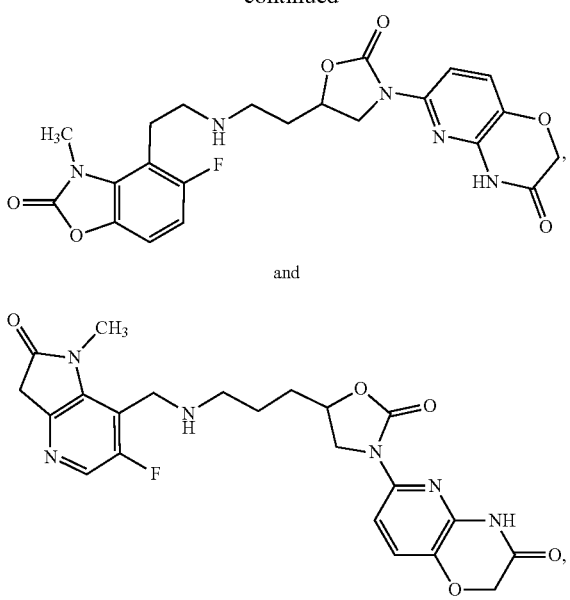

and or a pharmaceutically acceptable salt, stereoisomer, or tautomer thereof.

4. A pharmaceutical composition comprising a compound of claim 1, or a pharmaceutically acceptable salt, stereoisomer, or tautomer thereof, and a pharmaceutically acceptable carrier.

5. The pharmaceutical composition of claim 4, wherein the pharmaceutical composition further comprises at least one antibiotic.

6. A pharmaceutical composition comprising a compound of claim 1, or a pharmaceutically acceptable salt, stereoisomer, or tautomer thereof, at least one antibiotic, and a pharmaceutically acceptable carrier.

7. A method for reducing a bacterial infection in a subject, comprising administering to the subject in need thereof an effective amount of a compound of claim 1, or a pharmaceutically acceptable salt, stereoisomer, or tautomer thereof.

8. The method of claim 7, wherein the bacterial infection is caused by Gram-positive bacteria or Gram-negative bacteria.

9. The method of claim 8, wherein the bacterial infection is caused by *A. baumannii, E. coli, E. faecalis, E. faecium, K pneumonia, P. aeruginasa*, or *S. aureus*.

10. A process for preparing a compound of Formula I:

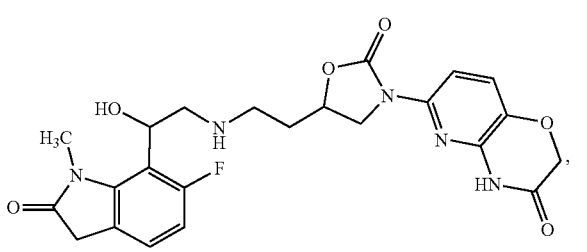

Formula I

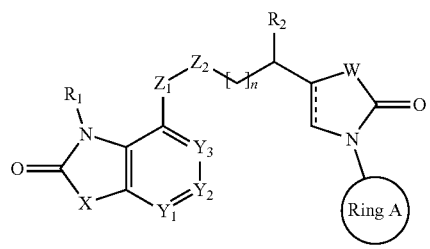

wherein:

Ring A is selected from the group consisting of:

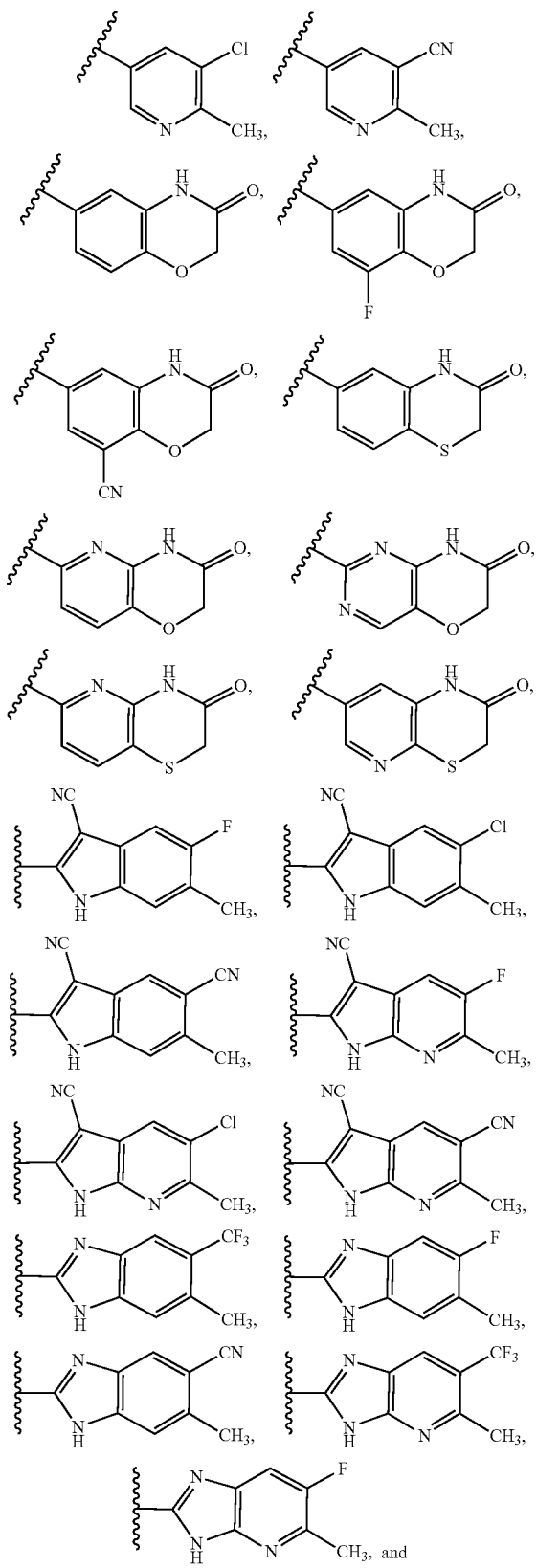

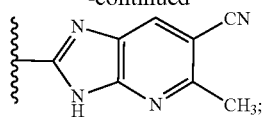

X is —CR₃R₄—, —NH—, —N(C₁₋₆ alkyl)-, or —O—;
Y₁ is CR₅ or N;
Y₂ is CH or N;
Y₃ is CR₆ or N;
Z₁-Z₂ is —(C₁₋₆ alkylene)-NH—;
R₁ is hydrogen, C₁₋₆ alkyl, C₂₋₆ alkenyl, or C₃₋₆ cycloalkyl, wherein the C₁₋₆ alkyl, C₂₋₆ alkenyl, and C₃₋₆ cycloalkyl are each optionally substituted with 1, 2, or 3 substituents independently selected from the group consisting of halogen, NH₂, NH(C₁₋₆ alkyl), N(C₁₋₆ alkyl)₂, NH(C₃₋₆ cycloalkyl), OH, OC₁₋₆ alkyl, and oxetanyl;
R₂ is hydrogen, NH₂, or OH;
R₃ is hydrogen, halogen, or C₁₋₆ alkyl;
R₄ is hydrogen, halogen, or C₁₋₆ alkyl;
R₅ is hydrogen, halogen, CN, C₁₋₆ alkyl, OC₁₋₆ alkyl, or OC₁₋₆ haloalkyl;
R₆ is hydrogen, halogen, CN, C₁₋₆ alkyl, OC₁₋₆ alkyl, or OC₁₋₆ haloalkyl;
W is —O—;
n is 1 or 2; and
is absent;

wherein the process comprises:
reacting a compound of the following formula:

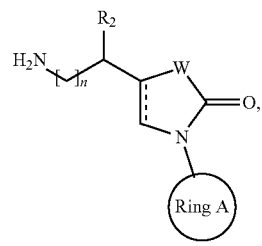

wherein:
Ring A is selected from the group consisting of:

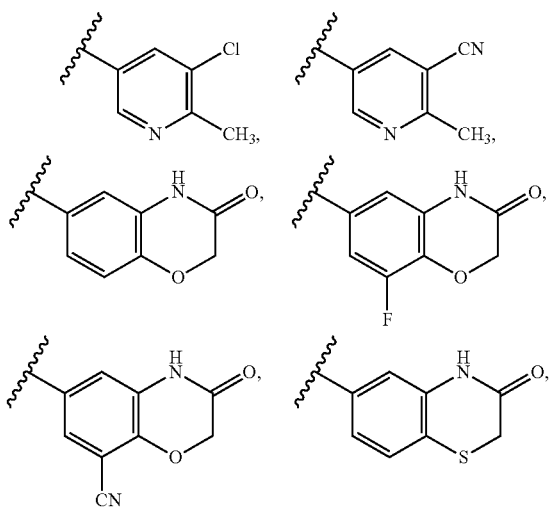

-continued

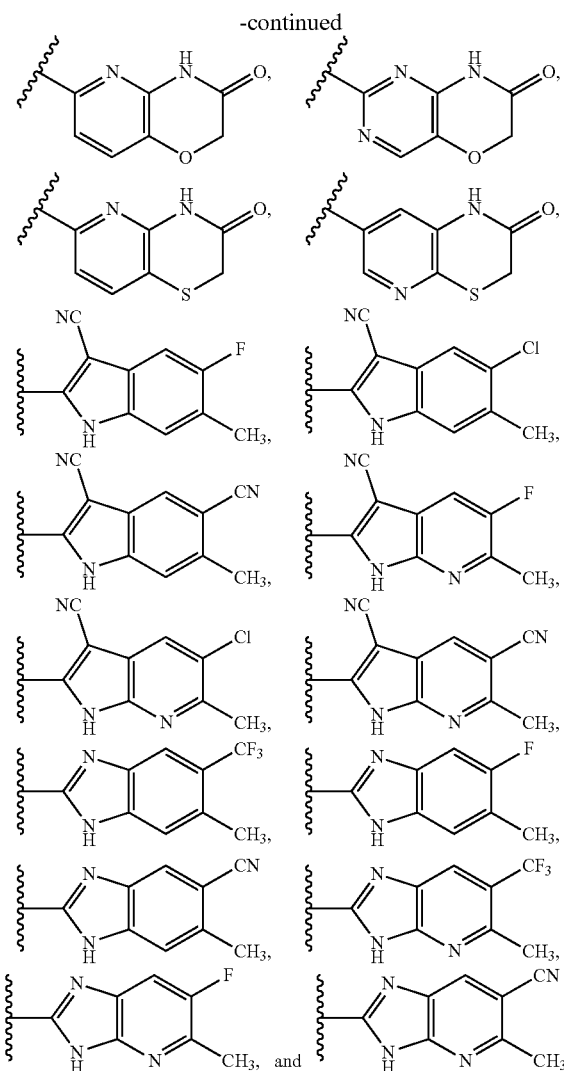

R$_2$ is hydrogen, NH$_2$, or OH;
W is —O—;
n is 1 or 2; and
is absent;
with a compound of the following formula:

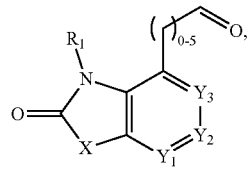

wherein:
X is —CR$_3$R$_4$—, —NH—, —N(C$_{1-6}$ alkyl)-, or —O—;
Y$_1$ is CR$_5$ or N;
Y$_2$ is CH or N;
Y$_3$ is CR$_6$ or N;
R$_1$ is hydrogen, C$_{1-6}$ alkyl, C$_{2-6}$ alkenyl, or C$_{3-6}$ cycloalkyl, wherein the C$_{1-6}$ alkyl, C$_{2-6}$ alkenyl, and C$_{3-6}$ cycloalkyl are each optionally substituted with 1, 2, or 3 substituents independently selected from the group consisting of halogen, NH$_2$, NH(C$_{1-6}$ alkyl), N(C$_{1-6}$ alkyl)$_2$, NH(C$_{3-6}$ cycloalkyl), OH, OC$_{1-6}$ alkyl, and oxetanyl;
R$_3$ is hydrogen, halogen, or C$_{1-6}$ alkyl;
R$_4$ is hydrogen, halogen, or C$_{1-6}$ alkyl;
R$_5$ is hydrogen, halogen, CN, C$_{1-6}$ alkyl, OC$_{1-6}$ alkyl, or OC$_{1-6}$ haloalkyl; and
R$_6$ is hydrogen, halogen, CN, C$_{1-6}$ alkyl, OC$_{1-6}$ alkyl, or OC$_{1-6}$ haloalkyl;

in the presence of a reducing agent selected from the group consisting of NaBH$_4$ and NaCNBH$_3$, to provide the compound of Formula I above.

11. A process for preparing a compound of Formula I:

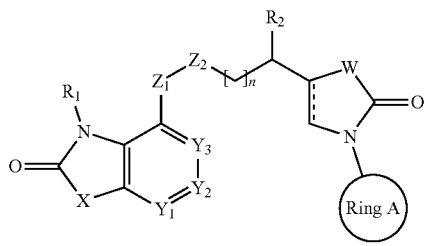

Formula I wherein:
Ring A is selected from the group consisting of:

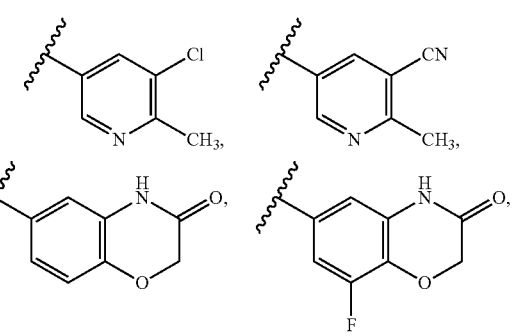

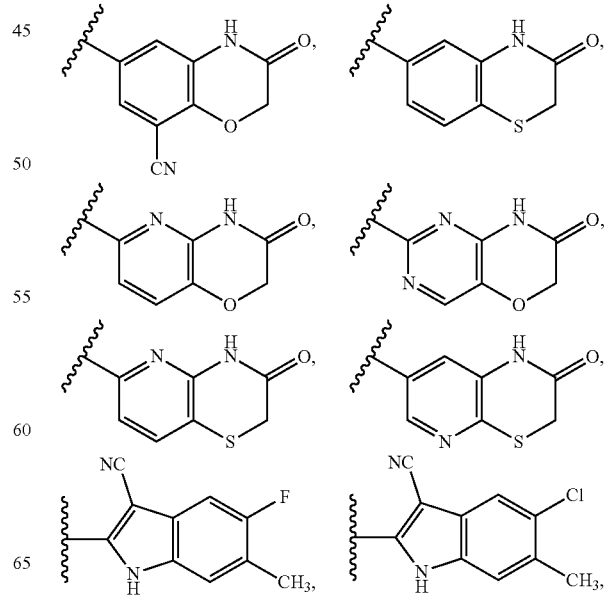

-continued

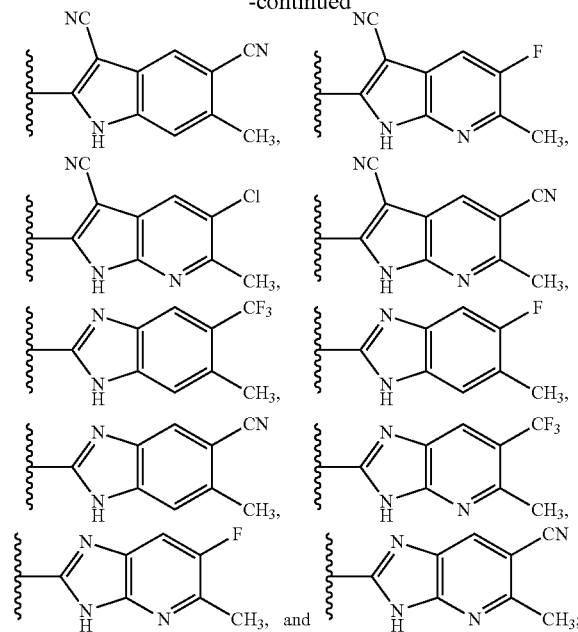

X is —CR₃R₄—, —NH—, —N(C₁₋₆ alkyl)-, or —O—;
Y₁ is CR₅ or N;
Y₂ is CH or N;
Y₃ is CR₆ or N;
Z₁-Z₂ is —(C₁₋₆ alkylene)-NH—;
R₁ is hydrogen, C₁₋₆ alkyl, C₂₋₆ alkenyl, or C₃₋₆ cycloalkyl, wherein the C₁₋₆ alkyl, C₂₋₆ alkenyl, and C₃₋₆ cycloalkyl are each optionally substituted with 1, 2, or 3 substituents independently selected from the group consisting of halogen, NH₂, NH(C₁₋₆ alkyl), N(C₁₋₆ alkyl)₂, NH(C₃₋₆ cycloalkyl), OH, OC₁₋₆ alkyl, and oxetanyl;
R₂ is hydrogen, NH₂, or OH;
R₃ is hydrogen, halogen, or C₁₋₆ alkyl;
R₄ is hydrogen, halogen, or C₁₋₆ alkyl;
R₅ is hydrogen, halogen, CN, C₁₋₆ alkyl, OC₁₋₆ alkyl, or OC₁₋₆ haloalkyl;
R₆ is hydrogen, halogen, CN, C₁₋₆ alkyl, OC₁₋₆ alkyl, or OC₁₋₆ haloalkyl;
W is —O—;
n is 1 or 2; and
is absent;
wherein the process comprises:
reacting a compound of the following formula:

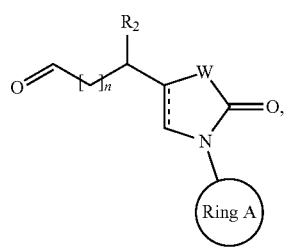

wherein:
Ring A is selected from the group consisting of:

-continued

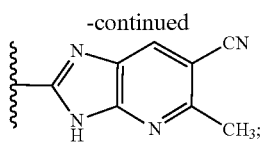

R$_2$ is hydrogen, NH$_2$, or OH;
W is —O—;
n is 1 or 2; and
is absent;
with a compound of the following formula:

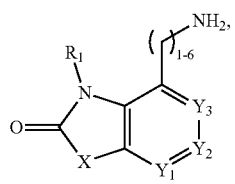

wherein:
X is —CR$_3$R$_4$—, —NH—, —N(C$_{1-6}$ alkyl)-, or —O—;
Y$_1$ is CR$_5$ or N;
Y$_2$ is CH or N;
Y$_3$ is CR$_6$ or N;
R$_1$ is hydrogen, C$_{1-6}$ alkyl, C$_{2-6}$ alkenyl, or C$_{3-6}$ cycloalkyl, wherein the C$_{1-6}$ alkyl, C$_{2-6}$ alkenyl, and C$_{3-6}$ cycloalkyl are each optionally substituted with 1, 2, or 3 substituents independently selected from the group consisting of halogen, NH$_2$, NH(C$_{1-6}$ alkyl), N(C$_{1-6}$ alkyl)$_2$, NH(C$_{3-6}$ cycloalkyl), OH, OC$_{1-6}$ alkyl, and oxetanyl;
R$_3$ is hydrogen, halogen, or C$_{1-6}$ alkyl;
R$_4$ is hydrogen, halogen, or C$_{1-6}$ alkyl;
R$_5$ is hydrogen, halogen, CN, C$_{1-6}$ alkyl, OC$_{1-6}$ alkyl, or OC$_{1-6}$haloalkyl; and
R$_6$ is hydrogen, halogen, CN, C$_{1-6}$ alkyl, OC$_{1-6}$ alkyl, or OC$_{1-6}$haloalkyl;
in the presence of a reducing agent selected from the group consisting of NaBH$_4$ and NaCNBH$_3$, to provide the compound of Formula I above.

12. A process for preparing a compound of Formula I:

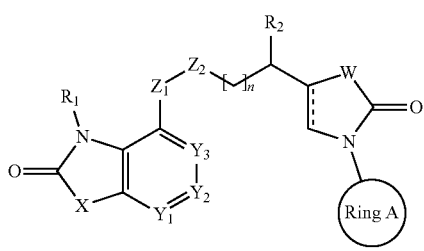

Formula I wherein:
Ring A is selected from the group consisting of:

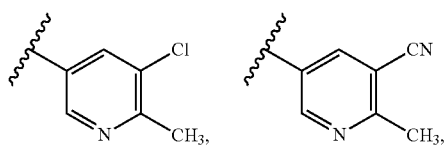

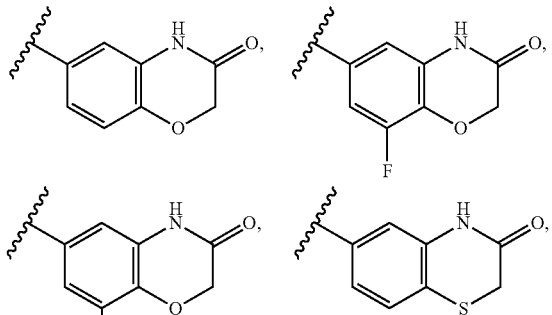
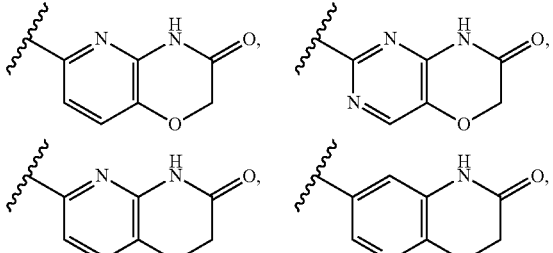
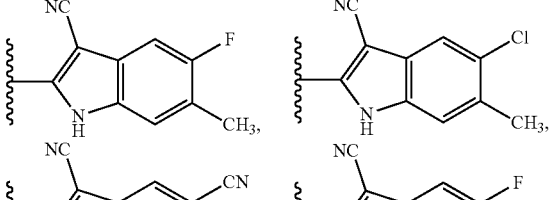
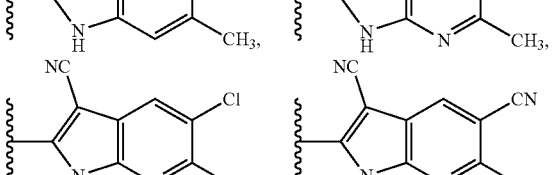

X is —CR$_3$R$_4$—, —NH—, —N(C$_{1-6}$ alkyl)-, or —O—;
Y$_1$ is CR$_5$ or N;
Y$_2$ is CH or N;
Y$_3$ is CR$_6$ or N;
Z$_1$-Z$_2$ is —(C$_{1-6}$ alkylene)-NH—, wherein the C$_{1-6}$ alkylene is substituted with OH;
R$_1$ is hydrogen, C$_{1-6}$ alkyl, C$_{2-6}$ alkenyl, or C$_{3-6}$ cycloalkyl, wherein the C$_{1-6}$ alkyl, C$_{2-6}$ alkenyl, and C$_{3-6}$ cycloalkyl are each optionally substituted with 1, 2, or 3 substituents independently selected from the group consisting of halogen, NH$_2$, NH(C$_{1-6}$ alkyl), N(C$_{1-6}$ alkyl)$_2$, NH(C$_{3-6}$ cycloalkyl), OH, OC$_{1-6}$ alkyl, and oxetanyl;

R$_2$ is hydrogen, NH$_2$, or OH;
R$_3$ is hydrogen, halogen, or C$_{1-6}$ alkyl;
R$_4$ is hydrogen, halogen, or C$_{1-6}$ alkyl;
R$_5$ is hydrogen, halogen, CN, C$_{1-6}$ alkyl, OC$_{1-6}$ alkyl, or OC$_{1-6}$ haloalkyl;
R$_6$ is hydrogen, halogen, CN, C$_{1-6}$ alkyl, OC$_{1-6}$ alkyl, or OC$_{1-6}$ haloalkyl;
W is —O—;
n is 1 or 2; and
is absent;

wherein the process comprises:
1) reacting a compound of the following formula:

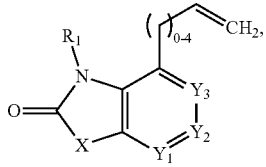

wherein:
X is —CR$_3$R$_4$—, —NH—, —N(C$_{1-6}$ alkyl)-, or —O—;
Y$_1$ is CR$_5$ or N;
Y$_2$ is CH or N;
Y$_3$ is CR$_6$ or N;
R$_1$ is hydrogen, C$_{1-6}$ alkyl, C$_{2-6}$ alkenyl, or C$_{3-6}$ cycloalkyl, wherein the C$_{1-6}$ alkyl, C$_{2-6}$ alkenyl, and C$_{3-6}$ cycloalkyl are each optionally substituted with 1, 2, or 3 substituents independently selected from the group consisting of halogen, NH$_2$, NH(C$_{1-6}$ alkyl), N(C$_{1-6}$ alkyl)$_2$, NH(C$_{3-6}$ cycloalkyl), OH, OC$_{1-6}$ alkyl, and oxetanyl;
R$_3$ is hydrogen, halogen, or C$_{1-6}$ alkyl;
R$_4$ is hydrogen, halogen, or C$_{1-6}$ alkyl;
R$_5$ is hydrogen, halogen, CN, C$_{1-6}$ alkyl, OC$_{1-6}$ alkyl, or OC$_{1-6}$ haloalkyl; and
R$_6$ is hydrogen, halogen, CN, C$_{1-6}$ alkyl, OC$_{1-6}$ alkyl, or OC$_{1-6}$ haloalkyl;

with m-chloroperoxybenzoic acid, to provide a compound of the following formula:

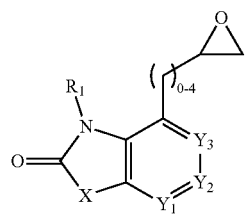

wherein:
X is —CR$_3$R$_4$—, —NH—, —N(C$_{1-6}$ alkyl)-, or —O—;
Y$_1$ is CR$_5$ or N;
Y$_2$ is CH or N;
Y$_3$ is CR$_6$ or N;
R$_1$ is hydrogen, C$_{1-6}$ alkyl, C$_{2-6}$ alkenyl, or C$_{3-6}$ cycloalkyl, wherein the C$_{1-6}$ alkyl, C$_{2-6}$ alkenyl, and C$_{3-6}$ cycloalkyl are each optionally substituted with 1, 2, or 3 substituents independently selected from the group consisting of halogen, NH$_2$, NH(C$_{1-6}$ alkyl), N(C$_{1-6}$ alkyl)$_2$, NH(C$_{3-6}$ cycloalkyl), OH, OC$_{1-6}$ alkyl, and oxetanyl;

R$_3$ is hydrogen, halogen, or C$_{1-6}$ alkyl;
R$_4$ is hydrogen, halogen, or C$_{1-6}$ alkyl;
R$_5$ is hydrogen, halogen, CN, C$_{1-6}$ alkyl, OC$_{1-6}$ alkyl, or OC$_{1-6}$ haloalkyl; and
R$_6$ is hydrogen, halogen, CN, C$_{1-6}$ alkyl, OC$_{1-6}$ alkyl, or OC$_{1-6}$ haloalkyl; and 2) reacting the compound formed in step 1) above with a compound of the following formula:

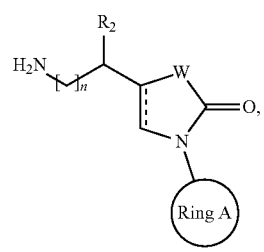

wherein:
Ring A is selected from the group consisting of:

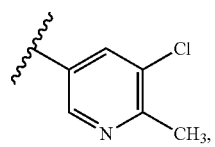 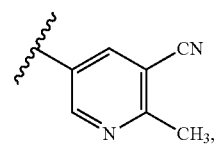

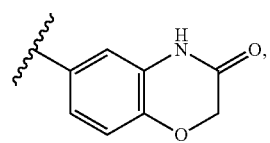 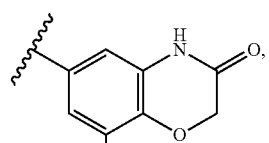

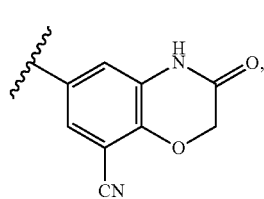 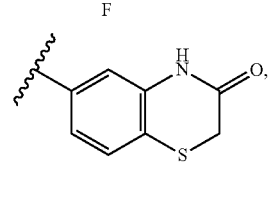

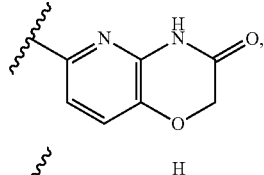 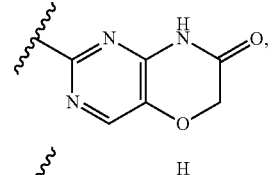

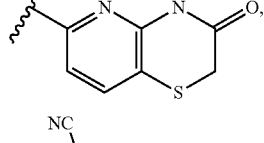 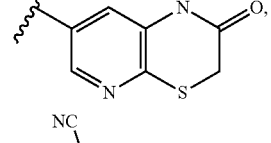

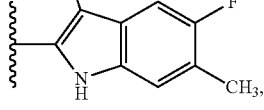 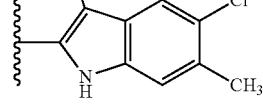

-continued
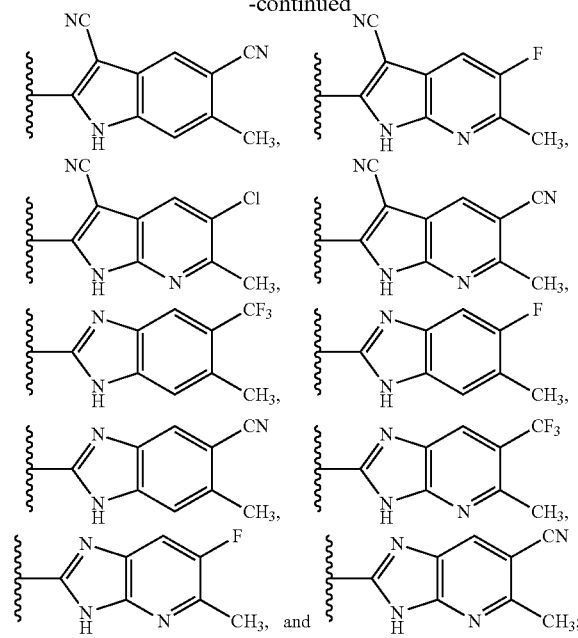
R₂ is hydrogen, NH₂, or OH;
W is —O—;
n is 1 or 2; and
is absent;
in the presence of at least one protic solvent, to provide the compound of Formula I above.
* * * * *